US008814915B2

(12) United States Patent
Hess et al.

(10) Patent No.: US 8,814,915 B2
(45) Date of Patent: Aug. 26, 2014

(54) DYNAMIC VERTEBRAL COLUMN PLATE SYSTEM

(75) Inventors: Harold Hess, Leawood, KS (US); Todd Moseley, Olathe, KS (US); Melissa Frock, Larwill, IN (US)

(73) Assignee: Spinal Simplicity LLC, Lenexa, KS (US)

( * ) Notice: Subject to any disclaimer, the term of this patent is extended or adjusted under 35 U.S.C. 154(b) by 0 days.

(21) Appl. No.: 13/587,961

(22) Filed: Aug. 17, 2012

(65) Prior Publication Data

US 2012/0310288 A1 Dec. 6, 2012

Related U.S. Application Data

(62) Division of application No. 12/724,420, filed on Mar. 15, 2010, now Pat. No. 8,262,711.

(60) Provisional application No. 61/160,154, filed on Mar. 13, 2009.

(51) Int. Cl.
*A61B 17/88* (2006.01)
(52) U.S. Cl.
USPC .......................................................... 606/279
(58) Field of Classification Search
CPC ........................ A61B 17/8004; A61B 17/8023
USPC .................................................. 606/279, 282
See application file for complete search history.

(56) References Cited

U.S. PATENT DOCUMENTS

| 4,269,180 A | 5/1981 | Dall et al. |
| 4,998,936 A | 3/1991 | Mehdian et al. |
| 5,180,381 A | 1/1993 | Aust et al. |
| 5,201,735 A | 4/1993 | Chapman et al. |
| 5,209,756 A | 5/1993 | Seedhom et al. |
| 5,330,477 A | 7/1994 | Crook |

(Continued)

FOREIGN PATENT DOCUMENTS

| EP | 1 169 971 A2 | 1/2002 |
| JP | 2008-534141 A | 8/2008 |

(Continued)

OTHER PUBLICATIONS

International Search Report, mailed Aug. 12, 2013, in corresponding PCT application PCT/US2013/040570.

(Continued)

*Primary Examiner* — Sameh Boles
(74) *Attorney, Agent, or Firm* — Edwards Wildman Palmer LLP; Scott D. Wofsy; George N. Chaclas

(57) ABSTRACT

A vertebral column construct for stabilizing a segment of a vertebral column can include first and second plate segments, and a spring connected between adjacent plate segments. The spring can be adapted and configured to provide a predetermined preload between the first and second plate segments. Such a preload can advantageously enhance fusion across a bone graft. Alternatively, the spring can be adapted and configured to resist, by a predetermined degree, loading between the first and second plate segments. A cam can be provided on one of the first and second plate segments, wherein engagement between the cam and the cam surface prevents dynamic connection between the first and second plates. The cam can be adapted and configured to adjust a preload applied between segments, such as by adjusting tension in the spring.

9 Claims, 49 Drawing Sheets

(56) References Cited

U.S. PATENT DOCUMENTS

| | | | |
|---|---|---|---|
| 5,364,399 | A | 11/1994 | Lowery et al. |
| 5,531,554 | A | 7/1996 | Jeanson et al. |
| 5,558,674 | A | 9/1996 | Heggeness et al. |
| 5,578,034 | A | 11/1996 | Estes |
| 5,603,713 | A | 2/1997 | Aust et al. |
| 5,735,853 | A | 4/1998 | Olerud |
| 5,836,948 | A | 11/1998 | Zucherman et al. |
| 5,876,402 | A | 3/1999 | Errico et al. |
| 5,941,881 | A | 8/1999 | Barnes |
| 6,017,345 | A | 1/2000 | Richelsoph |
| 6,066,141 | A | 5/2000 | Dall et al. |
| 6,093,201 | A | 7/2000 | Cooper et al. |
| 6,152,927 | A | 11/2000 | Farris et al. |
| 6,193,721 | B1 | 2/2001 | Michelson |
| 6,224,602 | B1 | 5/2001 | Hayes |
| 6,258,089 | B1 | 7/2001 | Campbell et al. |
| 6,261,291 | B1 | 7/2001 | Talaber et al. |
| 6,293,949 | B1 | 9/2001 | Justis et al. |
| D449,692 | S | 10/2001 | Michelson |
| 6,331,179 | B1 | 12/2001 | Freid et al. |
| 6,336,930 | B1 | 1/2002 | Stalcup et al. |
| 6,402,756 | B1 | 6/2002 | Ralph et al. |
| 6,413,259 | B1 | 7/2002 | Lyons et al. |
| 6,599,290 | B2 | 7/2003 | Bailey et al. |
| 6,626,907 | B2 | 9/2003 | Campbell et al. |
| 6,626,944 | B1 | 9/2003 | Taylor |
| 6,669,700 | B1 | 12/2003 | Farris et al. |
| 6,730,127 | B2 | 5/2004 | Michelson |
| 6,936,050 | B2 | 8/2005 | Michelson |
| 6,945,973 | B2 | 9/2005 | Bray |
| 6,949,123 | B2 | 9/2005 | Reiley |
| 7,001,387 | B2 | 2/2006 | Farris et al. |
| 7,033,377 | B2 | 4/2006 | Miller, III |
| 7,229,444 | B2 | 6/2007 | Boyd |
| 7,255,698 | B2 | 8/2007 | Michelson |
| 7,273,481 | B2 | 9/2007 | Lombardo et al. |
| 7,276,070 | B2 | 10/2007 | Muckter |
| D602,589 | S | 10/2009 | Bush, Jr. |
| 7,601,170 | B2 | 10/2009 | Winslow et al. |
| D603,964 | S | 11/2009 | Kriska et al. |
| 7,611,527 | B2 | 11/2009 | Freid et al. |
| 7,618,439 | B2 | 11/2009 | Zubok et al. |
| 7,625,378 | B2 | 12/2009 | Foley |
| 7,635,366 | B2 | 12/2009 | Abdou |
| 7,651,517 | B2 | 1/2010 | Konieczynski et al. |
| 7,749,256 | B2 | 7/2010 | Farris et al. |
| 7,887,547 | B2 | 2/2011 | Campbell et al. |
| 8,262,711 | B2 | 9/2012 | Hess |
| 2003/0130661 | A1 | 7/2003 | Osman |
| 2003/0208204 | A1 | 11/2003 | Bailey |
| 2003/0225409 | A1 | 12/2003 | Freid et al. |
| 2004/0133205 | A1 | 7/2004 | Thramann et al. |
| 2004/0220571 | A1 | 11/2004 | Assaker |
| 2005/0010215 | A1 | 1/2005 | Delecrin |
| 2005/0010227 | A1 | 1/2005 | Paul |
| 2005/0043732 | A1 | 2/2005 | Dalton |
| 2005/0065521 | A1 | 3/2005 | Steger |
| 2005/0137597 | A1 | 6/2005 | Butler et al. |
| 2005/0149026 | A1 | 7/2005 | Butler |
| 2005/0149027 | A1 | 7/2005 | Campbell et al. |
| 2005/0251138 | A1 | 11/2005 | Boris et al. |
| 2005/0261690 | A1 | 11/2005 | Binder et al. |
| 2005/0283152 | A1 | 12/2005 | Lindemann |
| 2006/0030852 | A1 | 2/2006 | Sevrain |
| 2006/0084985 | A1 | 4/2006 | Kim |
| 2006/0155285 | A1 | 7/2006 | Anderson |
| 2007/0073297 | A1 | 3/2007 | Reynolds |
| 2007/0213729 | A1 | 9/2007 | Lindemann et al. |
| 2008/0033448 | A1 | 2/2008 | Robinson |
| 2008/0269753 | A1* | 10/2008 | Cannestra ............ 606/70 |
| 2009/0012571 | A1 | 1/2009 | Perrow et al. |
| 2009/0254185 | A1 | 10/2009 | Dollinger |
| 2010/0016901 | A1 | 1/2010 | Robinson |
| 2010/0042160 | A1* | 2/2010 | Biyani et al. ............ 606/287 |
| 2010/0234895 | A1 | 9/2010 | Hess |

FOREIGN PATENT DOCUMENTS

| | | |
|---|---|---|
| WO | 00/78238 A1 | 12/2000 |
| WO | 02/24086 A1 | 3/2002 |
| WO | 2005/006997 A1 | 1/2005 |
| WO | 2006/104487 A1 | 10/2006 |
| WO | 2006/105124 A2 | 10/2006 |
| WO | 2006/119242 A1 | 11/2006 |
| WO | 2008/005380 A2 | 1/2008 |

OTHER PUBLICATIONS

Japanese Office Action mailed Nov. 26, 2013 in corresponding Japanese Application No. Tokugan 2011-554276.

* cited by examiner

Fig. 1A
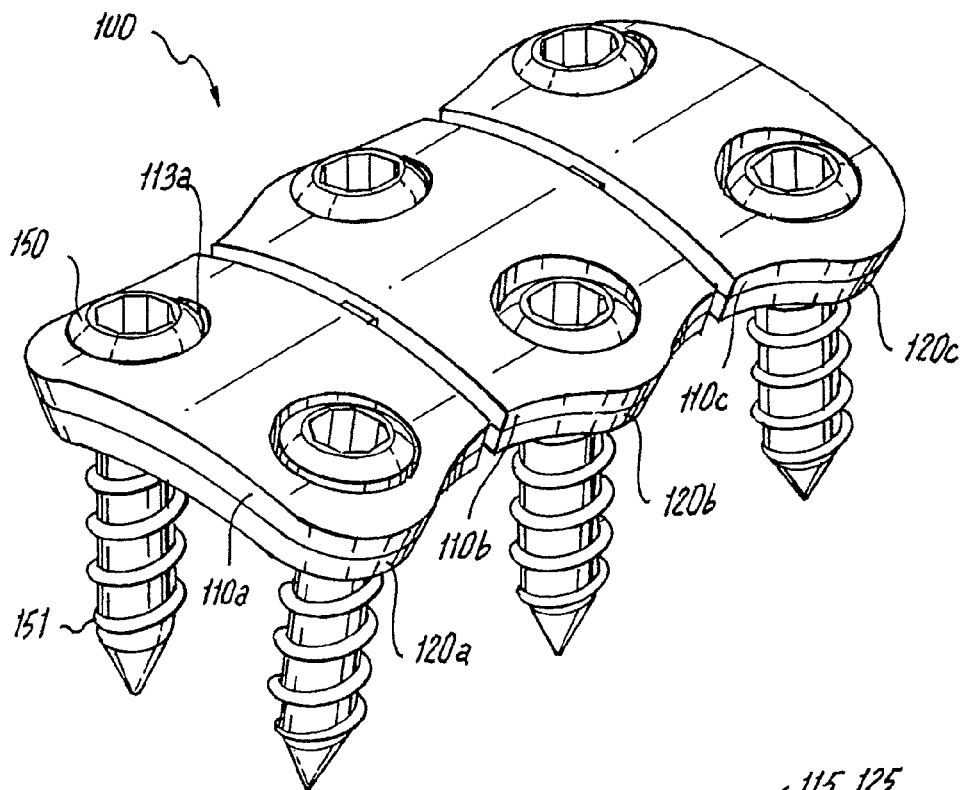
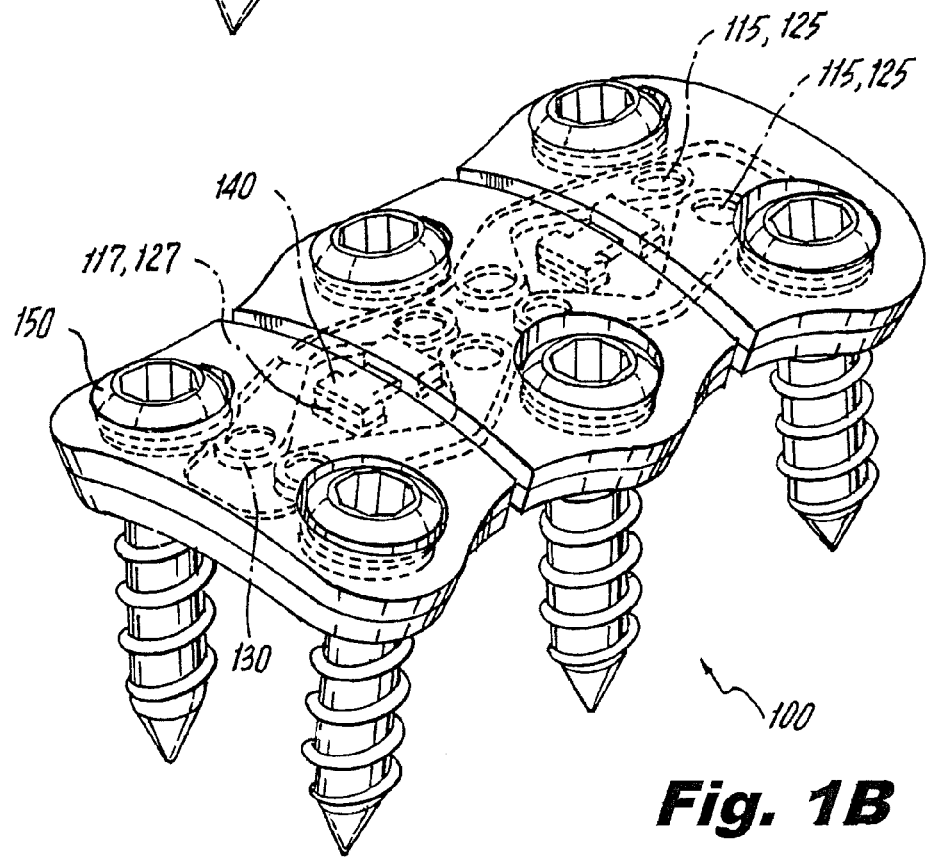
Fig. 1B

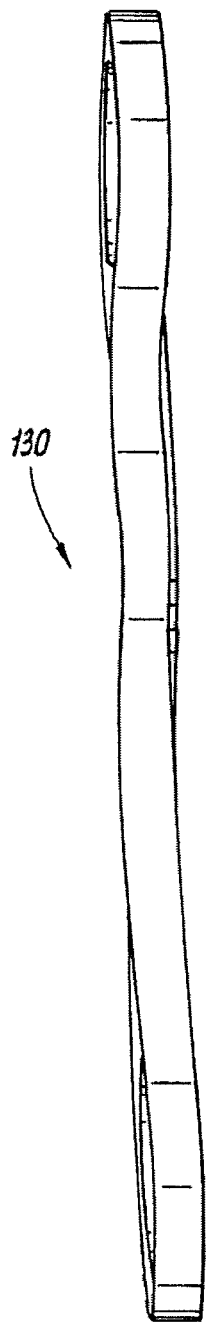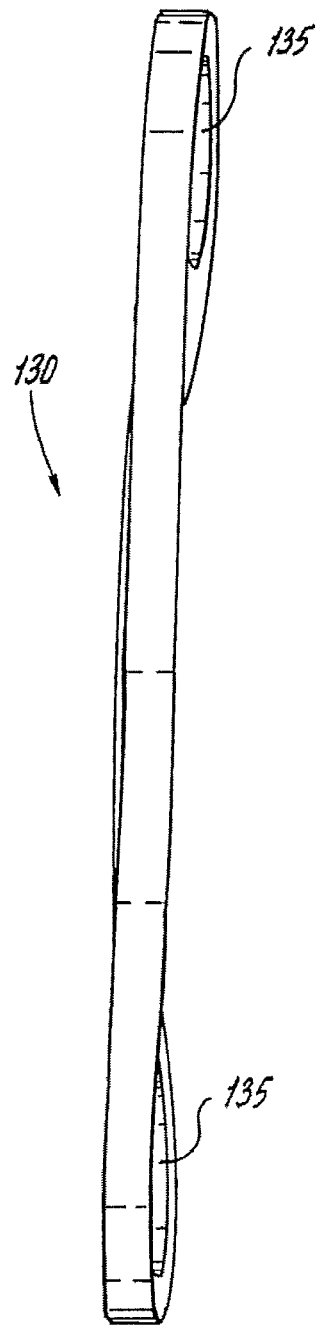
*Fig. 15E*            *Fig. 15F*

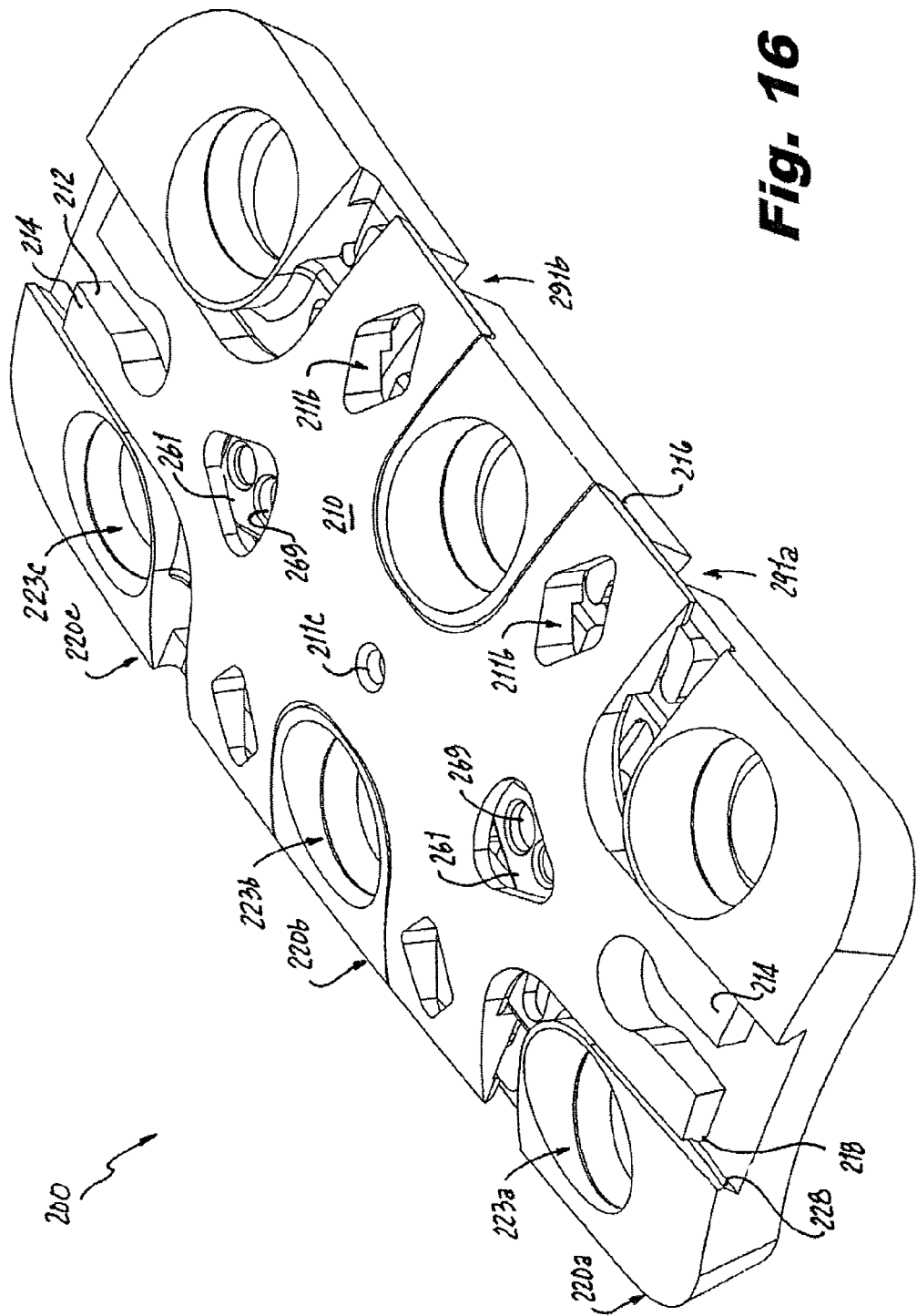

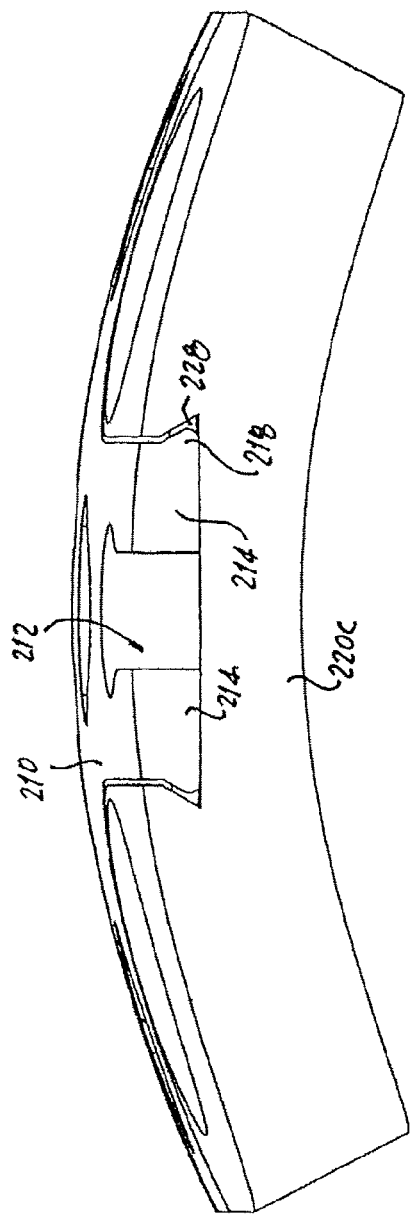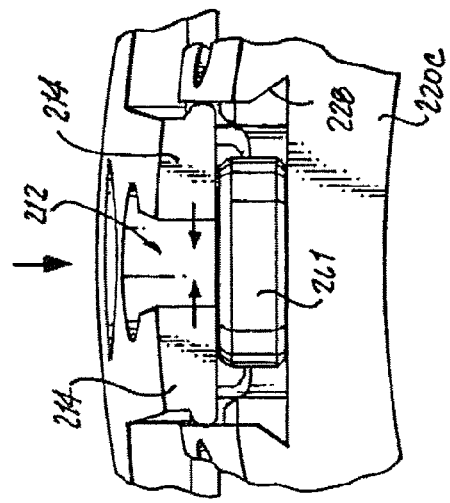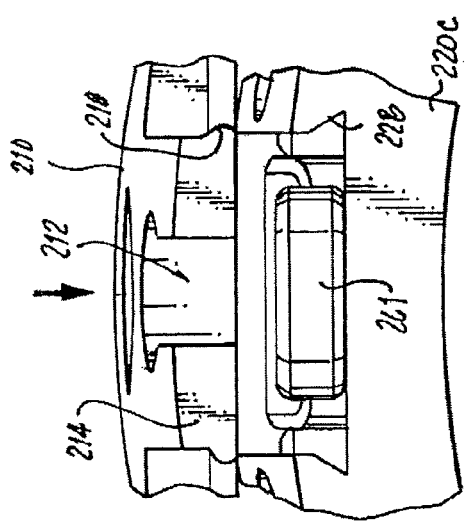

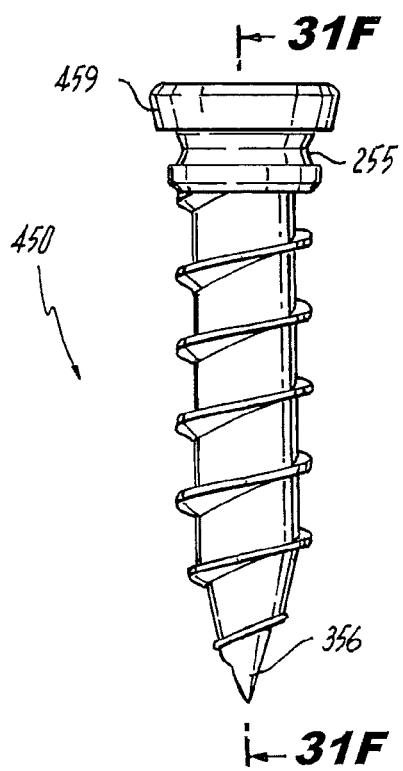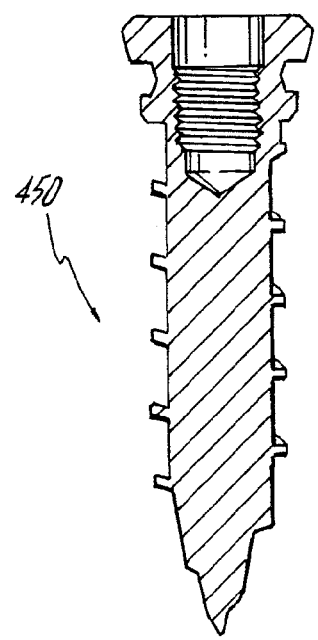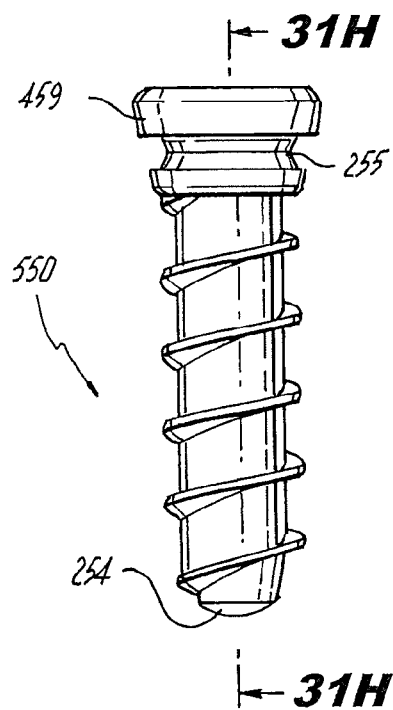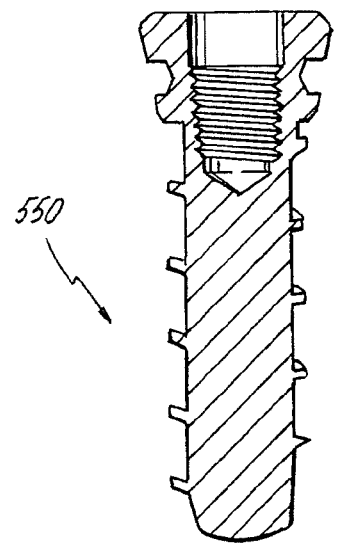
Fig. 31E   Fig. 31F
Fig. 31G   Fig. 31H

DYNAMIC VERTEBRAL COLUMN PLATE SYSTEM

CROSS-REFERENCE TO RELATED APPLICATIONS

This application claims the benefit of priority to U.S. Patent Application Ser. No. 61/160,154, filed Mar. 13, 2009, which application is incorporated herein by reference, in its entirety.

FIELD OF THE INVENTION

The present invention relates to implantable orthopedic appliances. Particularly, the present invention is directed to a plate system for use in supporting a section of the vertebral column to facilitate spinal fusion following surgery.

BACKGROUND

A variety of implantable orthopaedic devices are known in the art for assisting recovery following trauma or injury. Of such devices, many are directed to relatively rigid devices that force substantial load transfer from the anatomical structure, for example, from the vertebral column. Applicant recognizes that such load transfer inhibits desirable loading of the anatomical structure. In the case of bony tissue, insufficient loading will inhibit, reduce or prevent ossification of the structure, the concept of which is described by and known as "Wolff's Law."

Accordingly, Applicant recognizes that it is desirable to provide orthopaedic appliances that provide for controlled load sharing, while providing support necessary to prevent damage to a bone graft and/or other anatomical structure, to allow for healing. Applicant also recognizes that it is desirable to provide orthopaedic appliances that are versatile and can provide adaptability to a variety of situations. Applicant further recognizes that it is desirable to provide a least one locking feature to inhibit unintentional backing out of fasteners, such as bone screws. The present invention provides solutions for the foregoing.

SUMMARY OF THE INVENTION

In accordance with one aspect of the invention, a vertebral column construct for stabilizing a segment of a vertebral column is provided, having a first plate segment, a second plate segment connected to the first plate segment, and a spring connected between adjacent plate segments. An engagement member connected between the first and second plate segments can also be provided. Alternatively, the separate engagement member can be omitted if sufficient stability is otherwise provided, such as by the spring or another element.

The spring can be adapted and configured to provide a predetermined preload between the first and second plate segments. Accordingly, the spring can be shaped, dimensioned and formed from a material appropriate to achieve the predetermined preload, in combination with other components of the construct. Such a preload can advantageously enhance fusion across a bone graft Alternatively, the spring can be adapted and configured to resist, by a predetermined degree, loading between the first and second plate segments.

A cam can be provided on one of the first and second plate segments, and be moveable between engagement with cam surface in connection with the other of the first and second plate segments, and disengagement therefrom, wherein engagement between the cam and the cam surface prevents dynamic loading of the spinal segment, between the first and second plates.

The cam can be configured such that the position of the cam determines whether the preload exerted by the spring is transferred through the construct or transferred to the segment of the vertebral column to which the construct is attached.

The cam can be adapted and configured to adjust preload applied between segments, by adjusting tension in the spring.

The spring can be an arcuately bent rod or bar. The spring can be made from a shape memory alloy.

The spring can be engaged with grooves in one of the plate segments, the grooves being configured such that outward application of force by the spring is resolved as a net axial contractive force between the first and second plate segments.

A common upper plate can be provided, and connected to the first and second plate segments. The upper plate and at least one of the first and second plate segments can be adapted and configured for a substantially linearly translatable connection therebetween. The upper plate and slideably connected bottom plate segment can be connected by a mechanical interlock. The mechanical interlock can include a dovetail or a pin and slot configuration.

A third plate segment can be provided and connected to at least one of the first and second plate segments by a spring, and optionally an engagement member. Fourth, fifth, sixth and subsequent plate segments can also be provided.

In accordance with the invention, at least two plate segments can be provided, and the construct can be adapted and configured such that a connection spanned between first and second plate segments is selectable between static and dynamic configurations.

In accordance with the invention, at least three plate segments can be provided, spanning two connections, respectively, and the construct can be adapted and configured such that each of the two connections spanned is selectable between static and dynamic configurations.

In accordance with another aspect of the invention, a vertebral column plate system construct for stabilizing a segment of a vertebral column is provided having a first plate segment, a second plate segment connected to the first plate segment, a spring element connected between adjacent plate segments, adapted and configured for providing a predetermined preload between adjacent plate segments, to enhance spinal fusion, an upper plate connected to the first and second plate segments, and a cam provided on one of the first and second plate segments, moveable between engagement with cam surface in connection with the other of the first and second plate segments, and disengagement therefrom, wherein engagement between the cam and the cam surface prevents dynamic loading of the spinal segment, between the first and second plates. Further, an engagement member connected between adjacent plate segments can be provided.

In accordance with the invention, the cam surface can be provided on the other of the first and second plates. Alternatively, the cam surface can be on the upper plate. In such an arrangement, the upper plate and the other of the first and second plates can be substantially rigidly connected to one another.

In accordance with a further aspect of the invention, a method of implanting a vertebral column construct on a spinal segment is provided, the method including, in any order, securing each of a plurality of plates of the construct to respective vertebrae, determining whether to apply a preload between first and second levels of vertebrae, and applying a first preload between said first and second levels of vertebrae.

The step of applying the first preload can include rotating a first cam of the dynamic vertebral column construct in a first direction.

The method can further include the steps of evaluating efficacy of the first preload, and applying a second preload, in place of the first preload, between said first and second levels of vertebrae, the second preload being different from the first preload. The second preload being greater than the first preload. Alternatively, the second preload can be less than the first preload.

The step of applying a second preload can include rotating a first cam in a second direction, different from the first direction.

The method can further include the steps of determining whether to apply a preload between first and second levels of vertebrae, and applying a third preload between said second and third levels of vertebrae.

The step of applying the third preload can include rotating a second cam of the dynamic vertebral column construct in a first direction.

The method can further comprising the steps of evaluating efficacy of the third preload, and applying a fourth preload, in place of the third preload, between said second and third levels of vertebrae, the fourth preload being different from the third preload.

The step of applying the fourth preload can include rotating a second cam in a second direction, different from the first direction.

Constructs in accordance with the invention, additionally or alternatively, can be configured to provide a predetermined amount of resistance to contraction and/or to bending between adjacent plate segments thereby allowing for a predetermined amount of load sharing between the construct and the vertebral column segment.

In accordance with the invention, the engagement members, if provided, can be symmetrically arranged in the construct with respect to a longitudinal axis thereof. Moreover, two laterally opposed, springs can be provided in the construct and can be arranged substantially symmetrically with respect to a longitudinal axis of the construct.

In accordance with the invention, a plurality of screws can be provided for engaging the construct to the vertebral column segment. The screws can include a slot or other feature for accepting an engagement element for inhibiting unintentional backout of the screws.

In accordance with the invention, one or more of the plate segments can be embodied so as to include respective upper and lower portions.

A plurality of spring elements can be provided for assembly with plate segments, the spring elements being provided in a range of stiffnesses, allowing for selectability of contractive force, or preload, of the construct and/or selectability of resistance to contraction, and/or bending stiffness of the construct, if so-embodied.

The engaging element can be received in a corresponding recess provided in each plate segment connected by the engagement member.

It is to be understood that both the foregoing general description and the following detailed description are exemplary and are intended to provide further explanation of the invention claimed.

BRIEF DESCRIPTION OF THE DRAWINGS

The accompanying drawings, which are incorporated in and constitute part of this specification, are included to illustrate and provide a further understanding of the systems, devices, kits and related methods of the invention. Together with the description, the drawings serve to explain the principles of the invention, wherein:

FIGS. 1A and 1B are, respectively, an isometric line drawing and an isometric rendering showing internal structure, of a representative embodiment of a dynamic vertebral column plate system and accompanying screws, in accordance with the present invention, wherein the vertebral column plate system is shown in an extended state;

FIG. 15E is a left side view of the spring member of FIG. 15A;

FIG. 15F is a right side view of the spring member of FIG. 15A;

FIGS. 16-29 illustrate various views of another exemplary embodiment of a dynamic vertebral column plate system in accordance with the invention, having arcuately bent rod or bar-shaped springs and an integral cam element;

FIG. 16 is an isometric view of the plate construct in accordance with this embodiment, shown in an expanded condition;

FIG. 17 is a side view of the plate construct, shown in an expanded condition;

FIG. 18 is an isometric view of the plate construct, shown in a contracted condition;

FIG. 19 is a side view of the plate construct, shown in a contracted condition;

FIG. 20 is a bottom isometric view of the plate construct, shown in an expanded condition;

FIG. 21 is a bottom isometric view of the plate construct, shown in a contracted condition;

FIG. 22A-C are end views of the plate construct, illustrating engaging steps between an upper plate and a lower end plate segment;

FIG. 23 is a partly exploded isometric view of the plate construct, illustrating internal components thereof and a tool for operating a cam thereof;

FIG. 24 is a bottom isometric of the upper plate of plate construct;

FIG. 25 is an exploded view of the internal components of the plate construct;

FIG. 26 is an isometric view of the plate construct, shown in an expanded condition with both cams rotated out of engagement with opposing recesses therefor, shown with the upper plate removed for visibility;

FIG. 27 is top view of an end portion of the plate construct with the illustrated cam held in an opposing recess, maintaining the expanded condition of the plate, shown with the upper plate removed for visibility;

FIG. 28 is an isometric view of the plate construct with both cams rotated out of engagement with the opposing recesses therefor, shown in a contracted condition, with the upper plate removed for visibility;

FIG. 29 is top view of an end portion of the plate construct with the illustrated cam rotated out of engagement with the opposing recesses therefor, maintaining the expanded condition of the plate, shown in a contracted condition, with the upper plate removed for visibility;

FIG. 30A illustrates the construct during insertion of a final screw for engaging the attached vertebral segment;

FIG. 30B illustrates the construct during rotation of a cam thereof, with a tool therefor;

FIG. 30C illustrates the construct following attachment to the vertebral segment and rotation of both cams from the opposing recesses therefor, shown with the upper plate removed for visibility;

FIGS. 31A-H are side and cross-sectional views of various screw configurations for use with the dynamic vertebral column plate systems of the invention;

FIG. 33 is an isometric view of the construct of this embodiment, shown in an expanded condition;

FIG. 34 is an isometric view of the construct of this embodiment, shown in a contracted condition;

FIG. 35 is an isometric view of the construct of this embodiment, shown in an expanded condition, with the upper plate removed for visibility;

FIG. 36 is a bottom isometric view of the upper plate of this embodiment of the construct;

FIG. 37 is a top view of the construct of this embodiment shown in an expanded condition, with the upper plate removed for visibility;

FIG. 38 is a top view of the construct of this embodiment shown in a contracted condition, with the cams in one position for applying a corresponding preload to a spinal segment, and with the upper plate removed for visibility; and FIG. 39 is a top view of the construct of this embodiment shown in a contracted condition with the cams in another position (as compared with FIG. 38), for applying a different corresponding preload to a spinal segment, also shown with the upper plate removed for visibility.

DETAILED DESCRIPTION

Figure 1C:
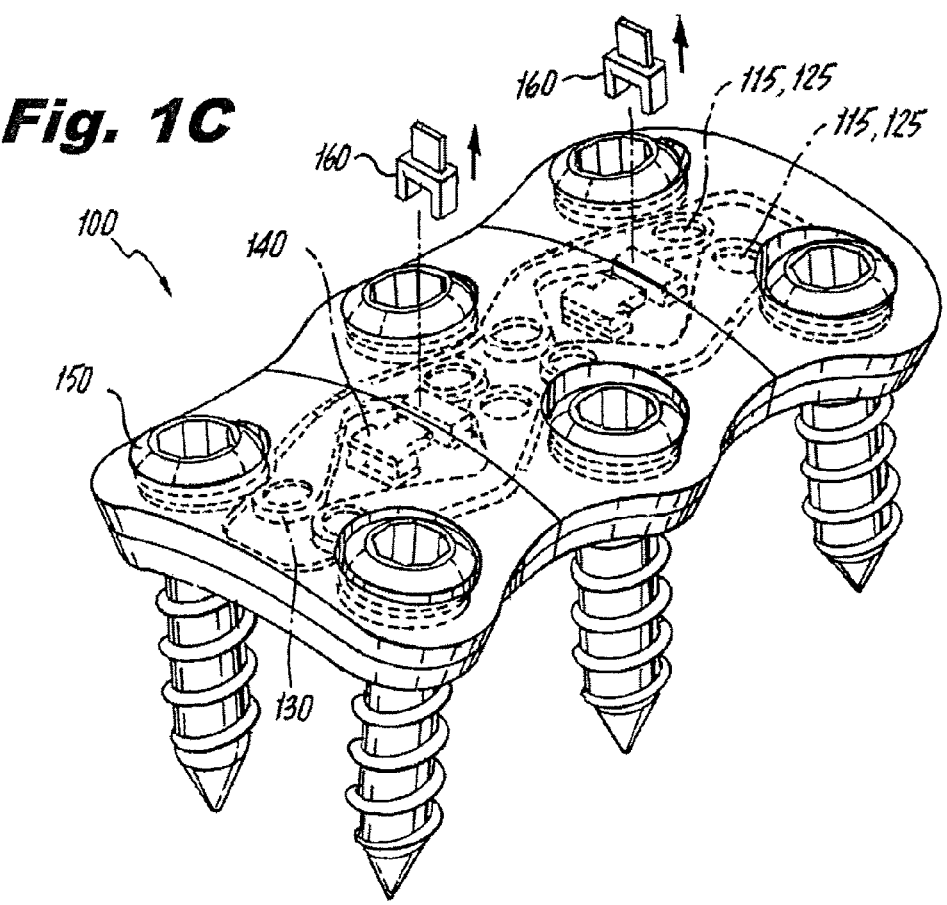
FIGS. 1C and 1D are, respectively, an isometric rendering showing internal structure and an isometric line drawing of a representative embodiment of a dynamic vertebral column plate system and accompanying screws, in accordance with the present invention, wherein the vertebral column plate system is shown in a collapsed state.
Figure 1D:
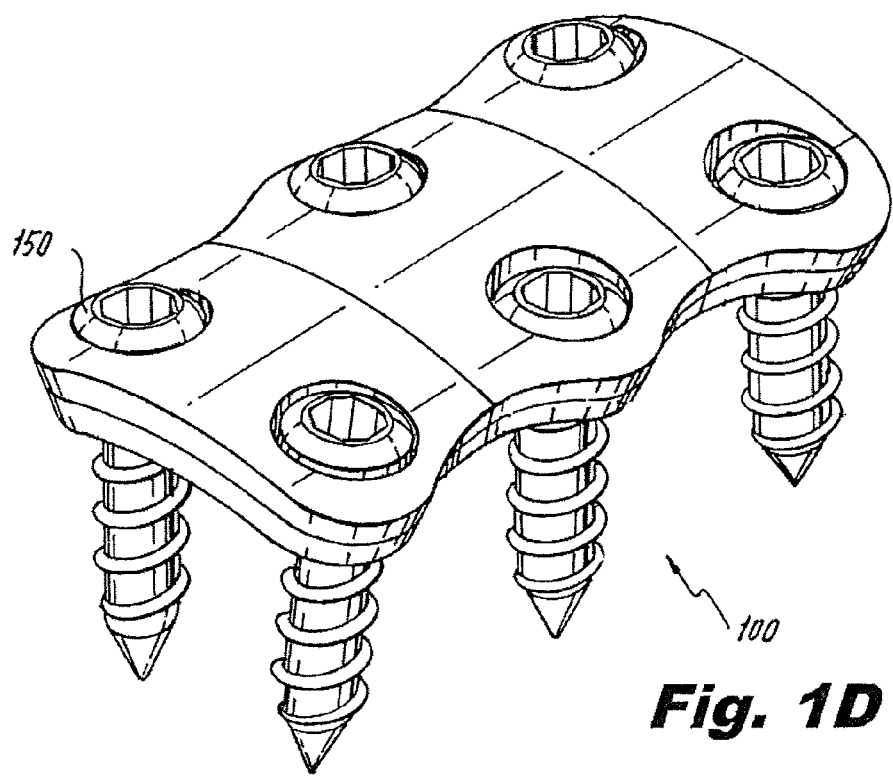

Reference will now be made in detail to preferred embodiments of the invention, an example of which is illustrated in the accompanying drawings.

The devices and methods presented herein may be used for stabilization of a segment of the vertebral column during spinal fusion following surgery.

With reference to the figures and as seen, for example, in FIGS. 1A and 1B, a dynamic vertebral column plate system for stabilizing a segment of a vertebral column is assembleable into a plate construct 100 for attachment to a vertebral column segment. Such constructs can be provided to a user (such as a surgeon) already assembled, or can be assembled by the user, for example. The plate system includes a first end plate segment, having upper and lower portions 110a and 120a, a second end plate segment having upper and lower portions 110c and 120c connected to and arranged opposite the first plate segment. As illustrated, an intermediate plate segment having upper and lower portions 110b and 120b can be provided. In accordance with further aspects of the invention, additional intermediate plate segments can additionally be provided, yielding a total of 3, 4, 5, 6, 7, 8 or more plate segments in the construct 100 formed from the components of the subject system.

In the illustrated embodiment, an engagement member 140 and spring elements 130 are provided between and connect adjacent plate segments, forming the plate construct 100. Although one engagement member 140 and two springs 130 are illustrated between each adjacent pair of plate segments, it is to be understood that any suitable number of such elements can be provided. It is particularly conceived that two laterally opposed engagement members 140 can be additionally or alternatively provided laterally distal to the springs 130. In such an embodiment, it is conceived that it may prove necessary to provide additional material along the lateral edges of the plate segments 110, 120 to provide structural support and/or simply to provide space for holding the additional engagement members.

The springs 130 are adapted and configured to provide a predetermined amount of contractive force, or preload, of the construct 100. In accordance with alternate embodiments the springs 130 can be adapted and configured to provide a predetermined amount of bending stiffness between adjacent plate segments, thereby allowing for a predetermined amount of load sharing between the construct 100 and the vertebral column segment to which it is attached.

Figure 11A:
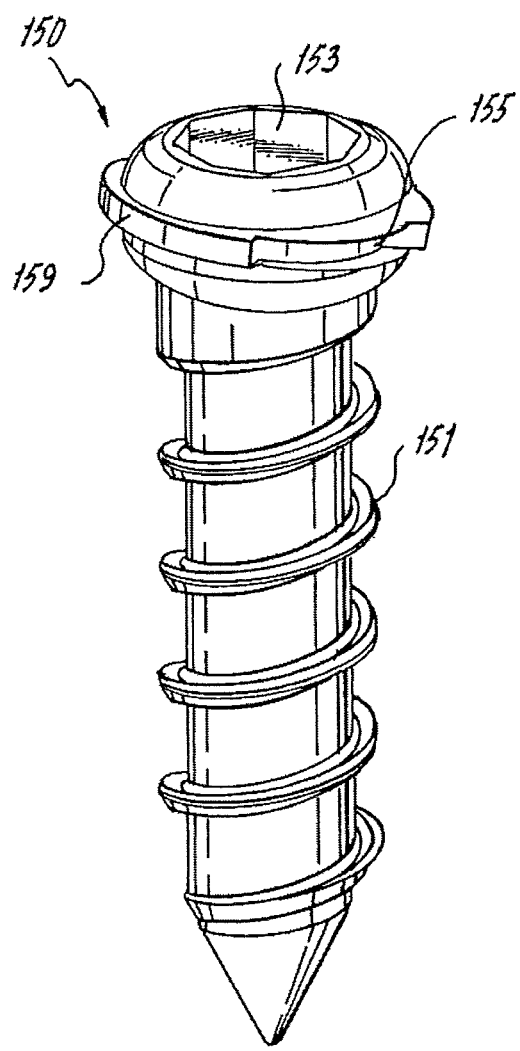
FIGS. 11A and 11B are, respectively, a line drawing and a rendering illustrating a screw and a retaining clip in accordance with the invention for use with the dynamic vertebral column plate system of FIGS. 1A and 1B.
Figure 11B:
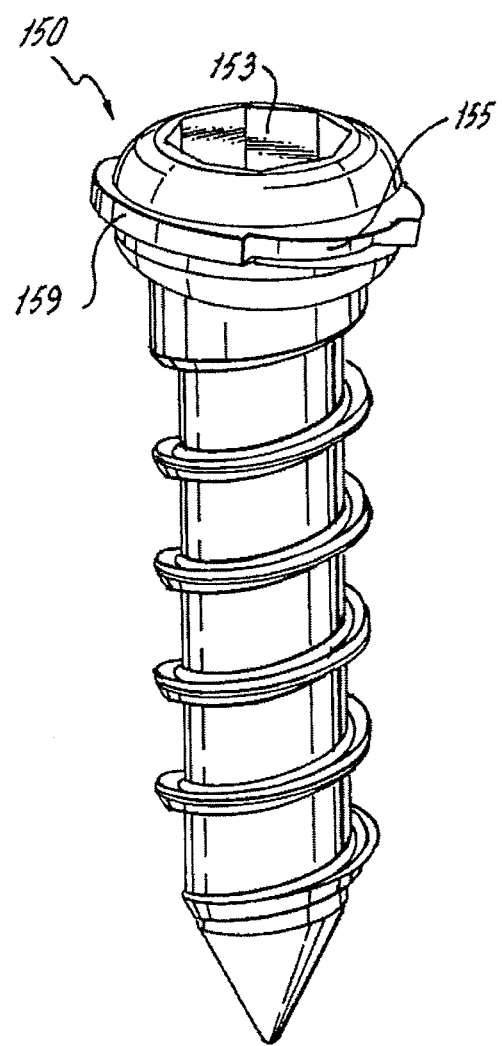
Figure 11C:
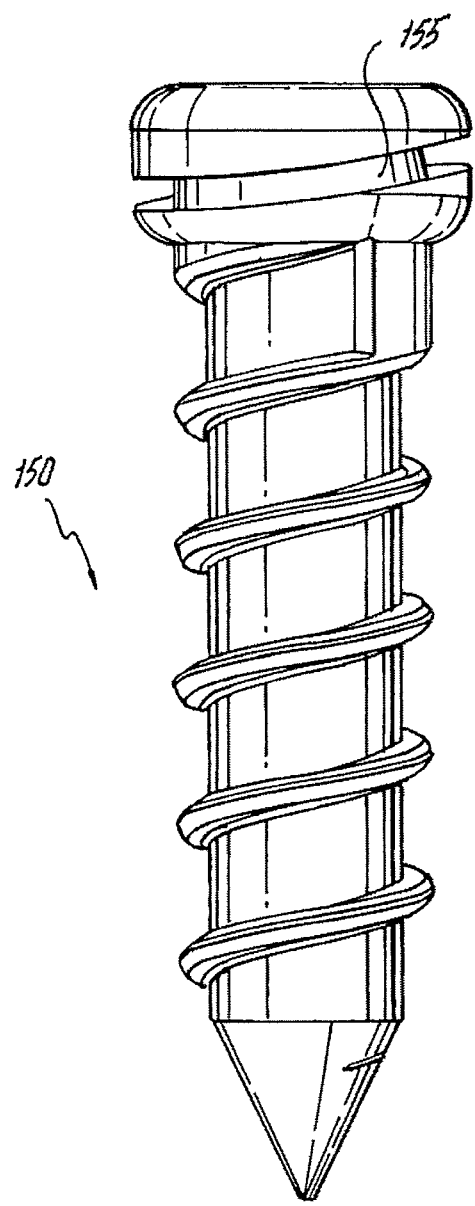
FIG. 11C is a line drawing of the screw of FIGS. 11A and 11B, shown without the retaining clip.

As can be seen in FIGS. 1A and 1B, a plurality of screws 150 are provided for anchoring the construct 100 into the bone. An aperture 113*a-c* is provided in each upper plate portion 110*a*, 110*b*, 110*c*, in which the head of the screws 150 rest. A groove 155 is provided in the head of the screw 150 for receiving a locking element, such as the retaining clip 159, which is best seen in FIGS. 11A and 11B. The locking element can be any suitable element, including but not limited to a resilient o-ring, circlip, or another suitable element, such as a latching toroidal coil available from Bal Seal Engineering, Inc. of Foothill Ranch, Calif., USA. The locking element can be formed of any suitable material, such as a metal, metal alloys, an elastomeric material, silicone, polychloroprene (e.g. Neoprene), or a plastic material such as polyetheretherketone (PEEK), for example. The locking element, carried by the screw can seat in a groove provided in the construct being used.

As seen in FIG. 1B, as well as in FIGS. 1C, 8B, 9 and 10, spring engagement members or bosses 115, 125 can be provided in connection with or integrally with the plate segments, such as with upper plate portion 110*a* or lower plate portion 120*a*, respectively, for engaging the springs 130. Similarly, the engagement members 140 are secured to adjacent plates by a recess 117, 127 provided in each respective upper plate portion 110*a-c* and lower plate portion 120*a-c*. The recesses 117, 127 are shaped with a corresponding partial "I" shape to capture the engagement members 140, and to allow for axial motion between the plate portions 110, 120 and the engagement members 140. Accordingly, the transverse section of the recess 117, 127 can be deeper than that of the engagement member 140 to allow for axial motion. Moreover, it is to be understood that various shapes of engagement members 140 can be used, and are not be limited solely to the shape illustrated.

Although illustrated as independent components, it is to be understood that in alternative embodiments, engagement members 140 can be integrally formed with one plate, fitting into a corresponding recess 117, 127 in an adjacent plate. Accordingly, relative motion between plate segments is allowed, without necessitating manufacture and assembly of separate components. In line with such embodiments, it is particularly conceived that any permutation of arrangements of separate or integral engagement members 140 is possible, with any suitable number of engagement members 140 being provided between adjacent plates.

The round spring engagement members or bosses 115, 125 allow for relative movement of the springs when the construct 100 is subjected to different loading conditions, such as axial tensile or compressive forces or lateral bending (in a plane that is substantially parallel to the plate surface and parallel to the longitudinal axis of the construct, for example). Alternatively, the bosses 115, 125 can be any suitable shape, including but not limited to elliptical, oblong, polygonal (e.g., square, hexagonal). Shapes of bosses 115, 125 that inhibit rotation thereabout can enhance lateral stability of the construct 100. A relatively shallow recess 119 is provided in one or more of the upper plate portions 110*a-c* and lower plate portions 120*a-c*. The recesses 119 are configured to provide room for elastic deformation of the springs 130 under the aforementioned axial compression and/or bending conditions.

Upper and lower portions of the plate segments, such as upper plate portion 110*a* and lower plate portion 120*a*, can be mutually secured in any suitable manner, including but not limited to welding, mechanical fasteners, solders, adhesives, epoxy materials, mechanical interlock features or the like.

Figure 2A:
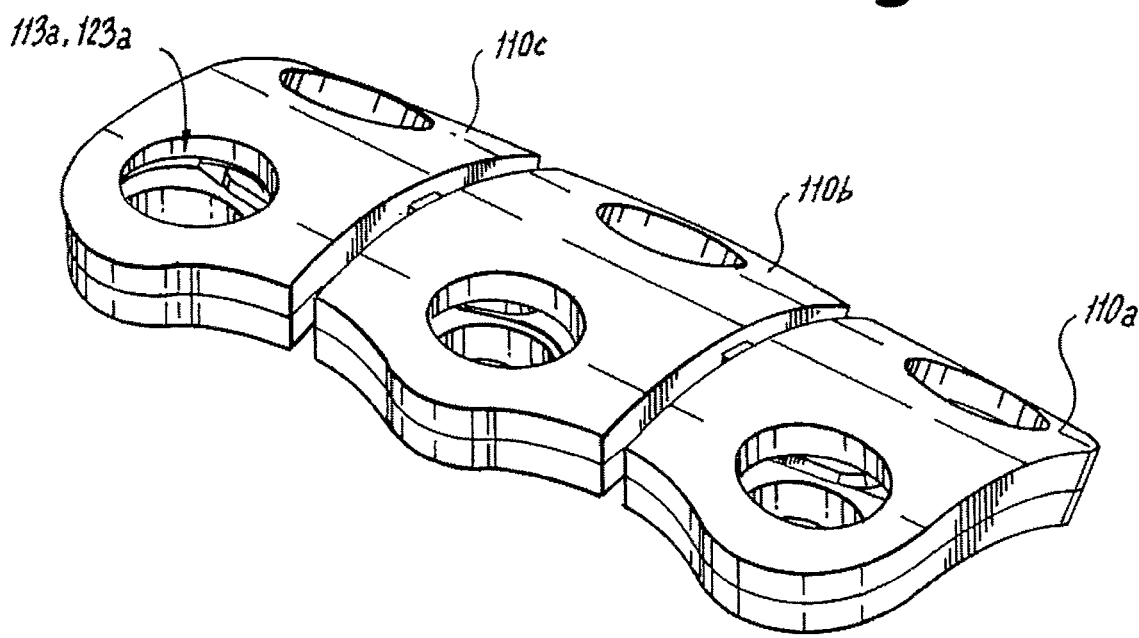
FIGS. 2A and 2B are, respectively, an isometric line drawing and an isometric rendering showing internal structure, of the dynamic vertebral column plate system of FIGS. 1A and 1B, shown without accompanying screws, in accordance with the present invention.
Figure 2B:
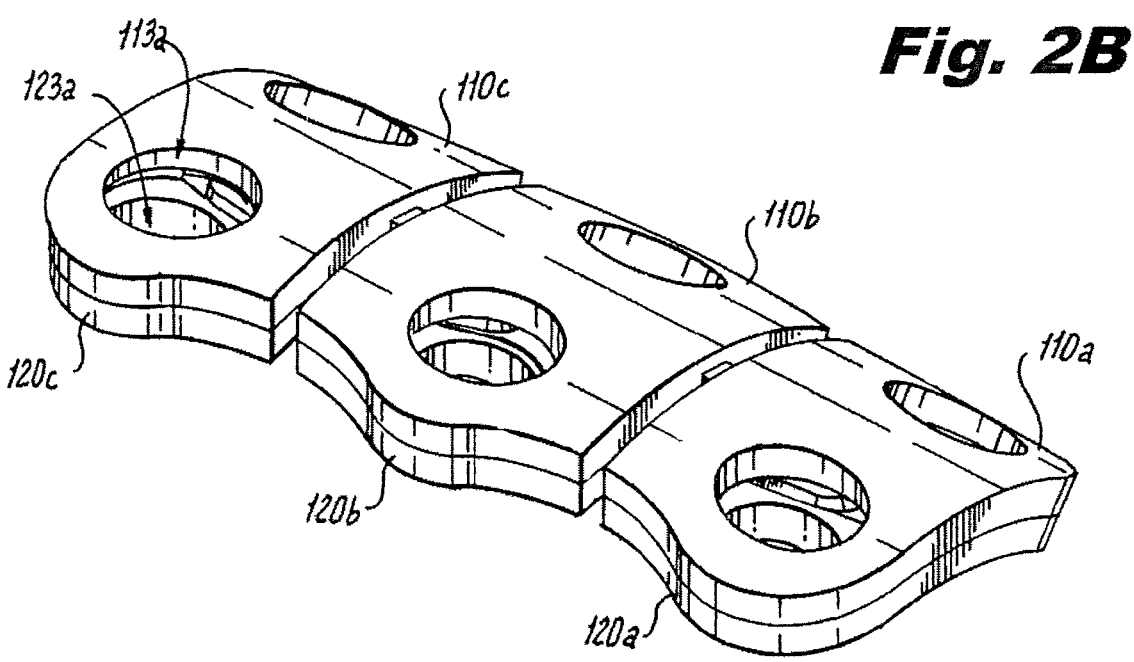
Figure 3A:
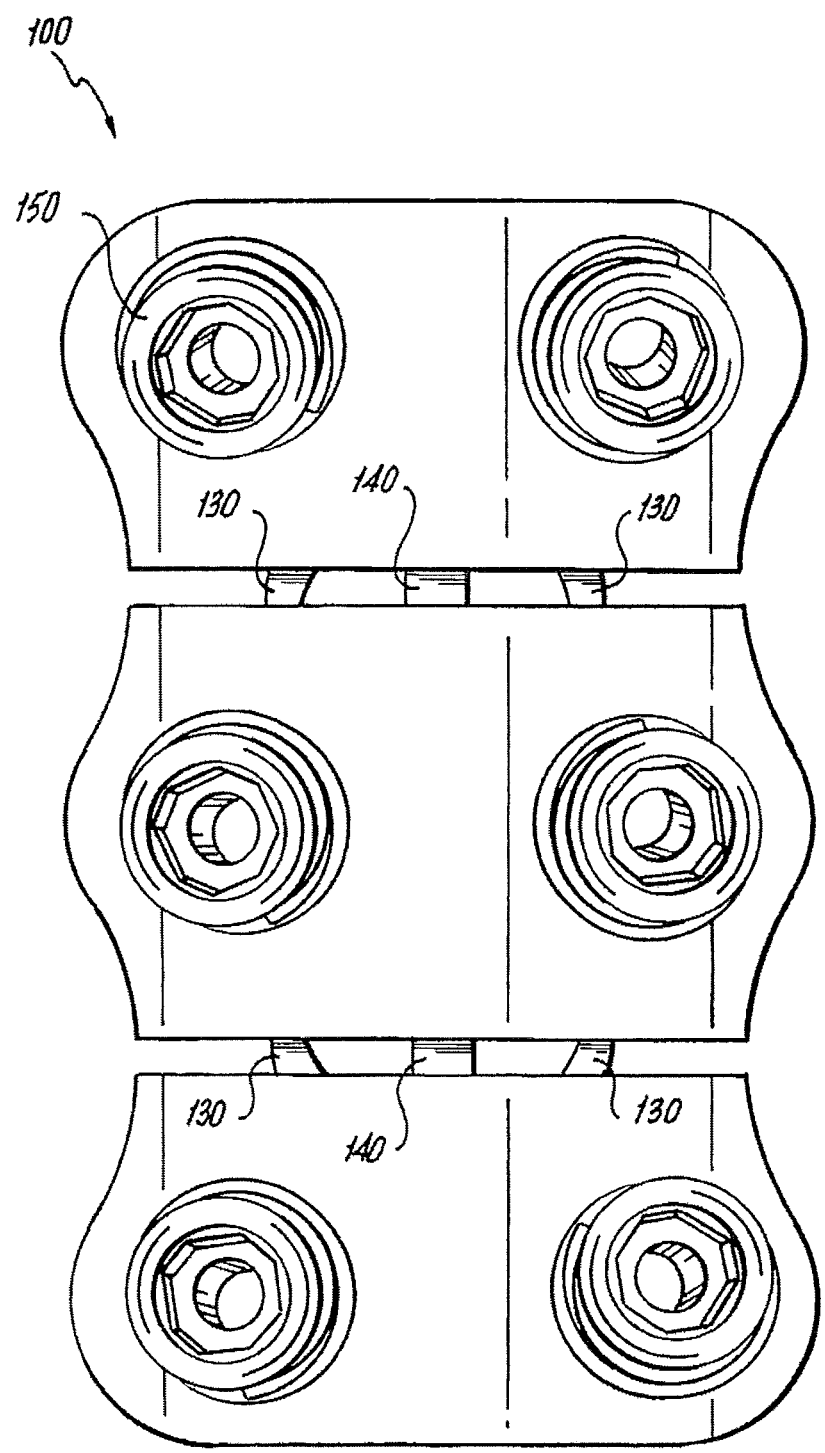
FIGS. 3A and 3B are, respectively, a top line drawing and a top rendering showing internal structure, of the dynamic vertebral column plate system of FIGS. 1A and 1B, shown with accompanying screws.
Figure 3B:
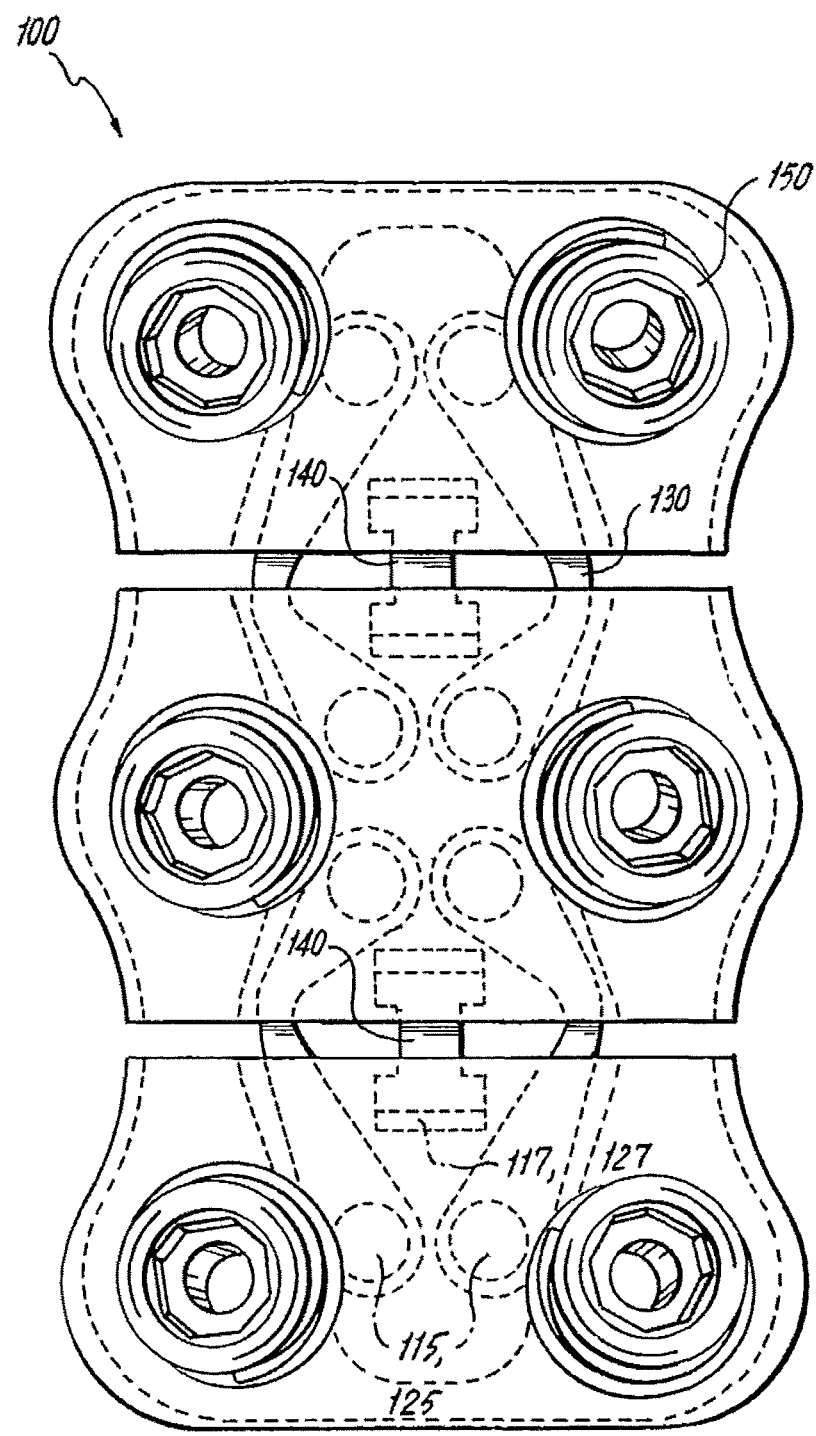
Figure 3C:
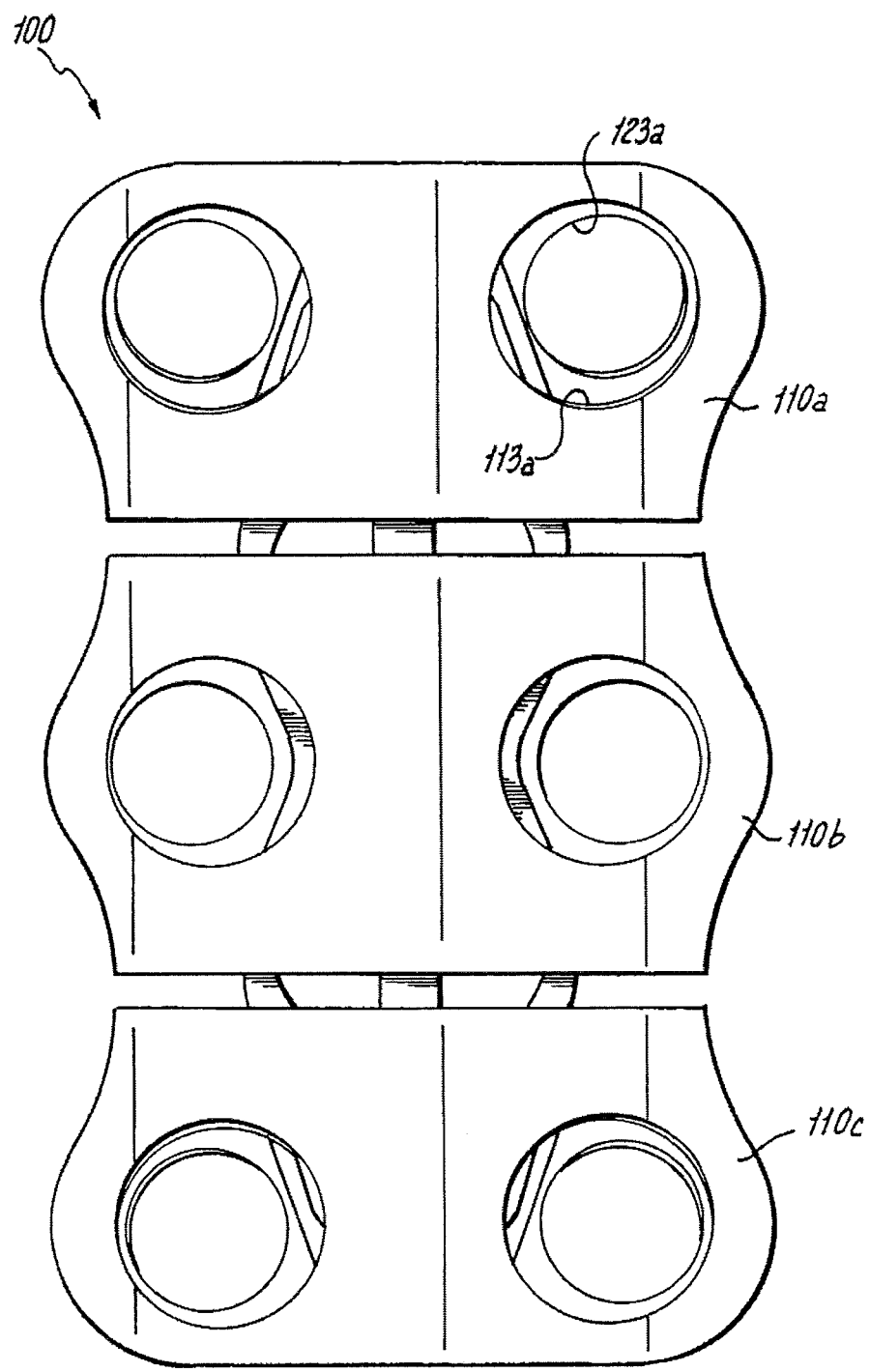
FIG. 3C is a top line drawing of the dynamic vertebral column plate system of FIGS. 1A and 1B, shown without the accompanying screws.
Figure 4A:
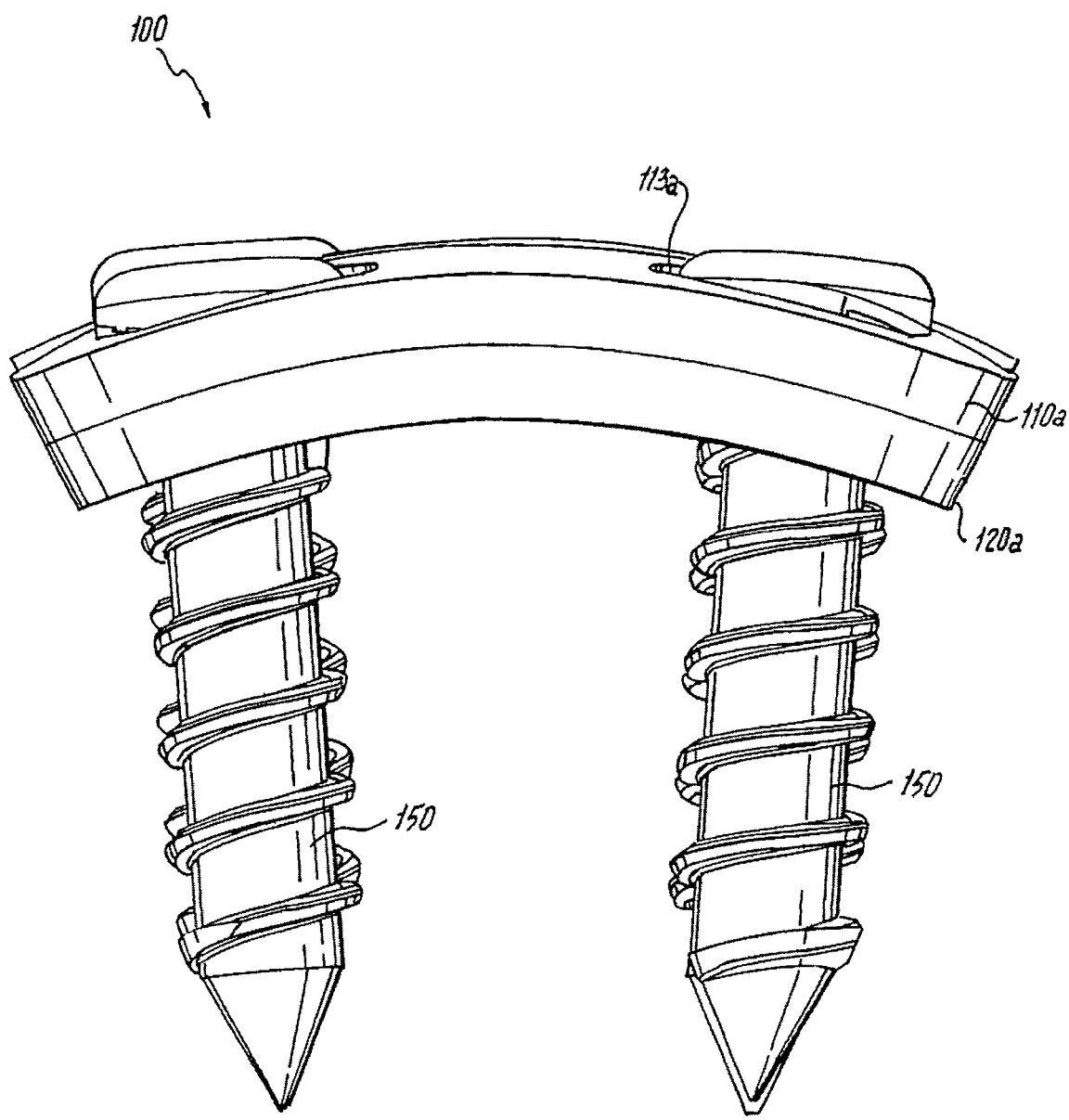
FIGS. 4A and 4B are, respectively, an end line drawing and an end rendering showing internal structure of the dynamic vertebral column plate system of FIGS. 1A and 1B, shown with accompanying screws.
Figure 4B:
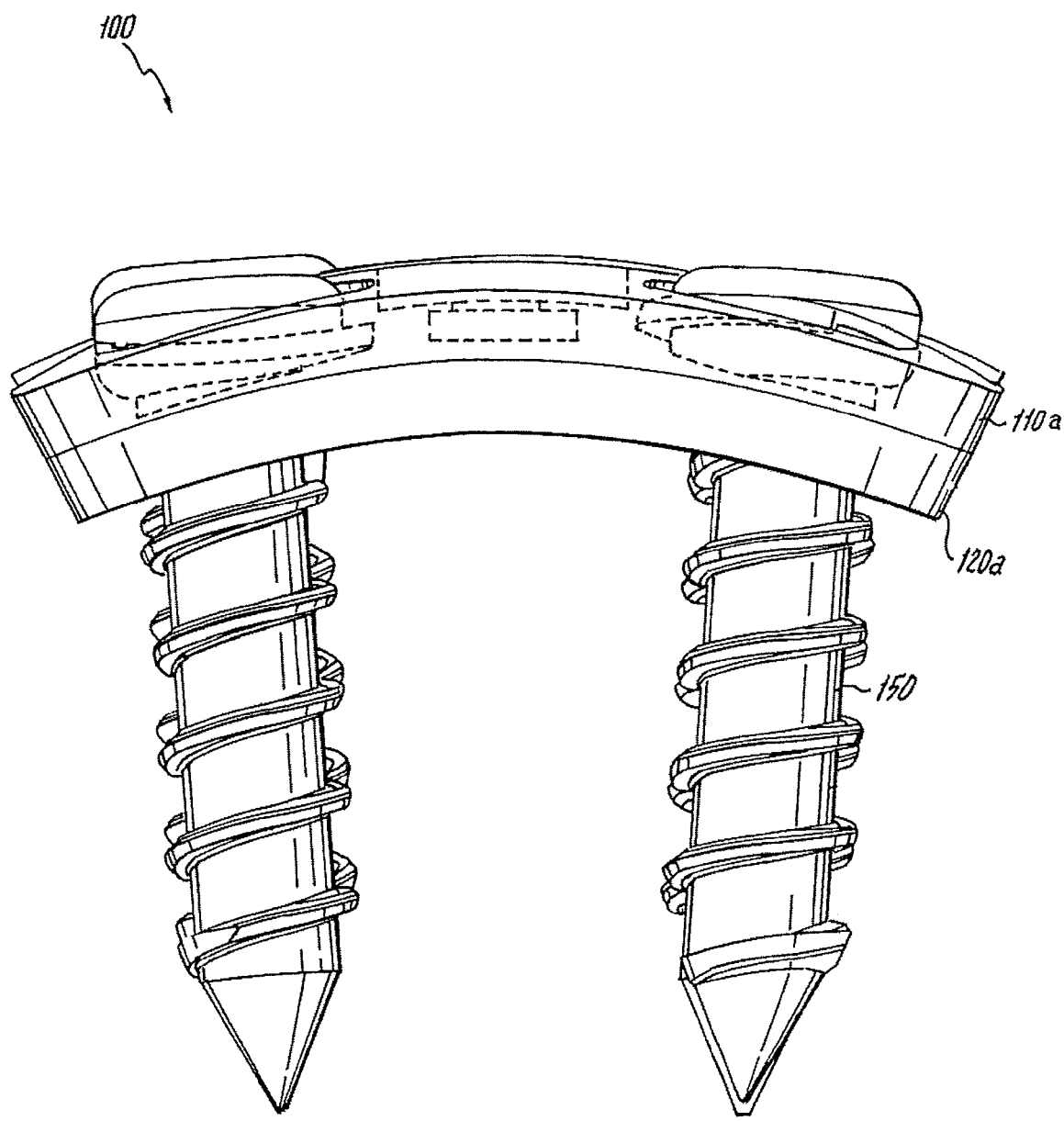
Figure 5A:
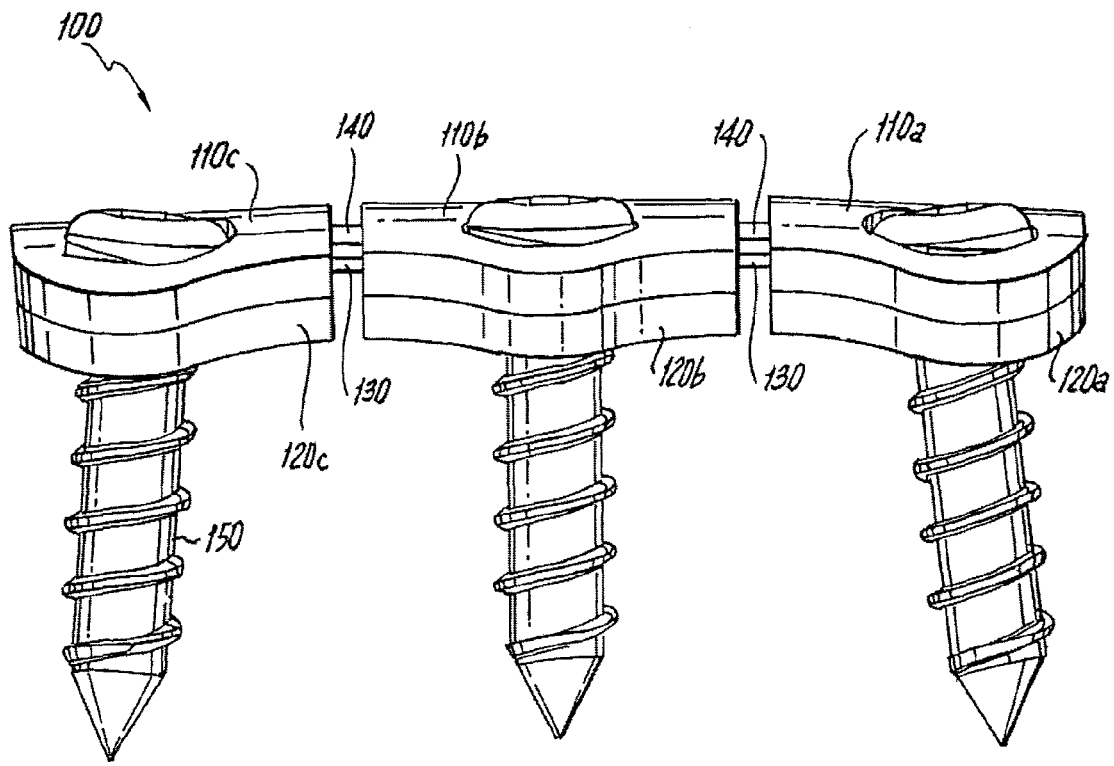
FIGS. 5A and 5B are, respectively, a side line drawing and a side rendering showing internal structure, of the dynamic vertebral column plate system of FIGS. 1A and 1B, shown with accompanying screws.
Figure 5B:
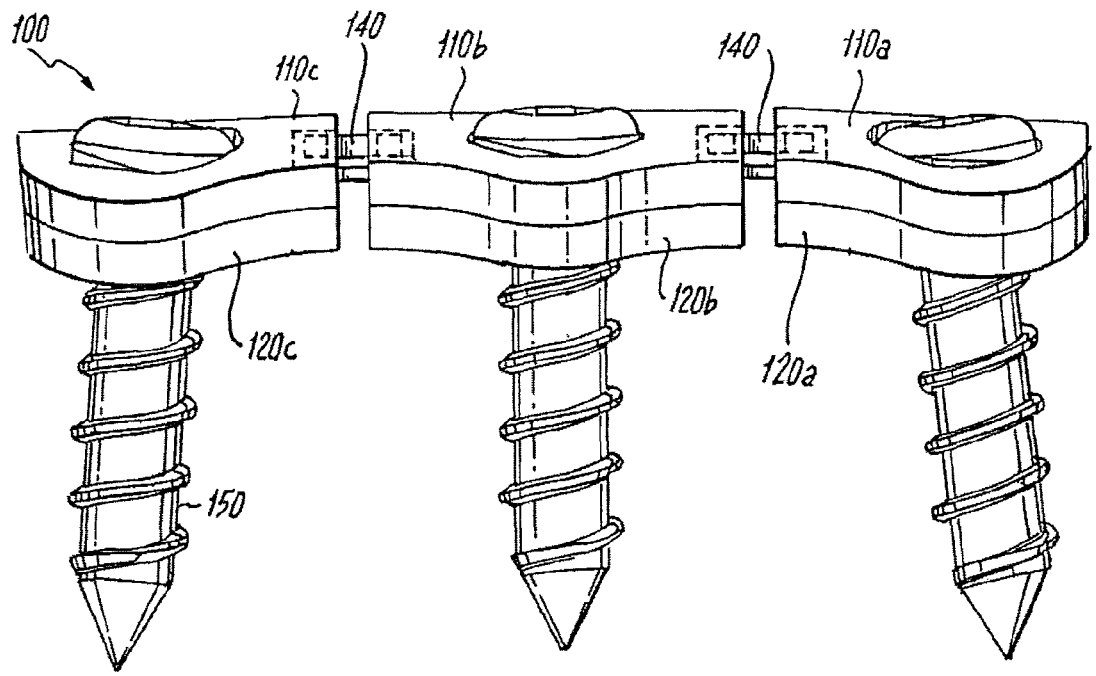
Figure 6A:
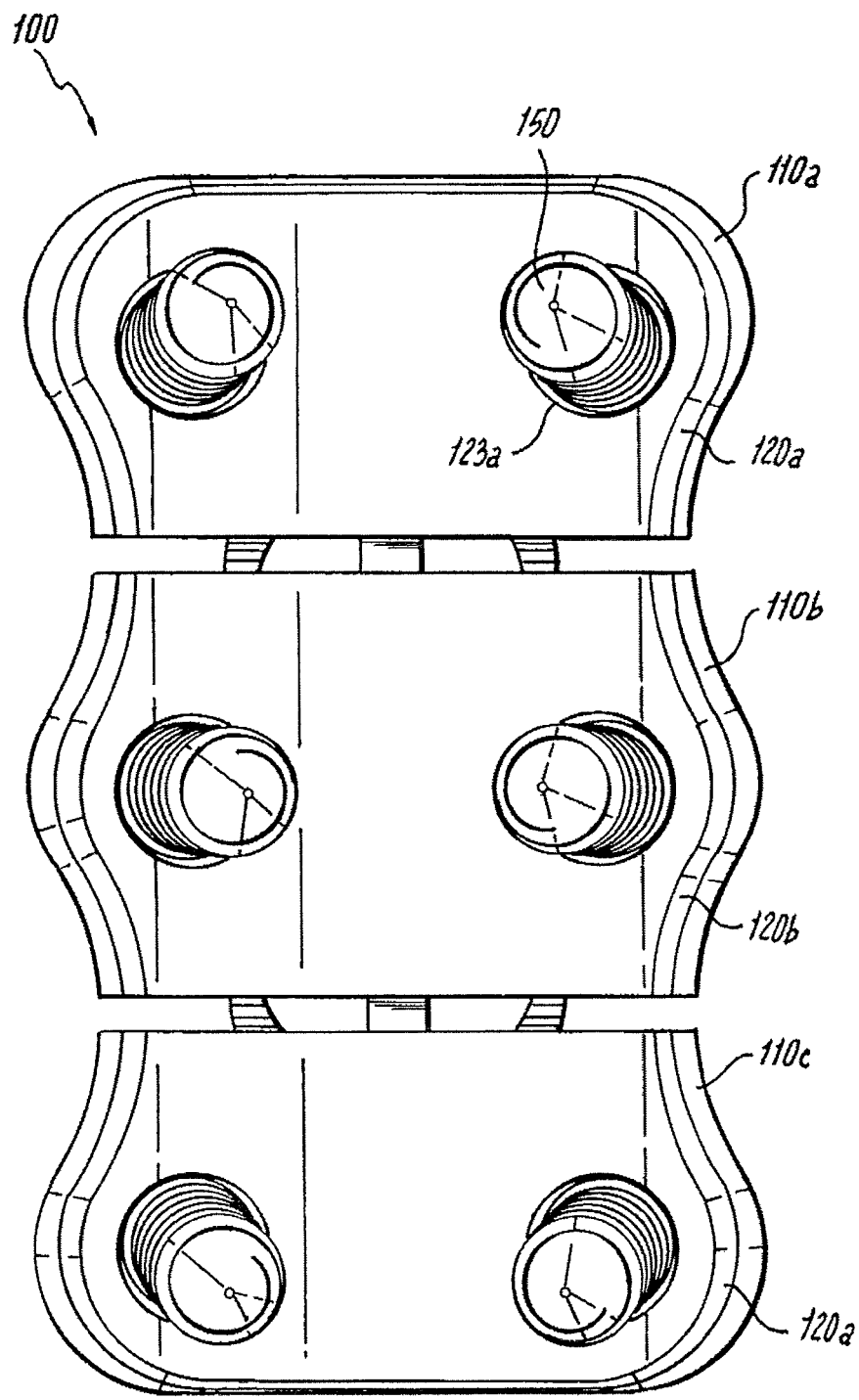
FIG. 6A is a bottom line drawing of the dynamic vertebral column plate system of FIGS. 1A and 1B, shown with accompanying screws.
Figure 6B:
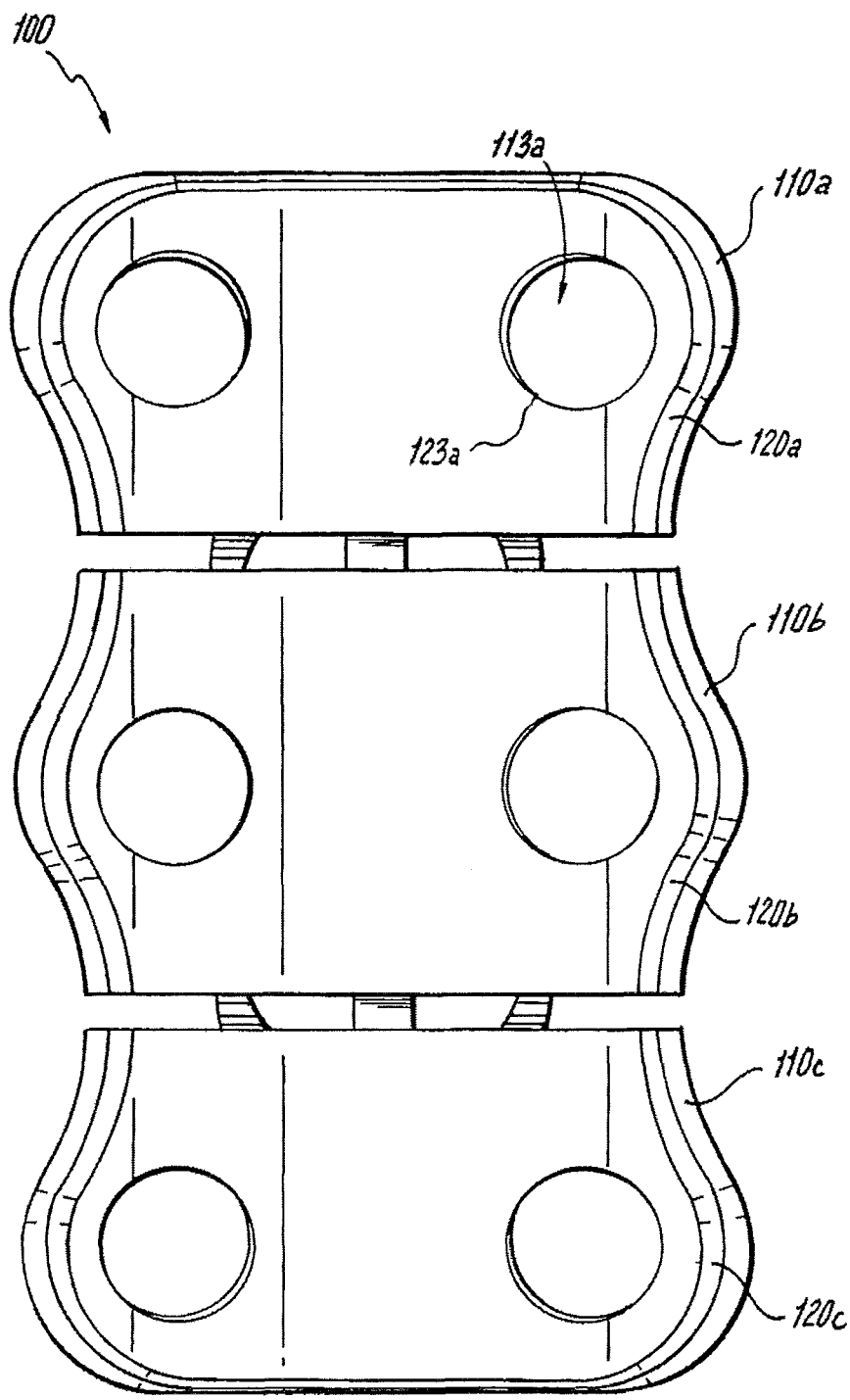
FIG. 6B is a bottom line drawing of the dynamic vertebral column plate system of FIGS. 1A and 1B, shown without the accompanying screws.
Figure 7A:
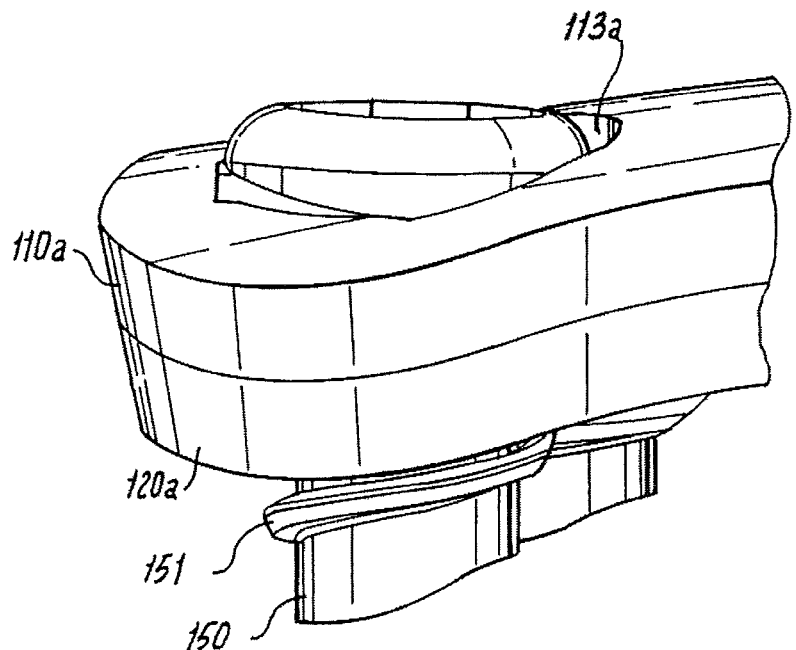
FIGS. 7A and 7B are, respectively, a line drawing and a rendering illustrating a detail view of a portion of the dynamic vertebral column plate system of FIGS. 1A and 1B, shown with an accompanying screw.
Figure 7B:
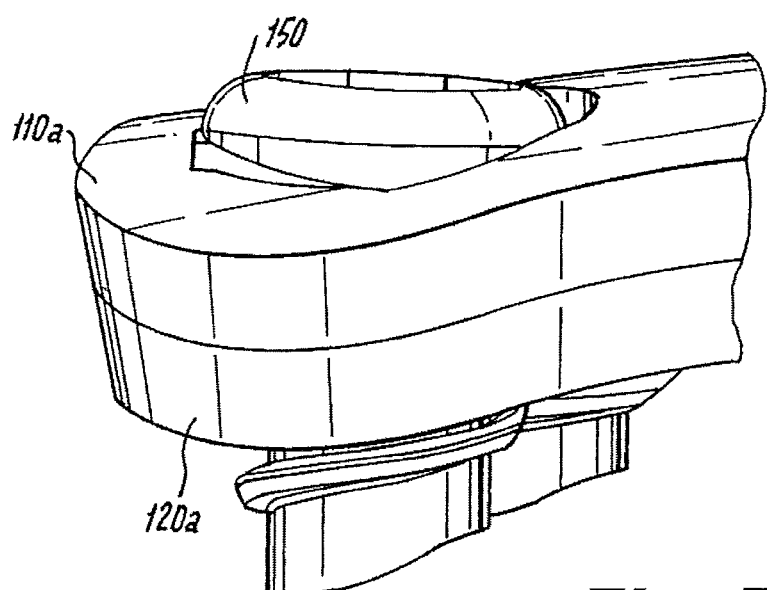
Figure 8A:
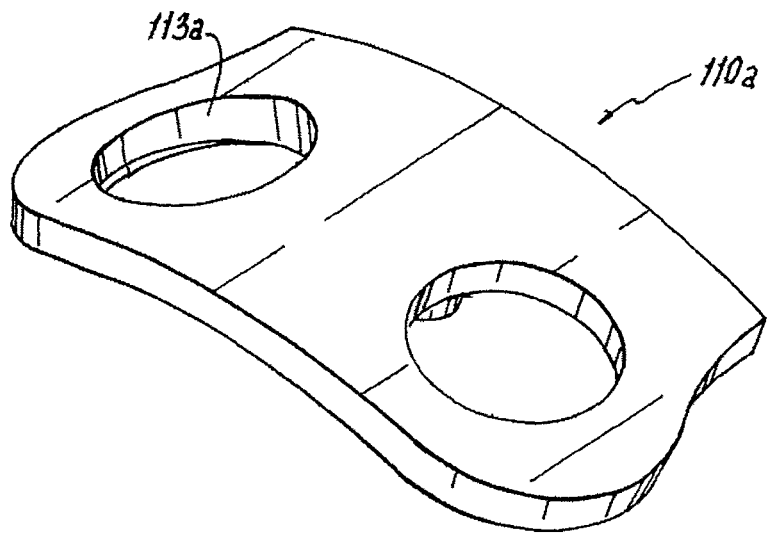
FIGS. 8A and 8B are, respectively, isometric line drawings of top and bottom surfaces of an upper plate segment of the dynamic vertebral column plate system of FIGS. 1A and 1B.
Figure 8B:
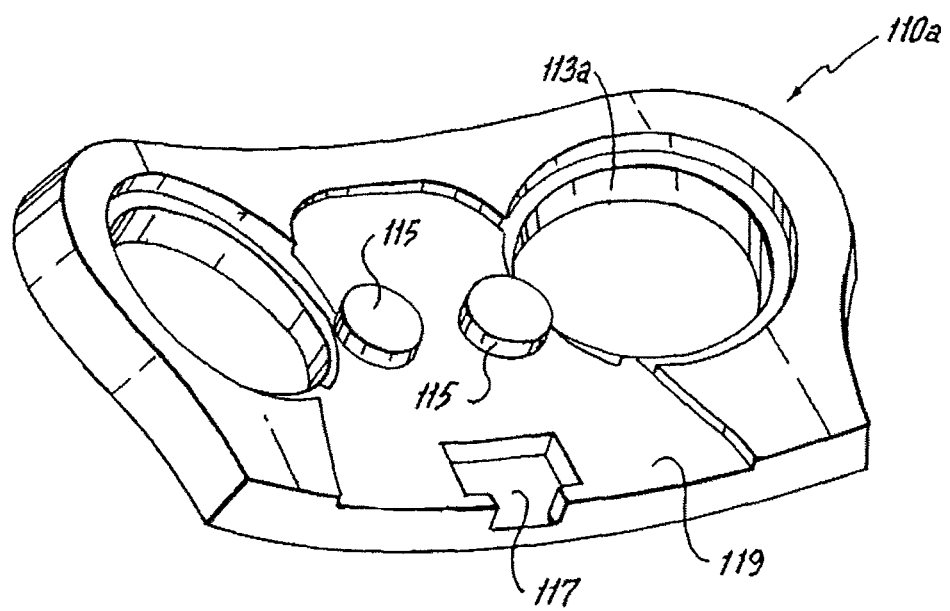
Figure 9:
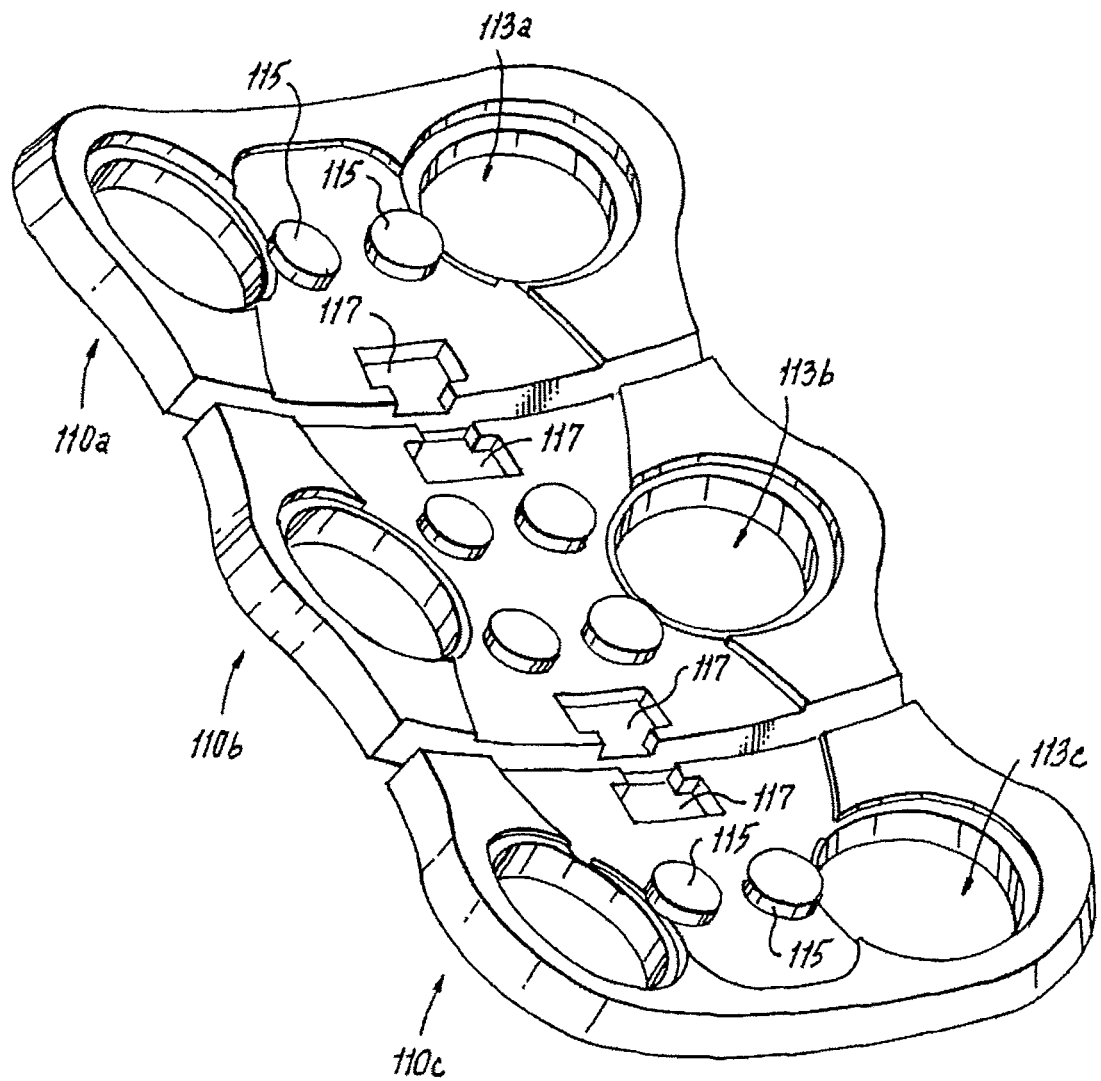
FIG. 9 is an a isometric line drawing, showing the lower surface of the upper plate segments of the dynamic vertebral column plate system of FIGS. 1A and 1B.
Figure 10:
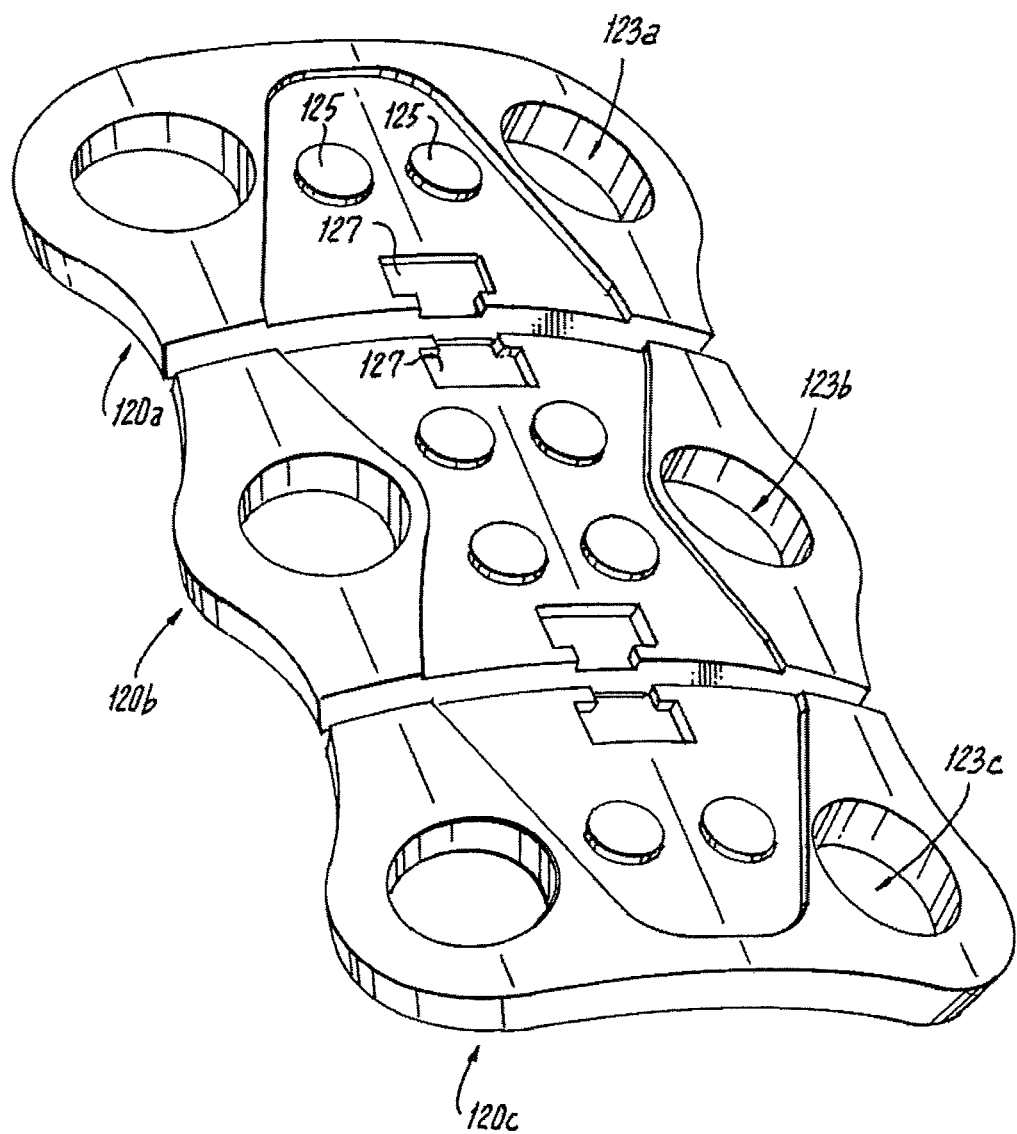
FIG. 10 is an a isometric line drawing, showing the upper surface of the lower plate segments of the dynamic vertebral column plate system of FIGS. 1A and 1B.

As mentioned above, FIGS. 2A and 2B are, respectively, an isometric line drawing and an isometric rendering showing internal structure of the dynamic vertebral column plate system of FIGS. 1A and 1B, shown without accompanying screws, in accordance with the present invention. FIGS. 3A and 3B are, respectively, a top line drawing and a top rendering showing internal structure of the dynamic vertebral column plate system of FIGS. 1A and 1B, shown with accompanying screws. FIG. 3C is a top line drawing of the dynamic vertebral column plate system of FIGS. 1A and 1B, shown without the accompanying screws. FIGS. 4A and 4B are, respectively, an end line drawing and an end rendering showing internal structure of the dynamic vertebral column plate system of FIGS. 1A and 1B, shown with accompanying screws. FIGS. 5A and 5B are, respectively, a side line drawing and a side rendering showing internal structure, of the dynamic vertebral column plate system of FIGS. 1A and 1B, shown with accompanying screws. FIG. 6A is a bottom line drawing of the dynamic vertebral column plate system of FIGS. 1A and 1B, shown with accompanying screws. FIG. 6B is a bottom line drawing of the dynamic vertebral column plate system of FIGS. 1A and 1B, shown without the accompanying screws. FIGS. 7A and 7B are, respectively, a line drawing and a rendering illustrating a detail view of a portion of the dynamic vertebral column plate system of FIGS. 1A and 1B, shown with an accompanying screw. FIGS. 8A and 8B are, respectively, isometric line drawings of top and bottom surfaces of an upper plate segment of the dynamic vertebral column plate system of FIGS. 1A and 1B. FIG. 9 is an a isometric line drawing showing the lower surface of the upper plate segments of the dynamic vertebral column plate system of FIGS. 1A and 1B, and FIG. 10 is an a isometric line drawing, showing the upper surface of the lower plate segments of the dynamic vertebral column plate system of FIGS. 1A and 1B.

As best seen in FIG. 3C, for example, the lower plate portions 120*a-c* of each plate segment include smaller apertures 123*a*, *b* or *c*, respectively for the screws 150 than the apertures 113*a-c* provided, respectively in the upper plate portions 110*a-c*. This allows firm engagement of the construct 100 to the vertebral column, with the larger apertures 113*a-c* allowing space for inserting the retaining clip 159.

Figure 12:
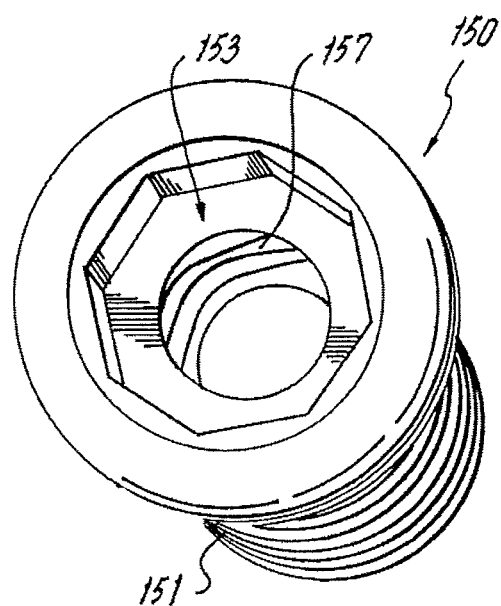
FIG. 12 is a top isometric view of the screw of FIGS. 11A, 11B and 11C, shown without the retaining clip, and illustrating a socket portion thereof.

As seen best in FIGS. 11A-11D, the screws 150 illustrated can include external threads 151 thereon for securely engaging bone. A proximal groove 155 accepts a retaining clip 159 for facilitating engagement with the construct 100. As seen in FIG. 12, the screw 150 can include a socket portion 153 and internal threads 152 provided therein to facilitate removal of the screw 150 from the bone, if necessary or desired. Such threads 152 are preferably opposite in directionality to the threads 151 of the screw 150, so that as the screw is being removed, the extraction tool does not disconnect itself from the screw 150.

Figure 13:
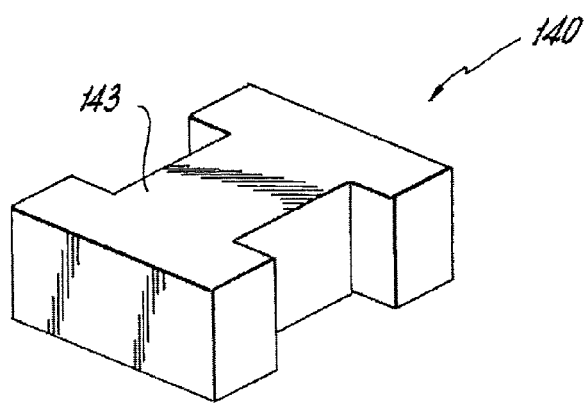
FIG. 13 is an isometric line drawing showing an engagement member for joining adjacent plate segments of the dynamic vertebral column plate system of FIGS. 1A and 1B.
Figure 14:
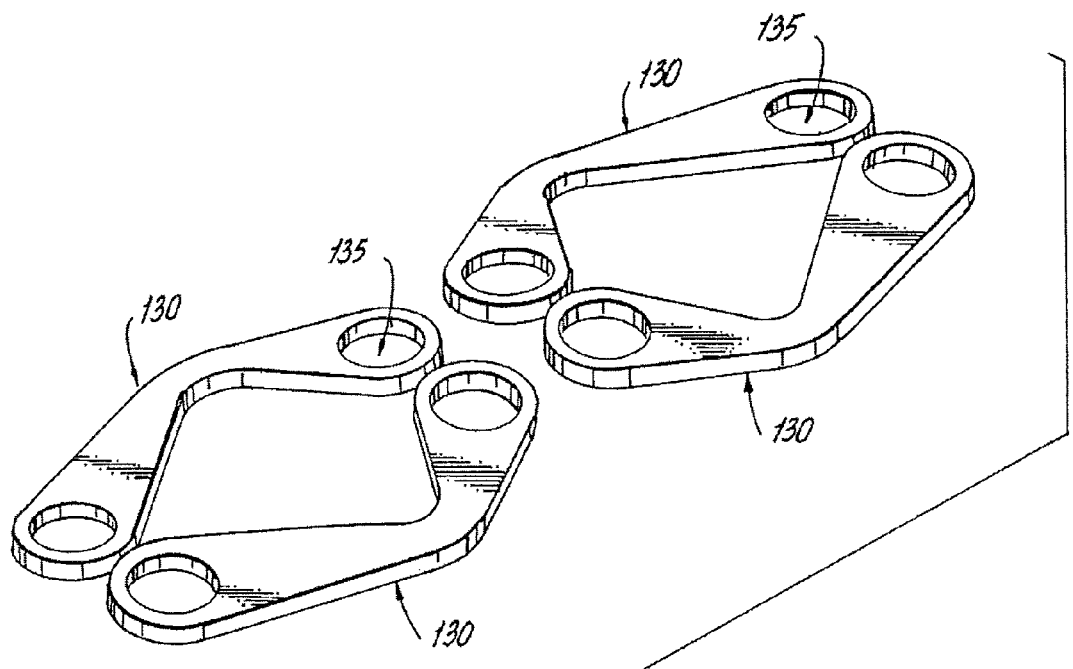
FIG. 14 is an isometric line drawing showing spring members for joining adjacent plate segments of the dynamic vertebral column plate system of FIGS. 1A and 1B.
Figure 15A:
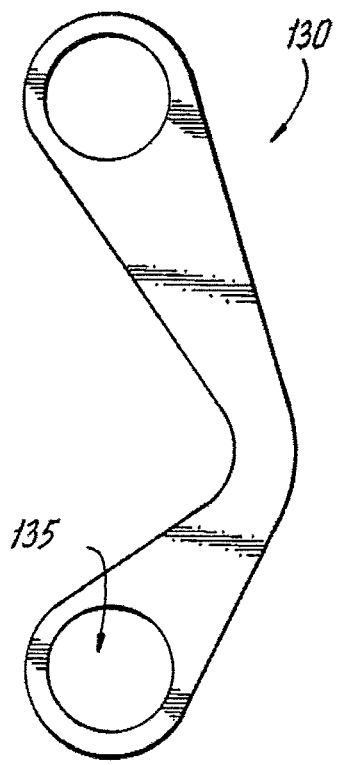
FIG. 15A is a top view of a spring member of FIG. 14.
Figure 15B:
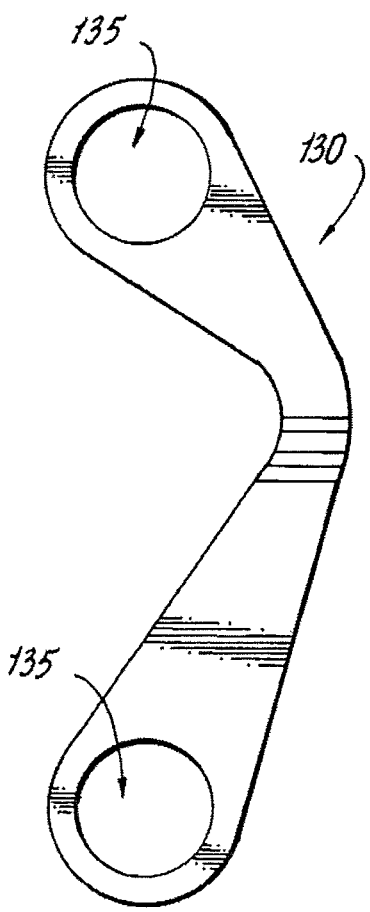
FIG. 15B is a bottom view of the spring member of FIG. 15A.
Figure 15C:
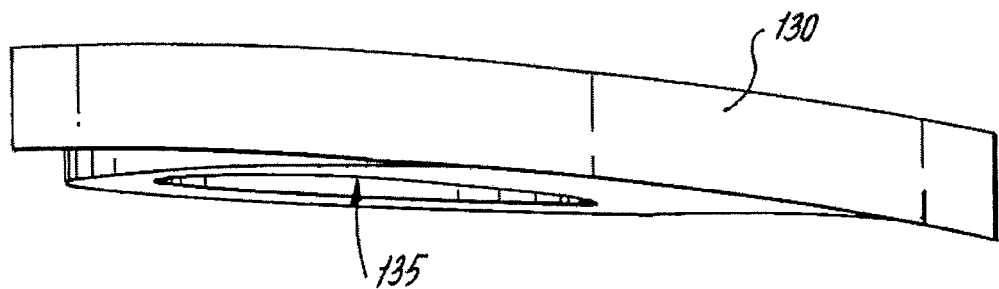
FIG. 15C is a front isometric view of the spring member of FIG. 15A.
Figure 15D:
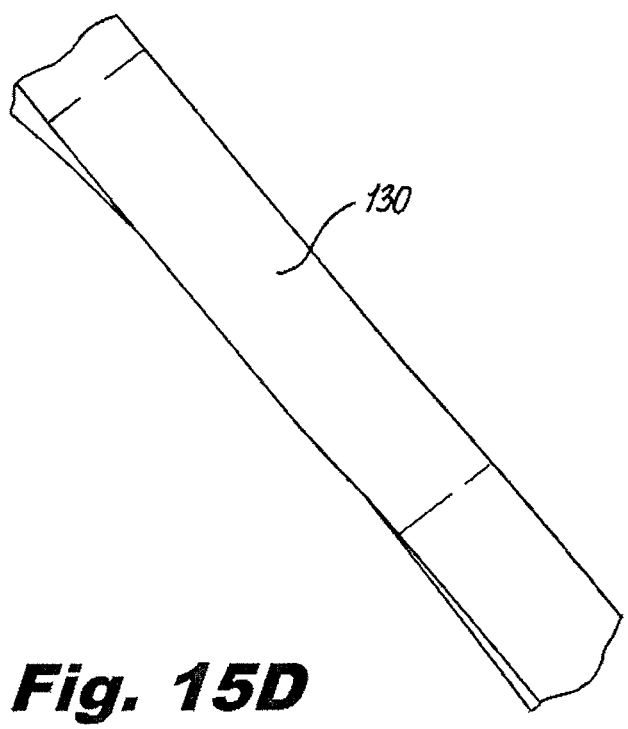
FIG. 15D is a an enlarged partial view of the spring member of FIG. 15A, illustrating a central bend thereof.
Figure 17:
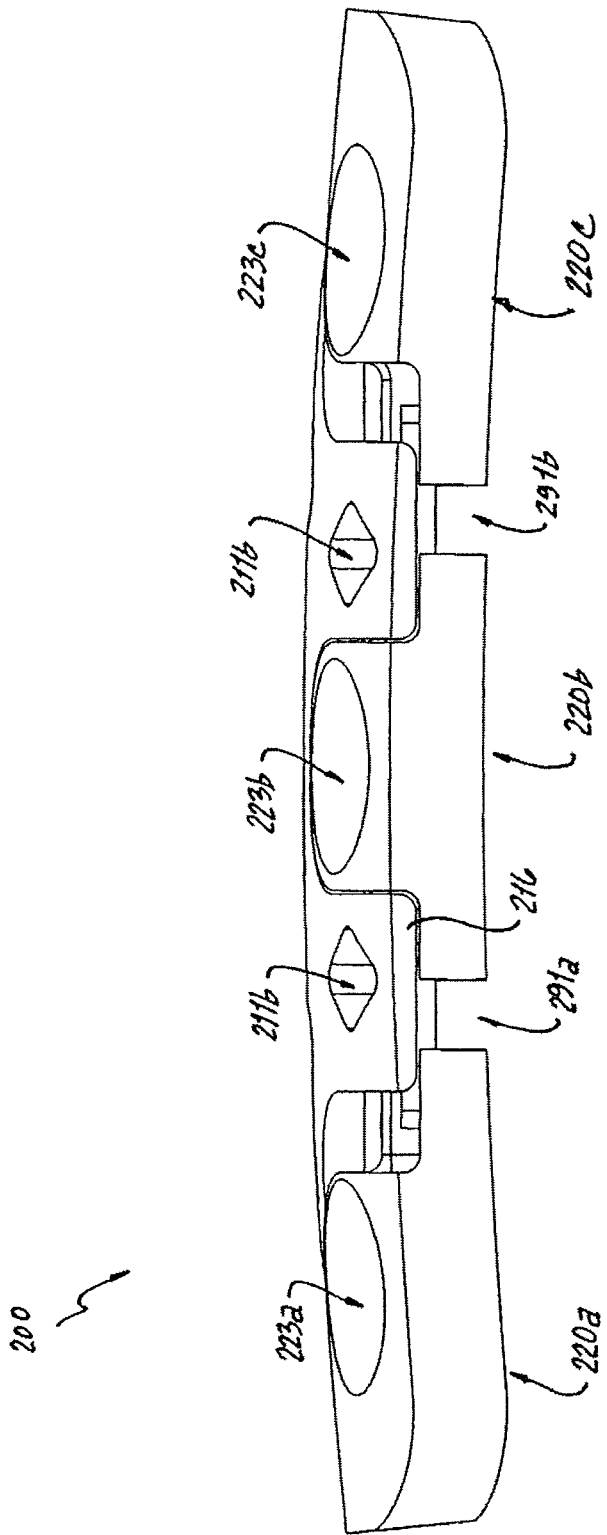
Figure 18:
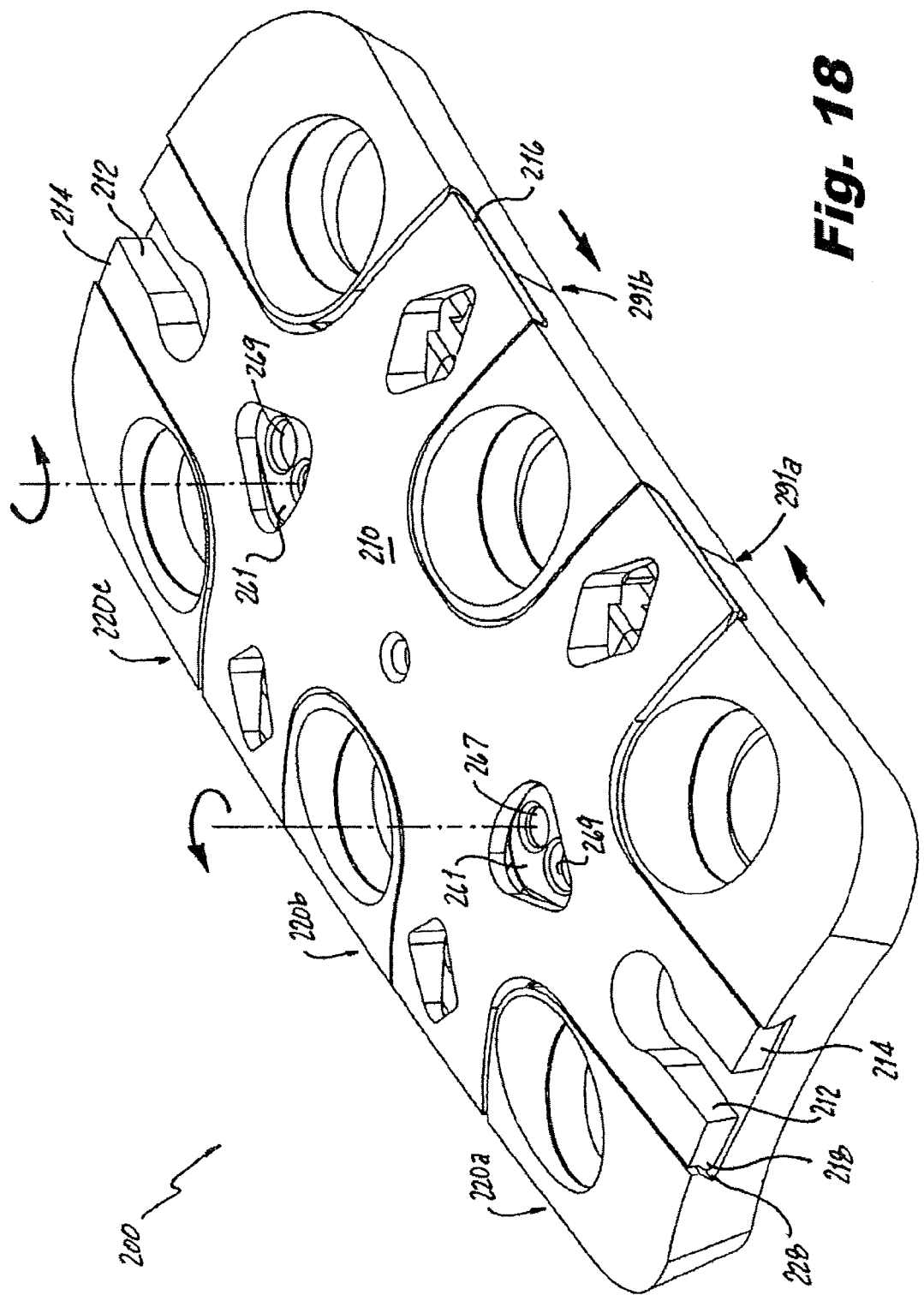
Figure 19:
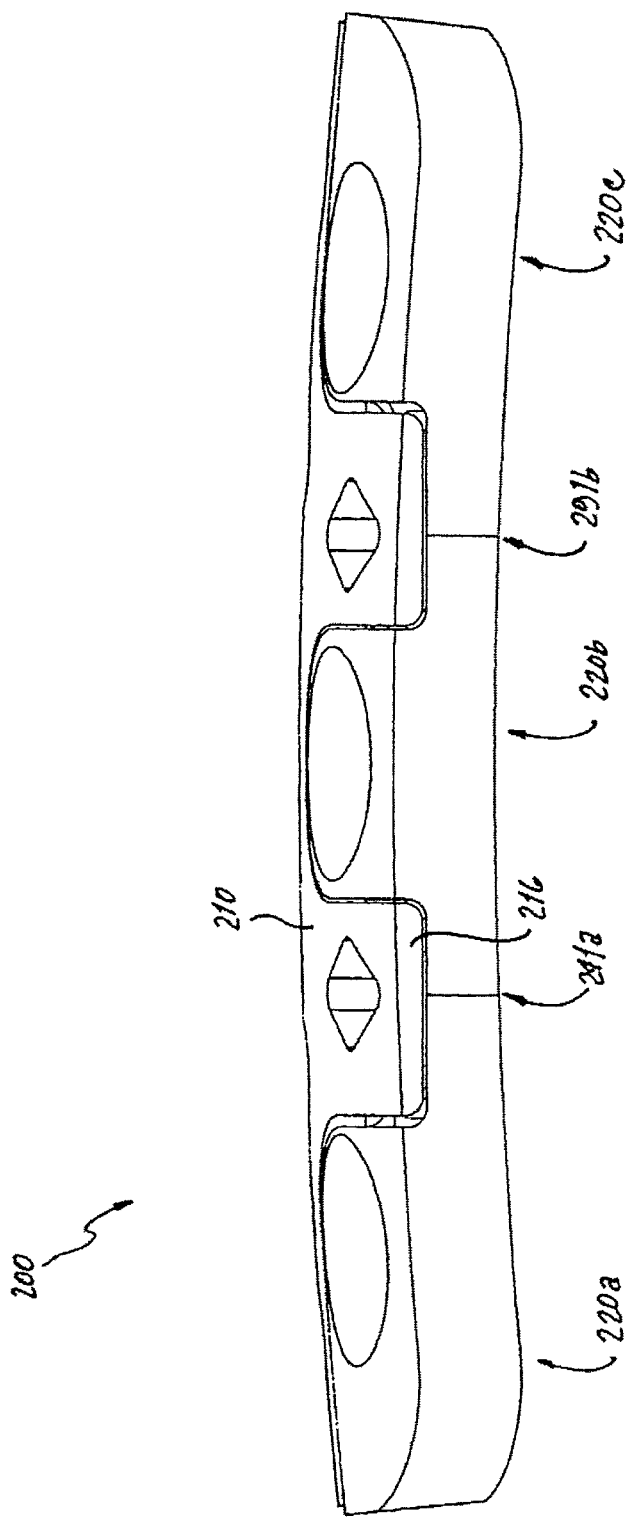
Figure 20:
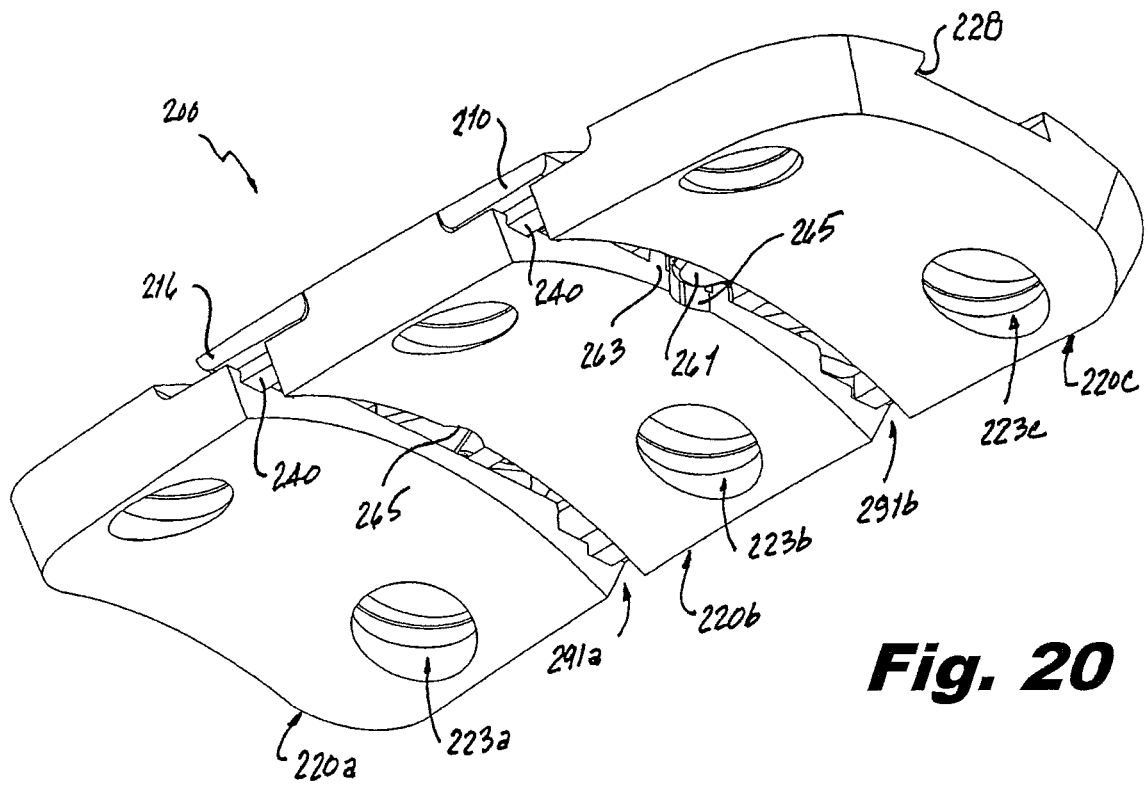
Figure 21:
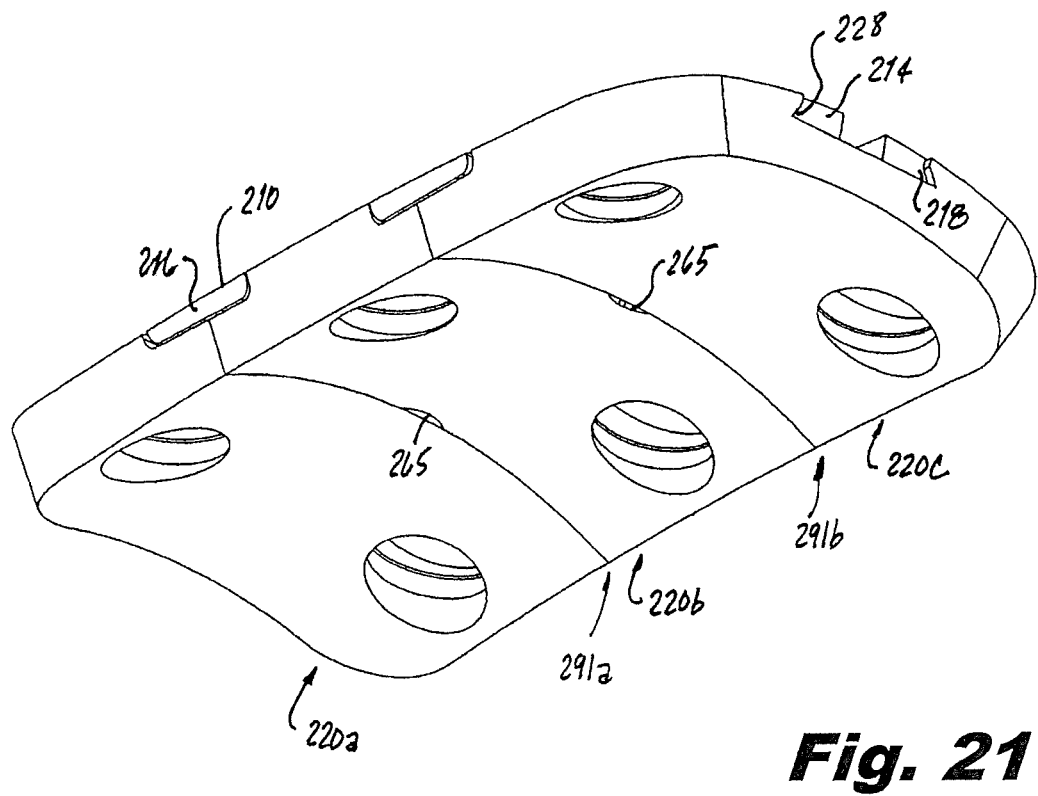

As best seen in FIG. 13, the engagement member 140 is shaped in this embodiment substantially as a solid "I-beam." Any of a variety of materials can be used, including by not limited to stainless steel, titanium alloys, nickel alloys such as Nitinol, polymeric materials, ceramic materials or composite materials, for example. The shape of the engagement member 140, and particularly the web portion 143 thereof, provides resistance to, but can allow, if so-embodied, a predetermined amount of bending of a construct created therewith.

In accordance with a preferred embodiment, the plate segments move in an axial direction (parallel to the longitudinal axis of the construct 100), guided by the engagement members 140. The springs 130 exert a compressive force between segments of the construct 100, while the engagement members 140 help stabilize the construct 100. In such embodiments, the engagement members 140 are preferably relatively strong, and stiff (i.e. resistant to bending forces).

Alternatively, if embodied to allow bending of the construct 100, due to the placement of the springs 130 with respect to the engagement member 140, lateral bending (roughly in the plane of the plate segments 110, 120, but parallel to the longitudinal axis thereof) would generally be less than in the direction perpendicular thereto (out of the plane of the plate segments 110, 120 (but still in a plane parallel to the longitudinal axis of the construct). The stiffness of the engagement member 140 in such embodiments can be selected by varying the material properties thereof, by changing the composition of the material, treating the material, or by altering the shape thereof—particularly the cross-sectional shape to alter the area moment of inertia thereof.

As seen in FIGS. 14 and 15A-15F, the spring elements 130 include engagement apertures 135 for mating with the spring engagement members 115 formed on the upper plate portions 110a-c and spring engagement members 125 formed on the lower plate portions 120a-c. The spring elements 130 can be formed of any suitable material, including but not limited to stainless steel, titanium alloys, nickel alloys such as Nitinol, polymeric materials, ceramic materials or composite materials, for example. The stiffness of the spring elements 130 can be selected by varying the material properties thereof, by changing the composition of the material, treating the material, or by altering the shape thereof. With respect to the springs 130, the nature of the integral bend and the cross-section of the component in that area can be altered to increase or decrease the stiffness thereof.

As illustrated, the spring 130 narrows to a relatively small cross-sectional area. When axial compression is the main modality of loading, the springs 130 can be provided prestressed, wherein the relaxed state of the spring results in a shorter length of the construct 100 than the pre-stressed state. In such embodiments, the construct 100 can be provided with removable spacers 160 (FIG. 1C) between plate segments that are removed following attachment to the vertebral column segment. Thereafter, the springs 130 exert a constant axial compressive force on the vertebral column segment.

In accordance with the invention, the stiffness of the engagement members 140, springs 130, in conjunction with the materials of the plate segments 110, 120 are selected to provide a desired amount of flexion in the construct when joined with a vertebral column segment. In accordance with one aspect, devices in accordance with the invention allow for between about 0 and 5.0 mm, and preferably between about 1.0 mm to 3.0 mm of axial contraction at each level, across each intervertebral space. In accordance with another preferred aspect, the subject devices allow for about 2.0 mm of axial contraction at each level. If desired, the characteristics of the construct can be varied at different levels, providing greater preload force, or alternatively resistance to axial contraction and/or bending at one level than at another level, if desired.

The shape of the plate segments 110, 120, engagement members 140 and springs 130 preferably result, when combined with the respective vertebral column segment, in a curvature very close to the natural curvature of that vertebral segment. Other than providing a bias to maintain pressure across the intervertebral spaces to promote fusion of bone grafts, the curvature is preferably very close to that of the vertebral column segment to which it is to be attached.

Further, the spacing between adjacent plate segments can be selected as desired, and can vary between adjacent levels, across consecutive intervertebral spaces, for example. Such flexibility allows for more versatility when used with a patient's individual anatomy.

Moreover, devices in accordance with the invention can be configured so as to provide preloading across an intervertebral space to facilitate spinal fusion. This is accomplished, for example, by providing a bias in the curvature of the assembled construct 100. This can be achieved by providing the engagement members 140 and/or springs 130 with a pre-formed bend. Such bend need only be slight to result in an effective bias.

Screws, such as screws 150, for use in conjunction with devices in accordance with the invention can include any desired features known in the art. Such screws can be adapted for fixed angle insertion or variable angle insertion having an arcuate lower surface at the junction of the plate segments 110, 120. Such screws can be self-tapping or self-drilling. Features of example screws for use with devices in accordance with the invention are described below in connection with FIGS. 31A-H.

Figure 23:
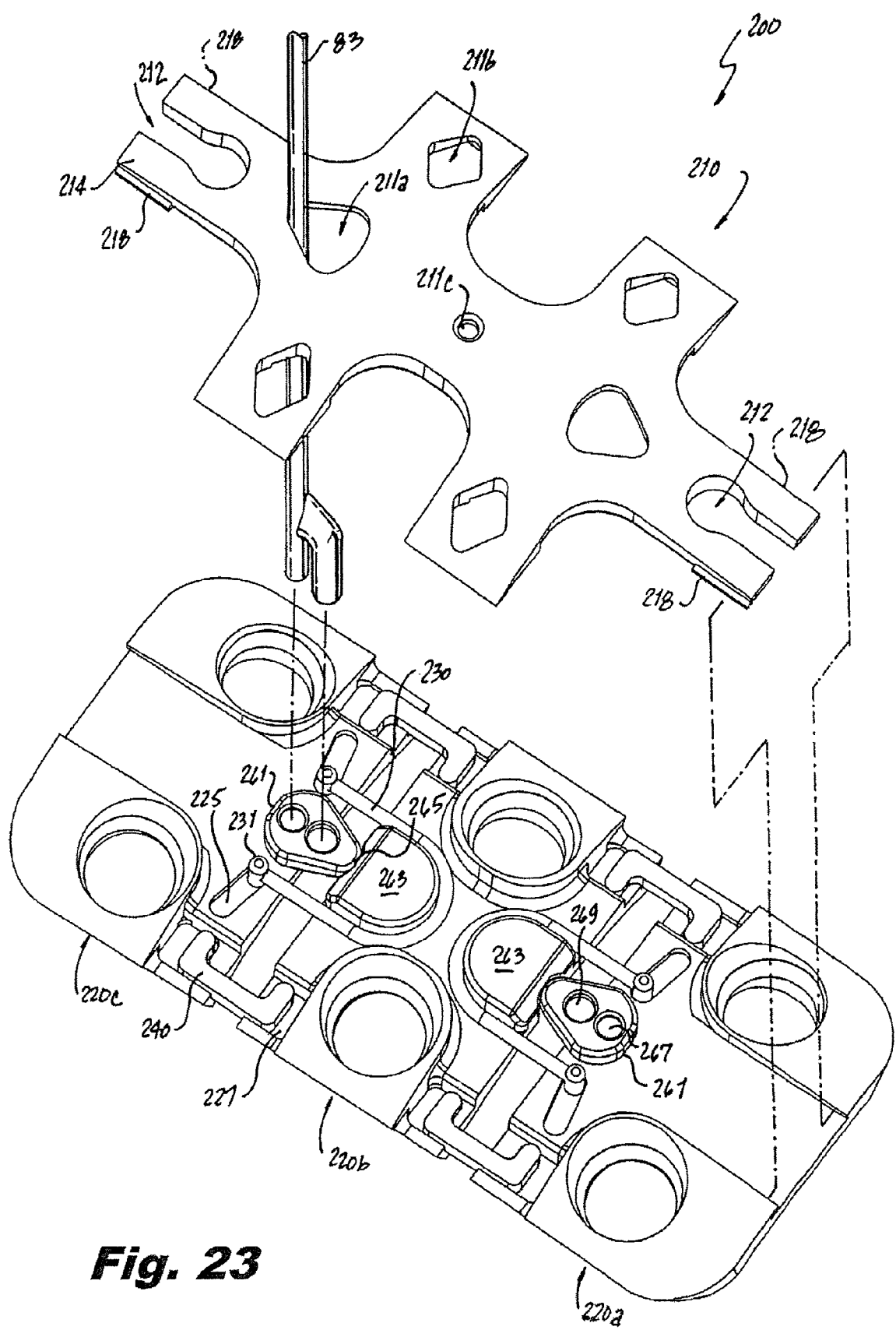
Figure 24:
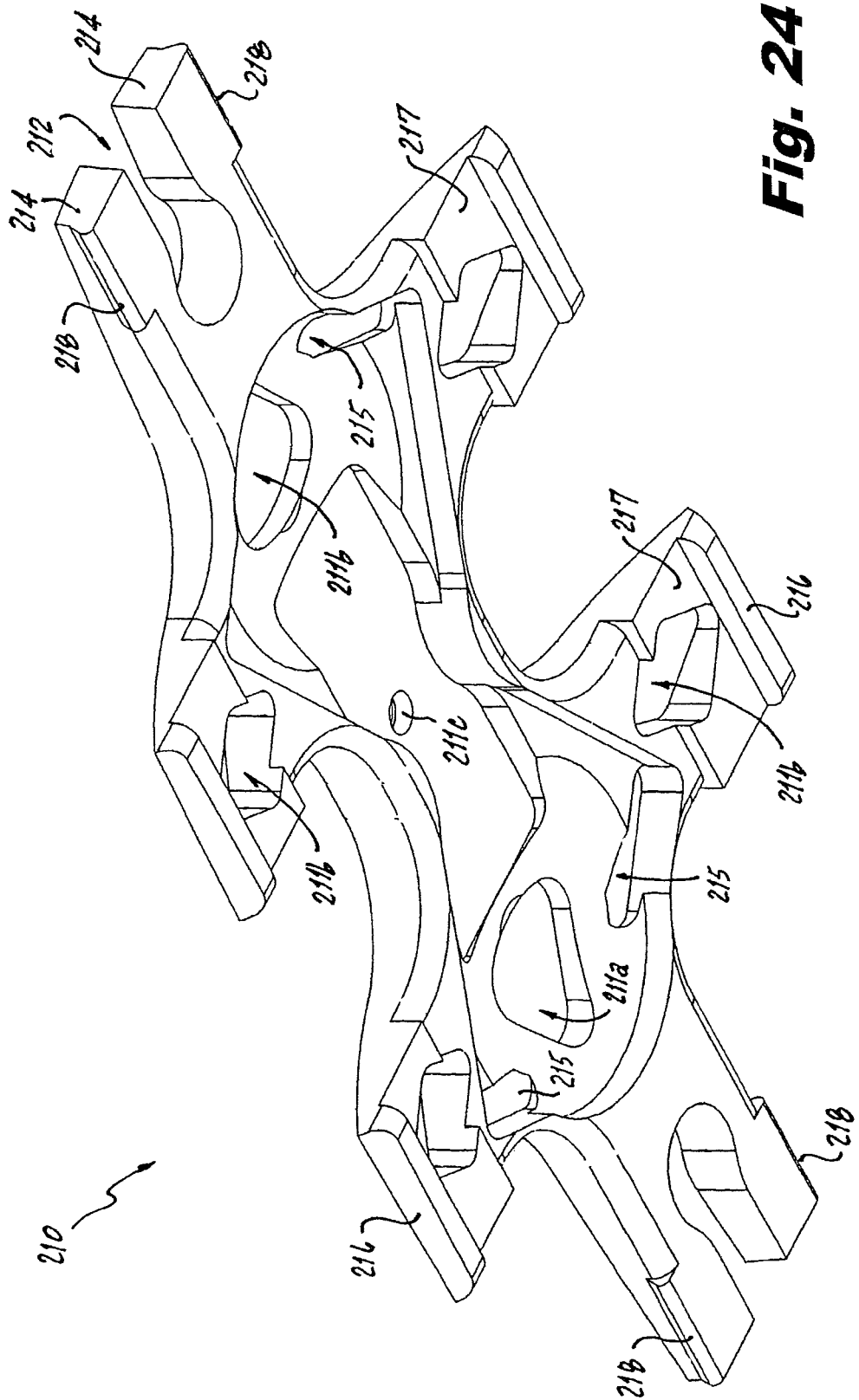
Figure 25:
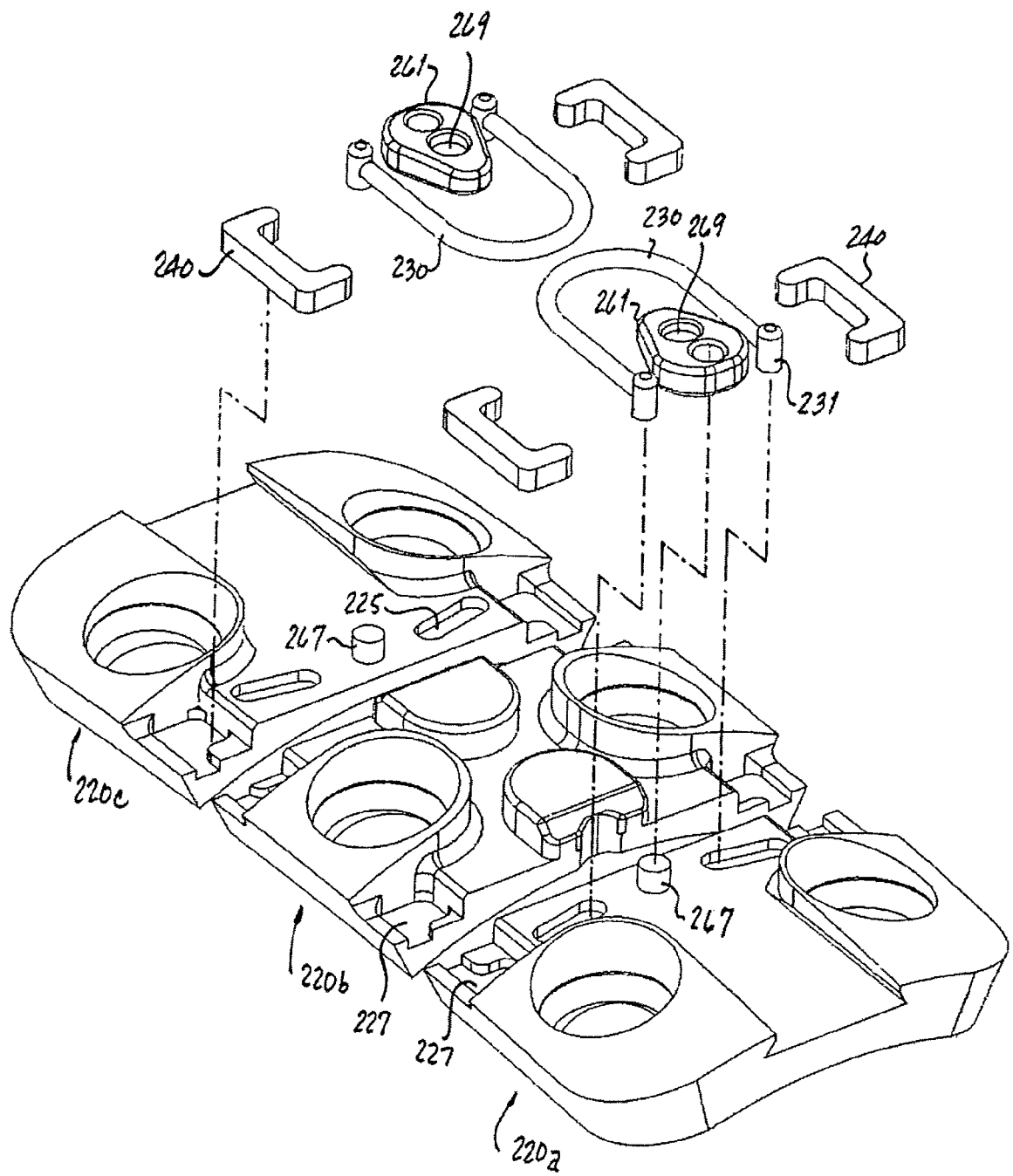

FIGS. 16-29 illustrate various views of another exemplary embodiment of a dynamic vertebral column plate system construct in accordance with the invention, designated generally by reference number 200. The construct 200 has, among other features, arcuately bent rod or bar-shaped springs 230 and an integral cam element 261 that permits use of the construct 200 as either a static plate or dynamic plate, providing preload at one or more levels of a spinal segment. Simply put, if the cam 261 is left in a locked position (e.g., as shown in FIG. 23) following implantation or alternatively, unlocked prior to implantation, then no preload will be applied to that respective level. If, however, the cam 261 is locked during implantation and unlocked following attachment to a spinal segment, a preload, provided by a respective spring 230, will be applied at that level.

The construct 200 includes a number of features analogous to the construct 100 discussed in connection with FIGS. 1-15F. For example, the construct 200 includes a plurality of apertures 223a-c for accepting screws for connection with respective vertebrae, a plurality of lower plate portions 220a-c, engagement members or guides 240, and springs 230 for applying preload at respective levels, although the configuration of these features may vary somewhat substantially from those of the construct 100, as will be described in more detail below.

Notable differences between the construct 100 discussed in connection with FIGS. 1-15F, and the construct 200 of FIGS. 16-29 include a unitary upper plate 210, an integral cam 261 and associated features, a different arrangement of the springs 230 that apply a preload, if desired.

The unitary upper plate 210 of the construct 200, is distinct in configuration from the individual upper plate portions 110a-c of the construct 110 of FIGS. 1-15F. The unitary upper plate advantageously enhances stability of the construct 200, and thus also any attached spinal segment, while permitting linear translation of adjacent lower plate segments 220a, 220b, 220c, and therefore also permitting an axial application of load across the attached spinal segment to promote fusion.

As can be seen particularly in FIGS. 22A, 22B and 22C, the end plate segments 220a, 220c are engaged with the upper plate 210 by way of a female dovetail 228 formed in the lower plate segments 220a, 220c, and a male dovetail 218 formed on the upper plate 210. The dovetails 218, 228 restrain the relative movement between the end plate segments 220a, 220c and the top plate 210 along each axis except for along a longitudinal axis, which movement is restrained in expansion by engagement members 240 and springs 230, and restrained in contraction by interference with adjacent plates, such as the intermediate plate 220b. Engagement of the dovetail 218 of the upper plate 210 is permitted with the provision a cutout 212, which allows for deflection of resulting forks 214 of the upper plate 210, surrounding the cutout 212, on which the dovetail 218 is formed.

As with the construct 100, engagement members 240 are provided, which serve to promote stability of the construct 200 and to limit expansion of the construct 200 beyond a predetermined amount. The lower plate segments 220a-c include slots 227 to accommodate the engagement members 240, while the upper plate 210 includes corresponding slots 217 for that purpose. The upper plate 210 includes tail portions 216 that partially define slots 217 therein for the engagement member 240, and permit close engagement at lateral edges of the construct 200 between the upper plate 210 and lower plate segments 220a, 220b, 220c.

Various apertures 211a, 211b, 211c are provided in the upper plate 210 for respective purposes. A central aperture 211c is provided to permit pinning of the lower intermediate plate segment 220b to the upper plate 210 during assembly. Such a pin can be peened, welded or connected to the upper and lower plates in another suitable manner. Such a pin can be integrally formed, such as by casting and/or machining, with one of the lower intermediate plate segment 220b and the upper plate 210, for example. Alternatively, any intermediate plate such as plate 220b can be connected to the upper plate 210 in another manner, such as by a dovetail feature discussed in connection with the end plate segments 220a, 220c, for example.

Figure 30A:
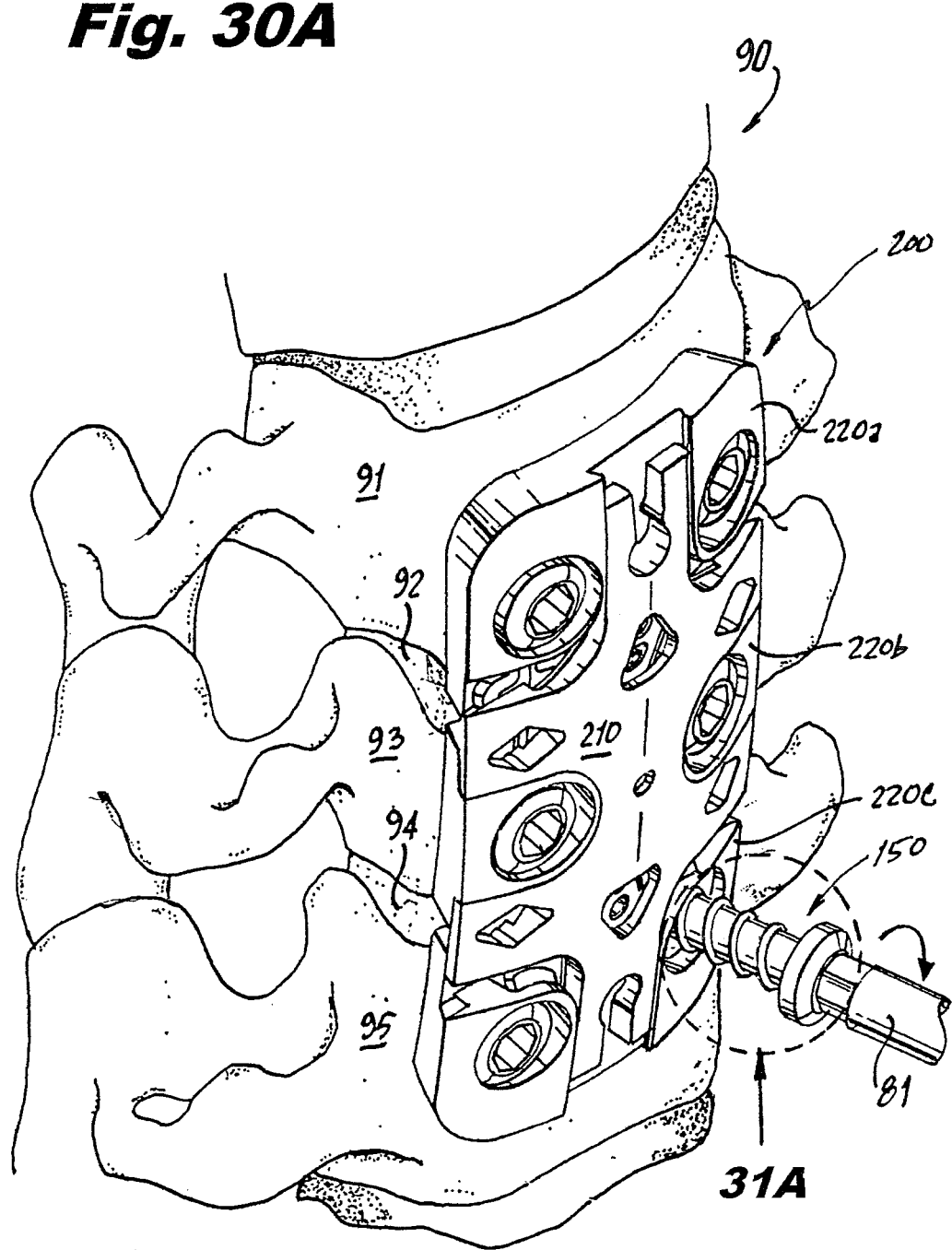
FIGS. 30A-C illustrate implantation steps of the dynamic vertebral column plate system construct of FIGS. 16-29, but which steps apply generally to other embodiments of the invention.
Figure 30B:
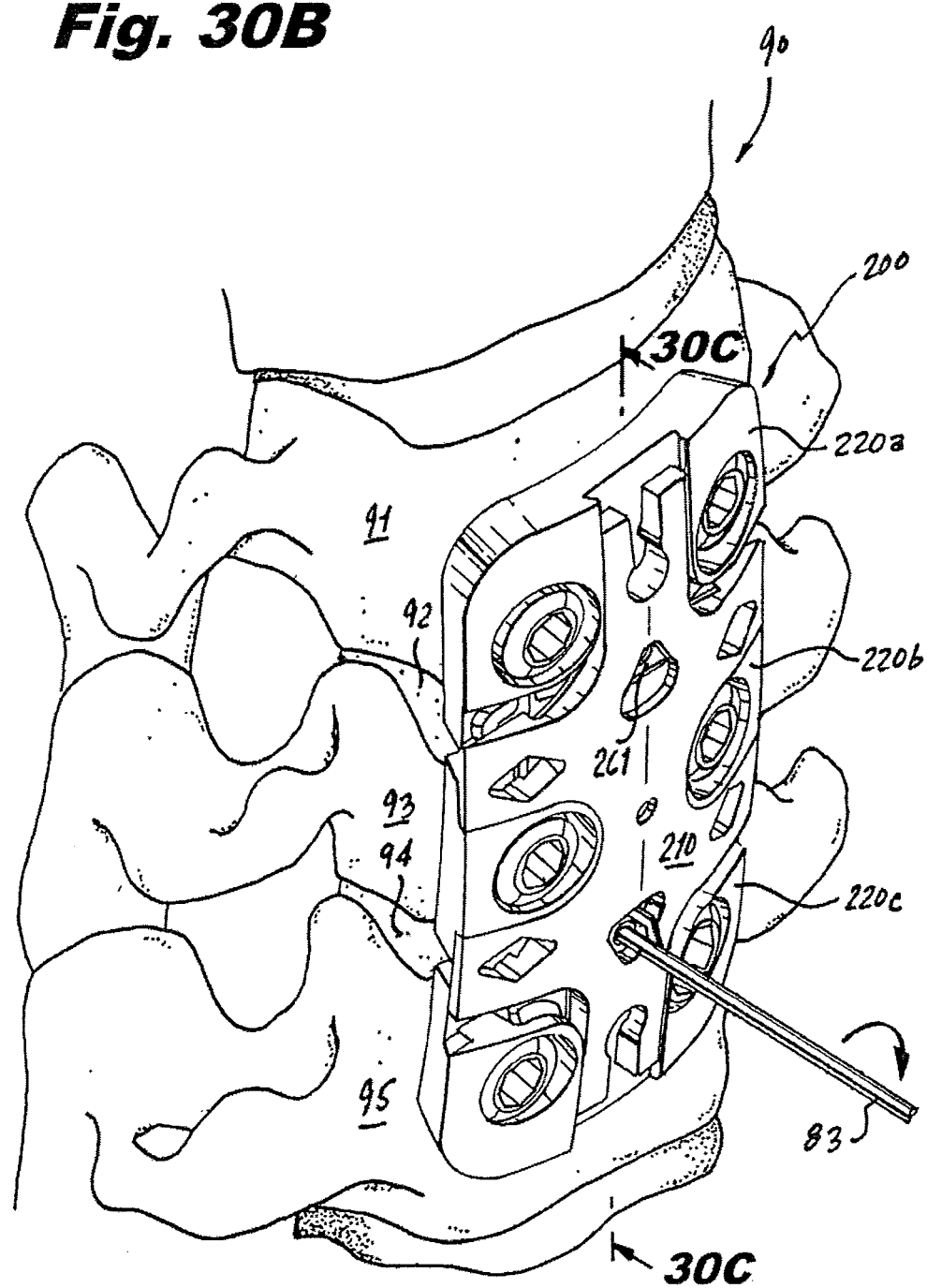

Respective apertures 211a are provided to enable access to each cam 261, to rotate the cam 261 between locked and unlocked positions, as illustrated in FIG. 30B, for example. Apertures 211b are also provided in line with, the spaces 291a, 291b between lower plate segments 220a, 220b, 220c, which apertures 211b provide a viewing window of the intervertebral space, through the construct 200, so that a surgeon can view the relative spacing between lower plate segments 220a, 220b, 220c, and also the condition of a bone graft (of the vertebrae and any fusion devices or materials), during and after attachment of the construct 200 to a spinal segment. A surgeon can therefore determine, based on his or her experience, whether or not that level of the construct should remain static or if the cam 261 should be unlocked to provide a dynamic load application at that level. The surgeon may take various factors into account, including any gaps that he or she may see in the intervertebral space, between vertebrae and any fusion materials, for example.

Figure 26:
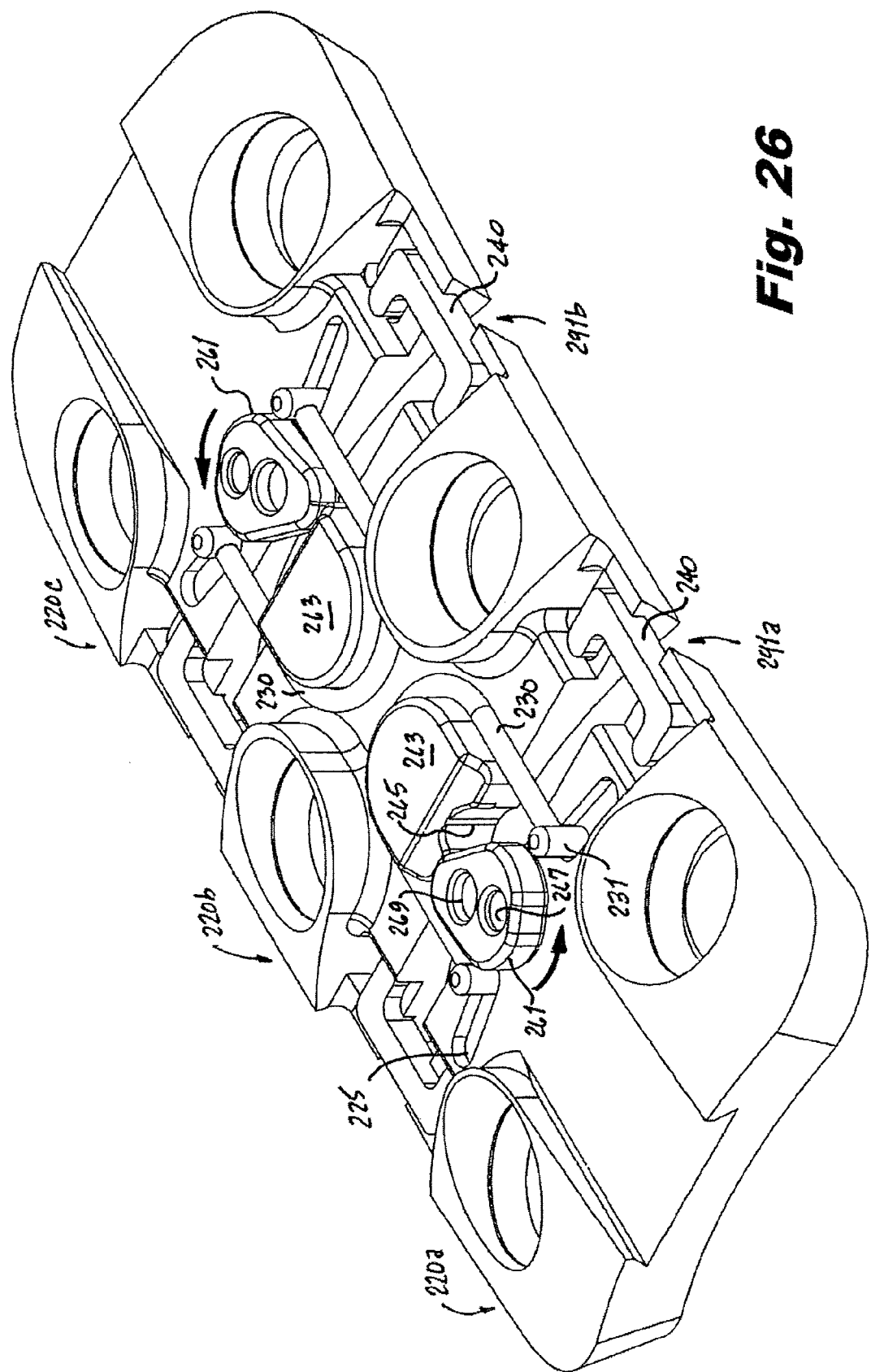
Figure 27:
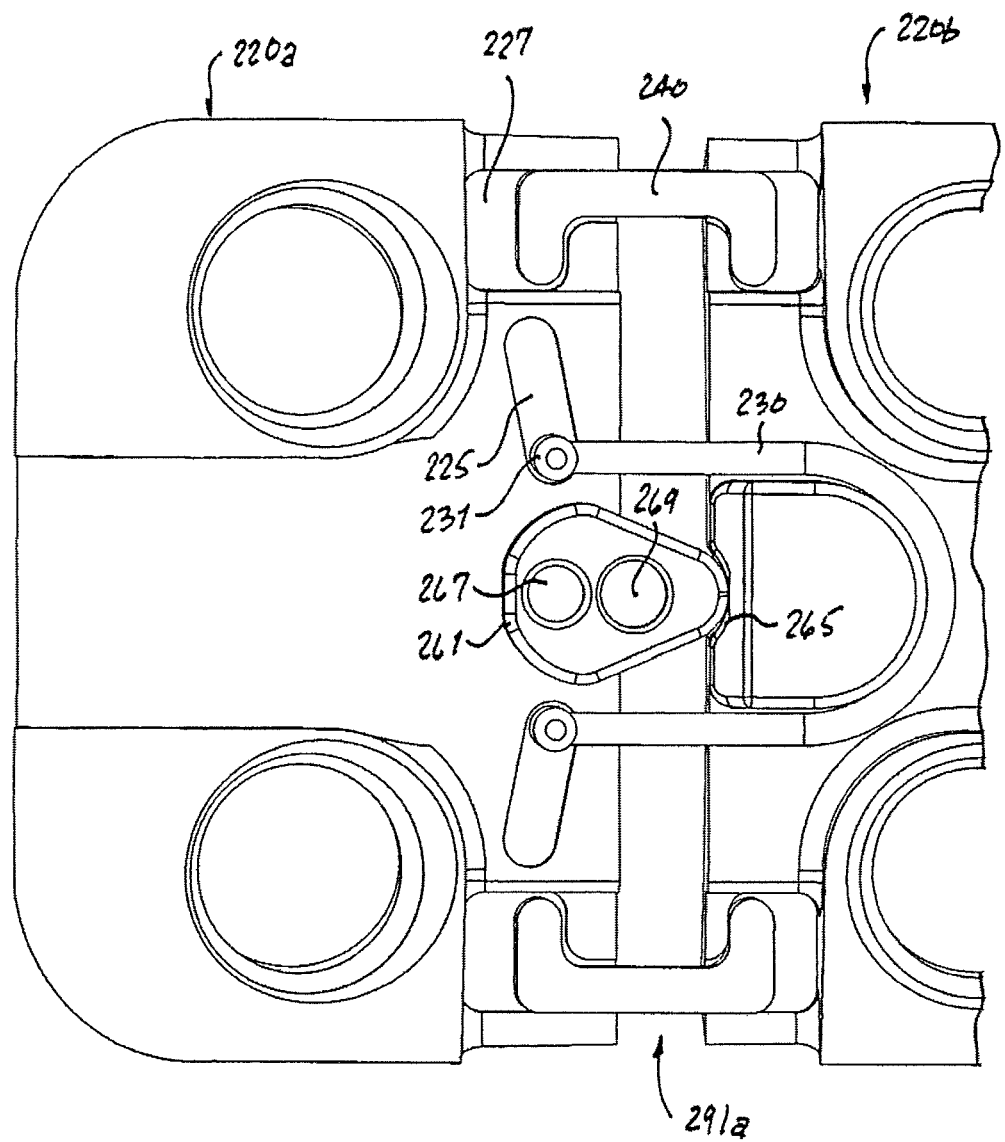

Following implantation, a surgeon can elect to leave one or more of the cams 261 in the locked position, or alternatively can unlock one or more cams prior to implantation, causing the corresponding gap (e.g. 291a, 291b) to close. In either case, that level of the construct 200 would behave essentially as a static plate. More typically, however, following implantation, each of the cams 261 will be unlocked by turning the cam 261 from its seat in recess 265, as shown in FIG. 26, for example. At that time, even if no visible contraction occurs, the spring 230 at that level begins to exert force across the corresponding gap (e.g. 291a), and therefore to the spinal segment, which will typically be a fusion between vertebrae.

In accordance with an alternative embodiment, the cam 261 can be provided that is similar to the cam 561 discussed below in connection with the embodiment of FIGS. 33-39. Alternatively still, the cam 261 can be configured and adapted to engage a pin at one position to stretch the respective spring 230, to thus effect an increased preload following implantation.

The springs 230 are configured as an arcuate rod or bar. As illustrated, the ends of the springs 230 are held in pins 231 that are translatable with respect to slots 215 and 225, formed respectively in the upper plate 210 and lower plates 220a, 220c (See FIGS. 23 and 24).

At the maximum extent of expansion of the construct 200, illustrated for example in FIGS. 16, 17, 20, and 23, gaps 291a, 291b between adjacent lower plate segments 220a, 220b and 220c are also at their maximum, which is limited by the central spring 230 and the laterally placed U-shaped engagement members 240, which are engaged in recesses 117, 127 formed in the top plate 110 and each of the bottom plate segments 220a-c, respectively. The cams 261, rotate on respective bosses 267 and in their locked position, engage recesses 265 formed on a facing surface of the adjacent plate, maintaining a predetermined spacing. In addition to an aperture in the cam 261 for accommodating the boss 267, an aperture 269 can be provided in the cam for engagement with a tool for rotating the cam 261.

The dimensions of the components can be selected to vary the amount of spacing between adjacent plates, however, in accordance with one preferred embodiment, the maximum spacing of the gaps 291a, 291b is about 2.0 mm, for example, for use in a cervical spinal segment. This spacing can be selected to be smaller or larger, such as between 1.0 mm and 3.0 mm of translation, depending on the placement of the construct 200 (or any other construct in accordance with the invention). That is, if used on a lumbar spinal segment, the construct can be configured so as to provide a larger maximum spacing between plate segments, for example 3.0 mm or perhaps larger if indicated for a particular application. The maximum spacing 291a, 291b between plate segments 220a-c determines the maximum range of travel along which the spring 230 can apply a preload to a level of the spine, such as across a fusion.

A block of bone, a fusion cage or other fusion material is typically inserted in place of a disc, between vertebrae that are to be fused together and carries the bulk of load carried by the spine. The construct 200, then provides stabilization to the spinal segment to which it is attached while minimizing load transfer to the construct, which promotes proper fusion. The springs 230 also maintain a load on the segment even in the absence of external load. In this manner, the construct 200 (and other constructs in accordance with the invention) advantageously permit settling of fusion materials, while minimizing any spacing between adjacent vertebrae and the fusion materials, further enhancing fusion.

Figure 29:
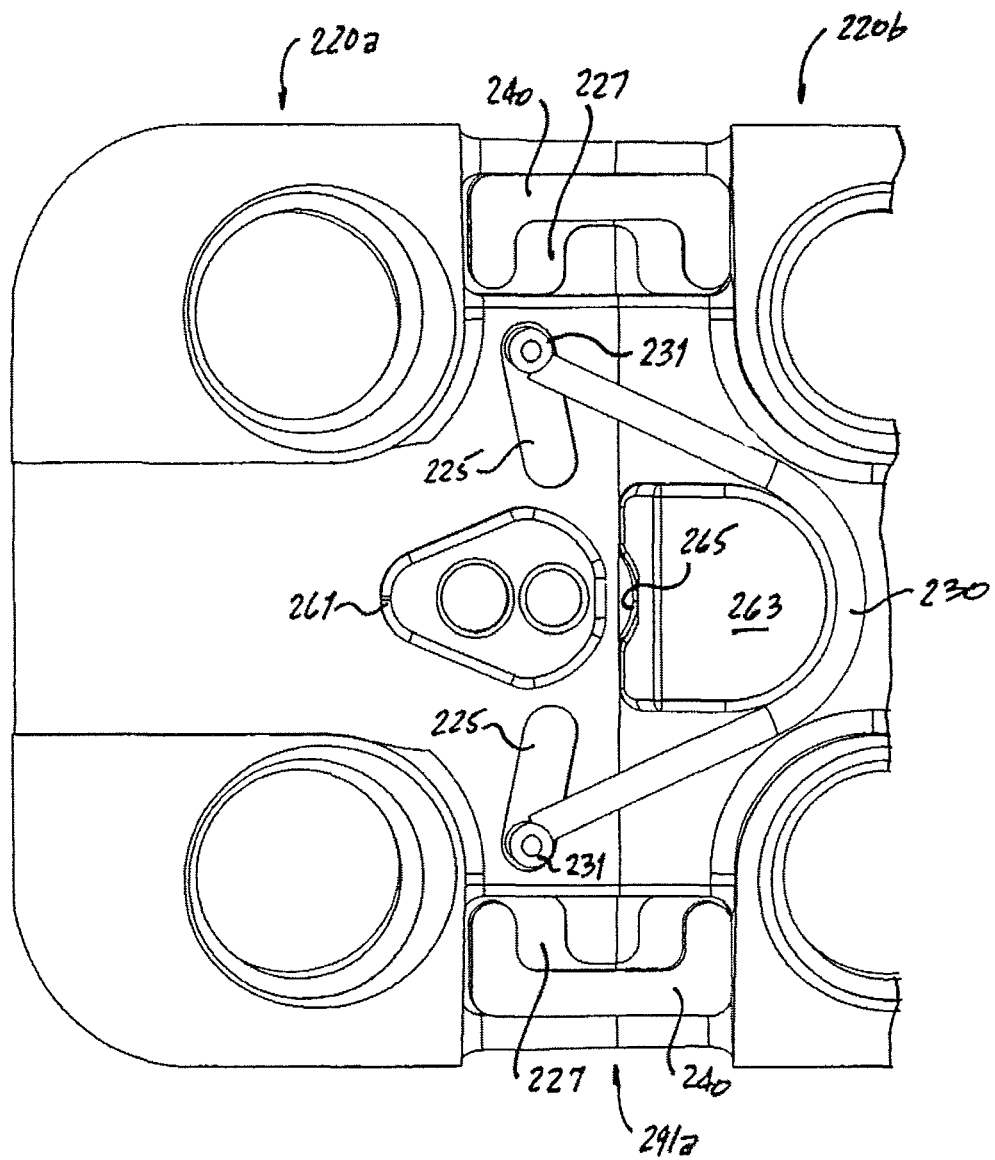
Figure 30C:
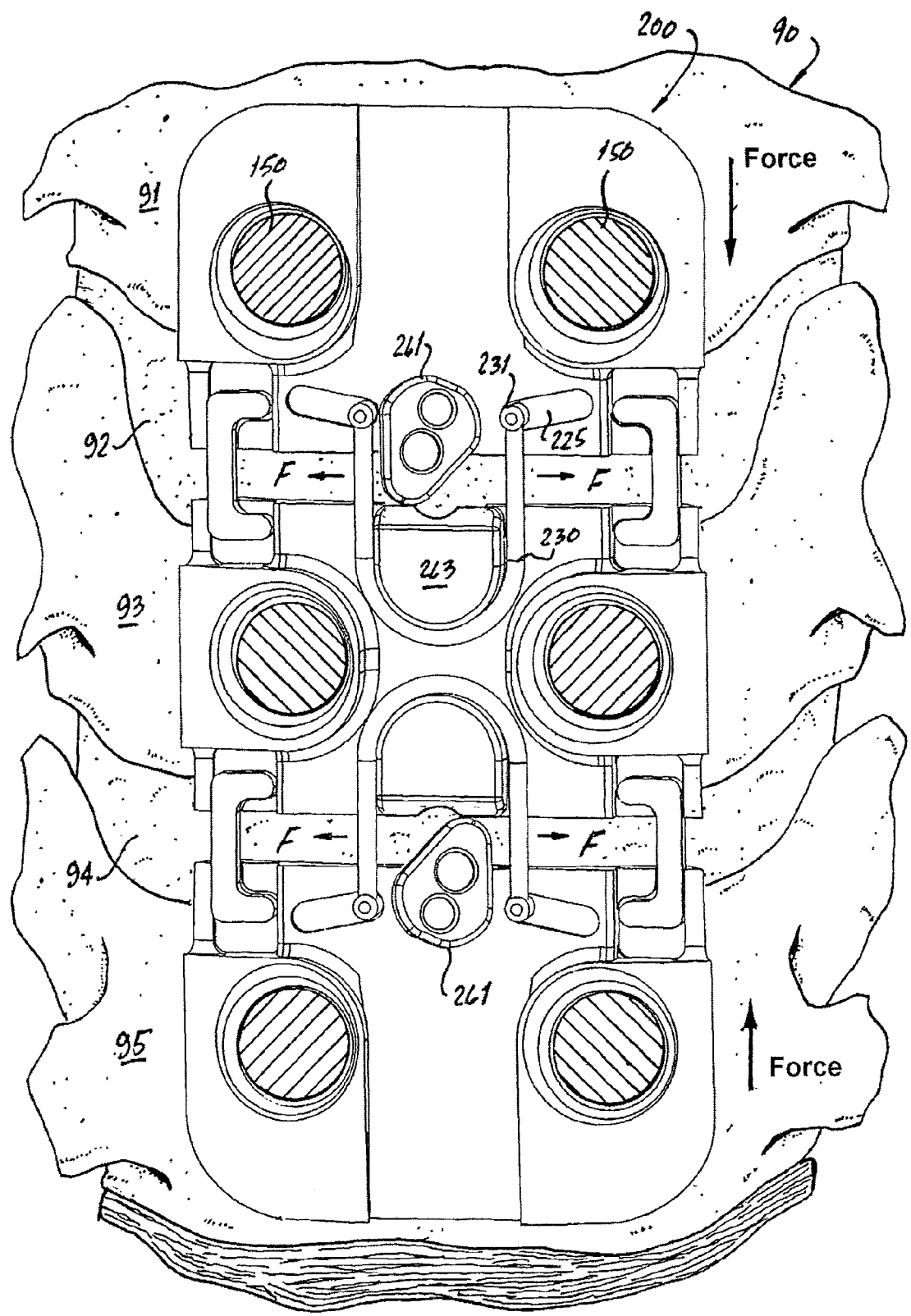

In the embodiment of the construct 200 of FIGS. 16-29, implantation of which is illustrated in FIGS. 30A, 30B and 30C, the springs 230 are arcuately-shaped rod or bar elements, formed from a resilient material. In accordance with a preferred aspect, the springs 230 are formed of a shape memory alloy, such as Nitinol. In accordance with one aspect, the springs 230 are linear in their natural state and are bent into the illustrated arcuate configuration upon assembly of the construct 200. The diameter of the springs 230 is selected based on the desired amount of force to be applied. Accordingly, the springs 230, in attempting to revert to their natural configuration, rotate in an outward arc, exerting initially a substantially laterally outward force through the pins 231 at the ends thereof to the outer plate segments 220a, 220c by way of the slots 225 formed therein.

The slots 215 formed in the underside of the top plate follow the arc of the pins 231 caused by the spring 230. The slots 225 in the lower end plate segments 220a, 220b are linear in configuration, with the longitudinal component of the arc of travel of the pins 231 being provided in the translation of the plate segments 220a, 220c themselves, in closing the gaps 291a, 291b. The linear configuration of the slots 225 of the lower end plate segments 220a, 220c in which the pins 231 ride, promote resolution of the generally arcuate application of spring force into an axial force, parallel to the translation of the end plate segments 220a, 220c. As can be appreciated, any transverse component of force applied by the spring will be applied symmetrically by each of the pins 231, which forces with therefore cancel one another within the outer plate segments 220a, 220c, and not result in any net external forces.

As configured, the slots 225 are not perfectly parallel to the edge of the plates 2201, 220c. The degree of angle of the slots 225 is provided to increase the distance of translation of the outer plate segments 220a, 220c across which sufficient force application is applied.

In accordance with the invention, a target force application can be between about 0 N and 90 N (between about 0-20 pounds-force). In accordance with one embodiment of the invention, a target force application is between about 13 N and 44 N (between about 3-10 pounds-force) for applications on a cervical vertebral segment. Alternatively, depending on the spinal segment, the target force application can be greater or smaller. In accordance with another embodiment of the invention, a target force for application is between about 44 and 89 N (between about 10-20 pounds-force) for thoracic or lumbar vertebral segments. As discussed herein, if resistance to compressive forces are desired and application of a preload by any of the constructs described herein is not desired, then such target force is 0N. Any application of force sufficient to safely achieve the desired effect is possible in accordance with the invention.

Figure 28:
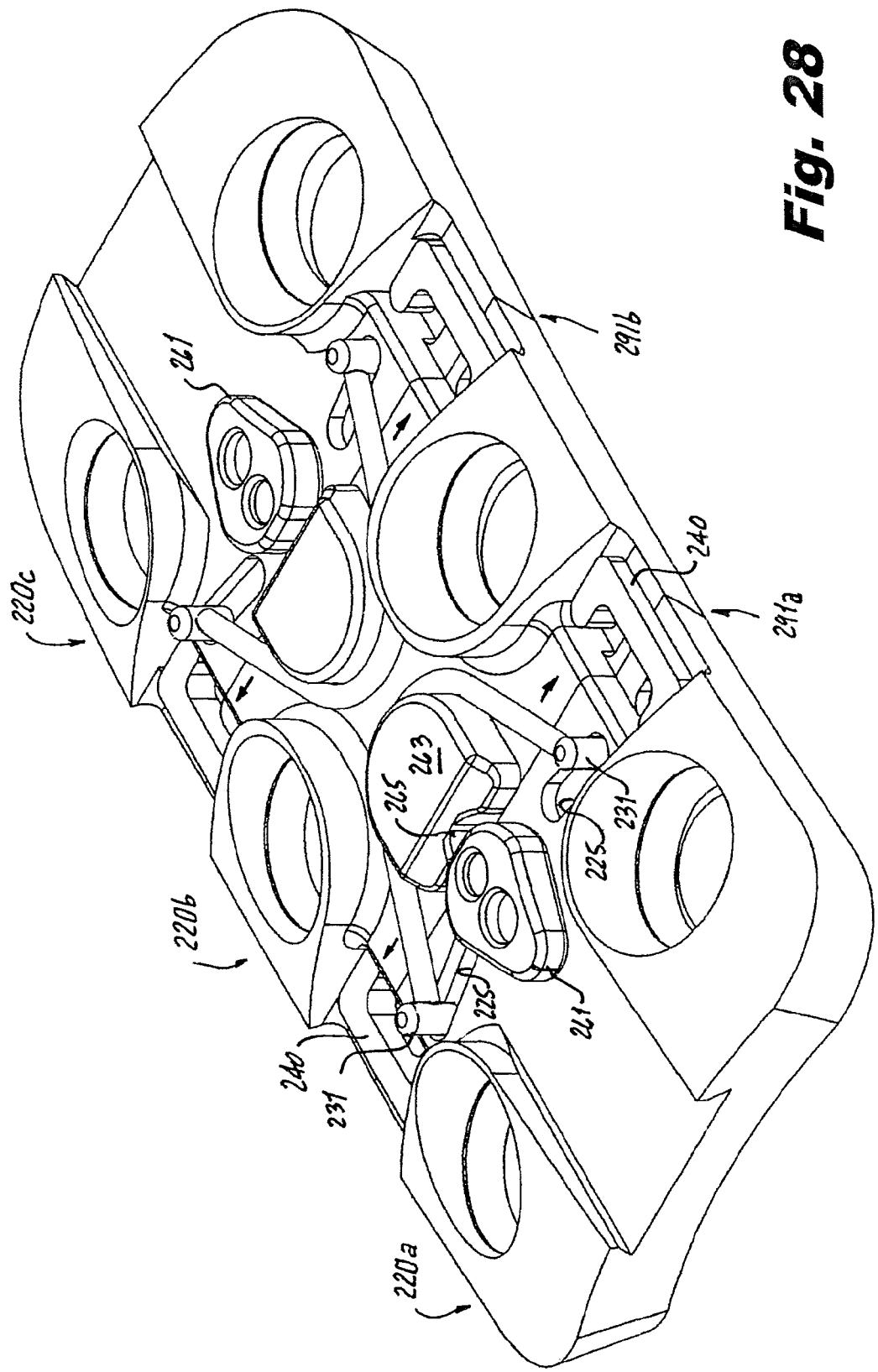

FIG. 26 illustrates the construct 200 in an expanded condition, just after disengagement of the cams 261 from the opposing recesses 265. As illustrated in FIGS. 28 and 29, in the absence of an attached spinal segment, upon disengagement of the cam 261 from the opposing recess 265, the outer plate segments 210a, 210c are pulled inward by the action of the springs 230.

FIGS. 30A-C illustrate implantation of the dynamic vertebral column plate system construct 200 of FIGS. 16-29 in various stages of attachment to a spinal segment 90. FIG. 30A illustrates the construct 200, in an expanded condition, attached to three vertebral bodies 91, 93 and 95, and spanning two intervertebral spaces 92 and 94 of a spinal segment 90, and insertion of a screw 150 with an insertion tool 81 therefor. FIG. 30B illustrates the construct 200 during disengagement of the lower cam 261 with a tool 83 therefor. FIG. 30C is a plan view of the construct 200, with the upper plate 210 removed for visibility, following disengagement of each cams 261 from its respective opposing recess 265. Force applied by the springs 230 is indicated by arrows, with resultant force applied to the spinal segment illustrated by arrows parallel to the longitudinal axis thereof. As illustrated, the cams 261 can't rotate fully away from the adjacent plate due to the position of pins 231 following disengagement. However, as settling occurs and the pins 231 move laterally outward, the cam 261 can continue to rotate away from the adjacent plate.

Figure 31A:
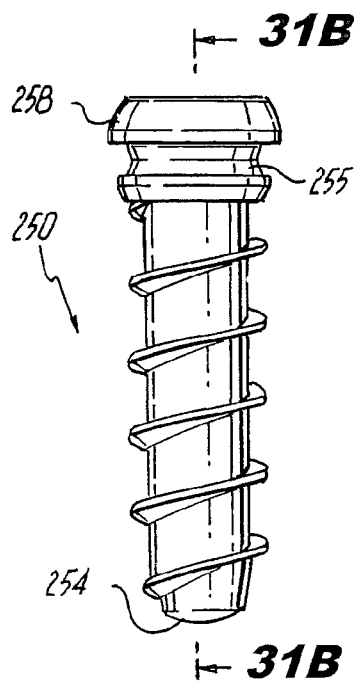
Figure 31B:
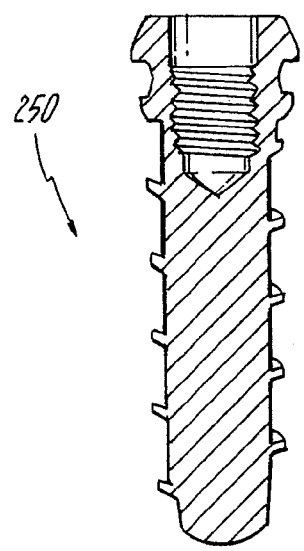

FIGS. 31A-H are side and cross-sectional views of various screw configurations for use with the dynamic vertebral column plate systems of the invention. FIGS. 31A and 31B illustrate a screw 250 having a self-tapping end 254 and a head 258 permitting variable angle engagement with an attached plate. A groove 255 is provided in the head 258 of the screw 250 for receiving a locking element, which can be any suitable element, including but not limited to a resilient o-ring, circlip, or another suitable element, such as a latching toroidal coil available from Bal Seal Engineering, Inc. of Foothill Ranch, Calif., USA. The locking element can be formed of any suitable material, such as a metal, metal alloys, an elastomeric material, silicone, polychloroprene (e.g. Neoprene), or a plastic material such as polyetheretherketone (PEEK), for example. The locking element, carried by the screw can seat in a groove provided in the construct being used.

Figure 31C:
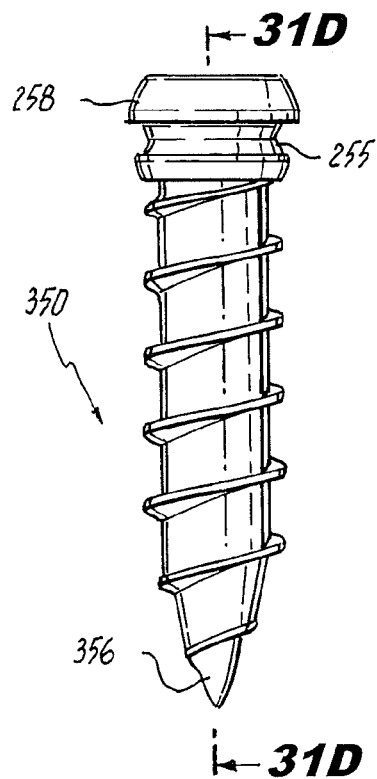
Figure 31D:
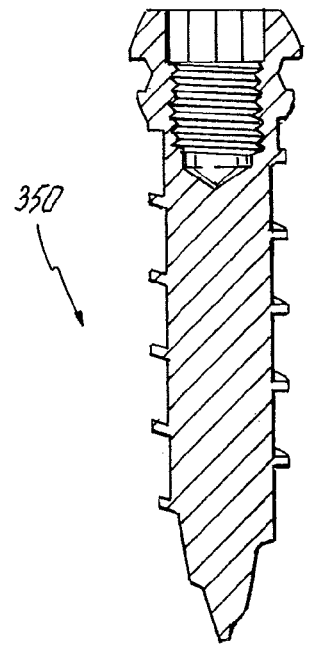

As with the screw 150 discussed in connection with the embodiment of FIGS. 1-15F, the screw 250 includes a socket 153 for engaging an insertion tool for implantation, and internal threads 153 are preferably provided to facilitate removal of the screw 250, if necessary. FIGS. 31C and 31D are side and cross-sectional views of a screw 350, having a head 258 permitting variable angle engagement, and a self-drilling end 356. FIGS. 31E and 31F are side and cross-sectional views of a screw 450 having a head 459 permitting only fixed-angle engagement with an attached plate, due to the trapezoidal cross-section thereof, as compared with the more rounded cross-section of the head 258 of screws 250 and 350. The screw 450 also includes a self-drilling end 356. FIGS. 31G and 31H illustrate a screw 550 with a head 459 for fixed-angle engagement, and a self-tapping end 254.

Figure 32A:
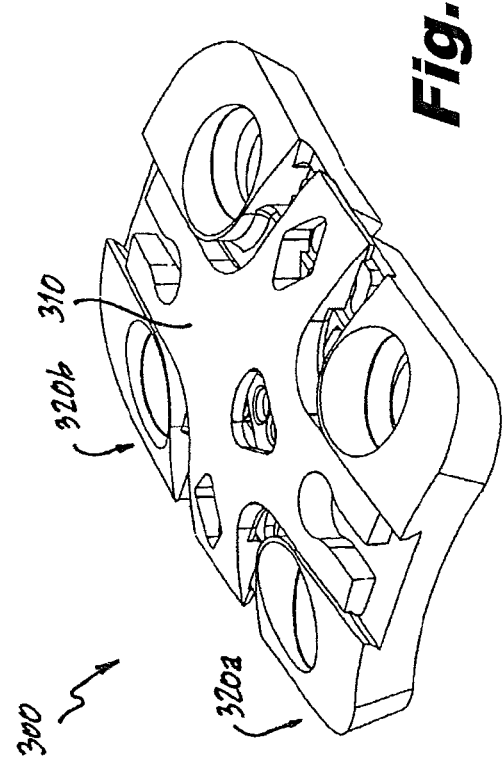
FIG. 32A is an isometric view of a dynamic vertebral column plate system construct in accordance with the invention, having two levels of plate segments.

FIG. 32A is an isometric view of a dynamic vertebral column plate system construct 300 in accordance with the invention having two levels of plate segments, 320a, 320b and a unitary upper plate 310. The internal components can be any of those illustrated herein, but as illustrated, the construct 300 is provided with a spring arrangement similar to that of the construct 200 described in connection with FIGS. 16-29.

Figure 32B:
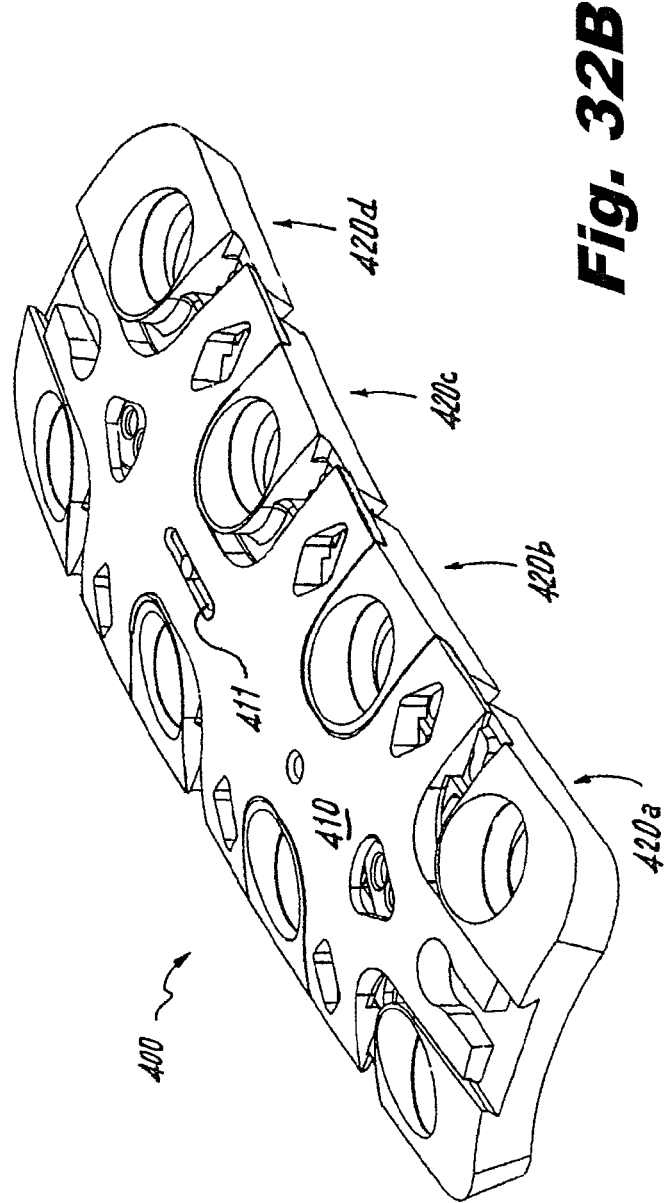
FIG. 32B is an isometric view of a dynamic vertebral column plate system construct in accordance with the invention, having four levels of plate segments.

FIG. 32B is an isometric view of a dynamic vertebral column plate system construct 400 in accordance with the invention having four levels of plate segments, 420a, 420b, 420c and 420d, and a unitary upper plate 410. The internal components can be any of those illustrated herein, but as illustrated, the construct 400 is provided with a spring arrangement similar to that of the construct 200 described in connection with FIGS. 16-29. As discussed above, the intermediate plates 420a, 420b can be connected by way of a pin, or in an alternative manner.

In any case, it is generally preferred, but not required, that no more than one lower plate segment (e.g. 420a-d) be non-translatably secured to the upper plate 410. In the case of a two-level construct, one level can be pinned to the upper plate, or alternatively, both can be slideable with respect thereto. In the case of a three-level construct, as illustrated in FIGS. 16-29, the intermediate plate can be non-translatably secured by a pin or other feature. Although a dovetail feature can be applied to intermediate plates, connection with one or more pins may provide for easier assembly of the construct 400. Accordingly, in a four-level construct, as with construct 400, one of the intermediate plates, e.g., 420b can be non-translatably pinned, while the other of the intermediate plates e.g., 420c can be pinned by way of a slot 411 in the upper plate 410. Such a pin and slot 411 configuration can additionally be applied to, or alternatively in place of, any dovetail configuration described herein, if desired.

In accordance with the invention, the number of lower plates can be selected as desired. In practice, the number of lower plate levels that would typically be used would range from between two and six. Accordingly, any construct in accordance with the invention could include five or six levels, even though those are not explicitly illustrated herein.

FIGS. 33-39 various views of further exemplary embodiment of a dynamic vertebral column plate system construct 500 in accordance with the invention, having band-shaped springs 530 and an integral cam element 561 adapted and configured to permit a plurality of selectable preloads. The springs 530 can be formed of any suitable material, but in accordance with one preferred embodiment are a shape memory alloy, such as Nitinol.

Figure 33:
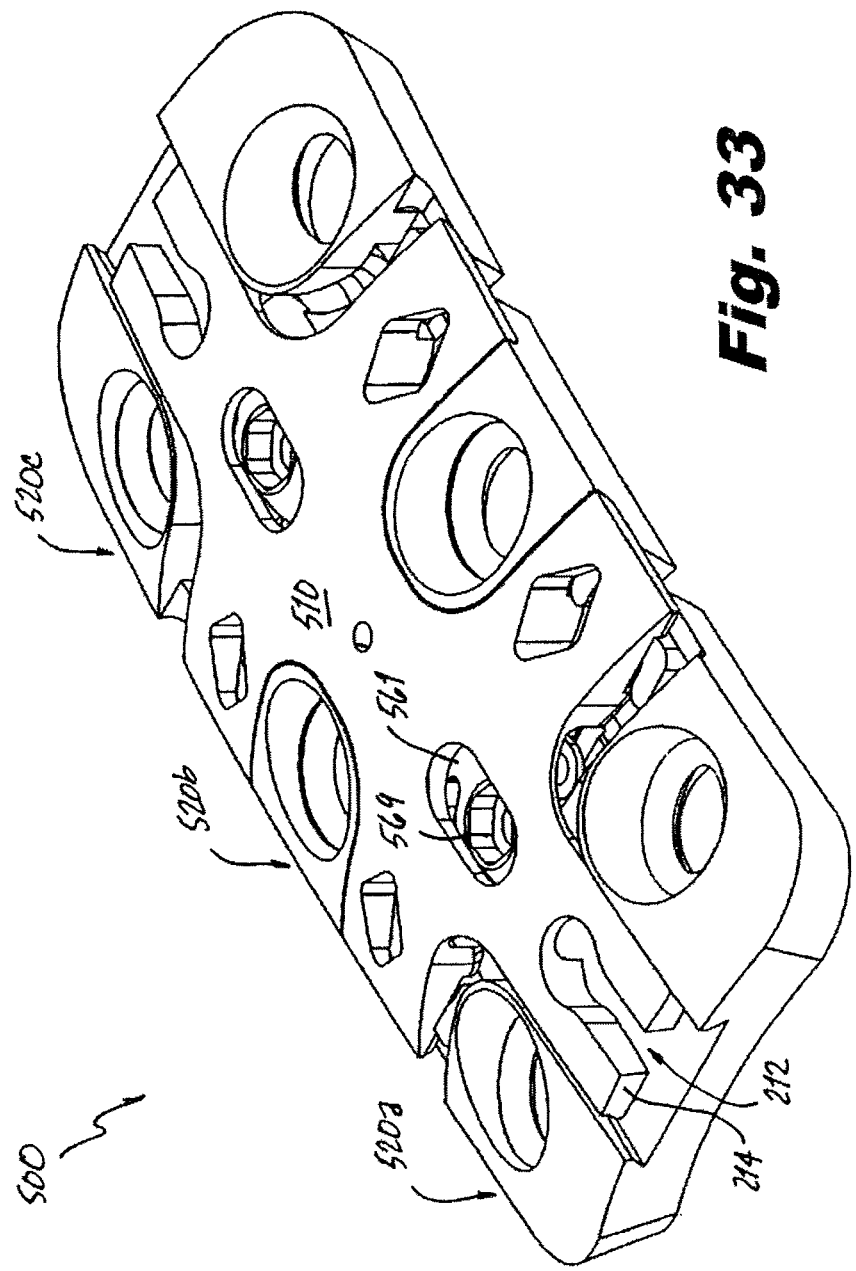
FIGS. 33-39 various views of further exemplary embodiment of a dynamic vertebral column plate system construct in accordance with the invention, having band-shaped springs and an integral cam element configured to permit a plurality of selectable preloads.
Figure 34:
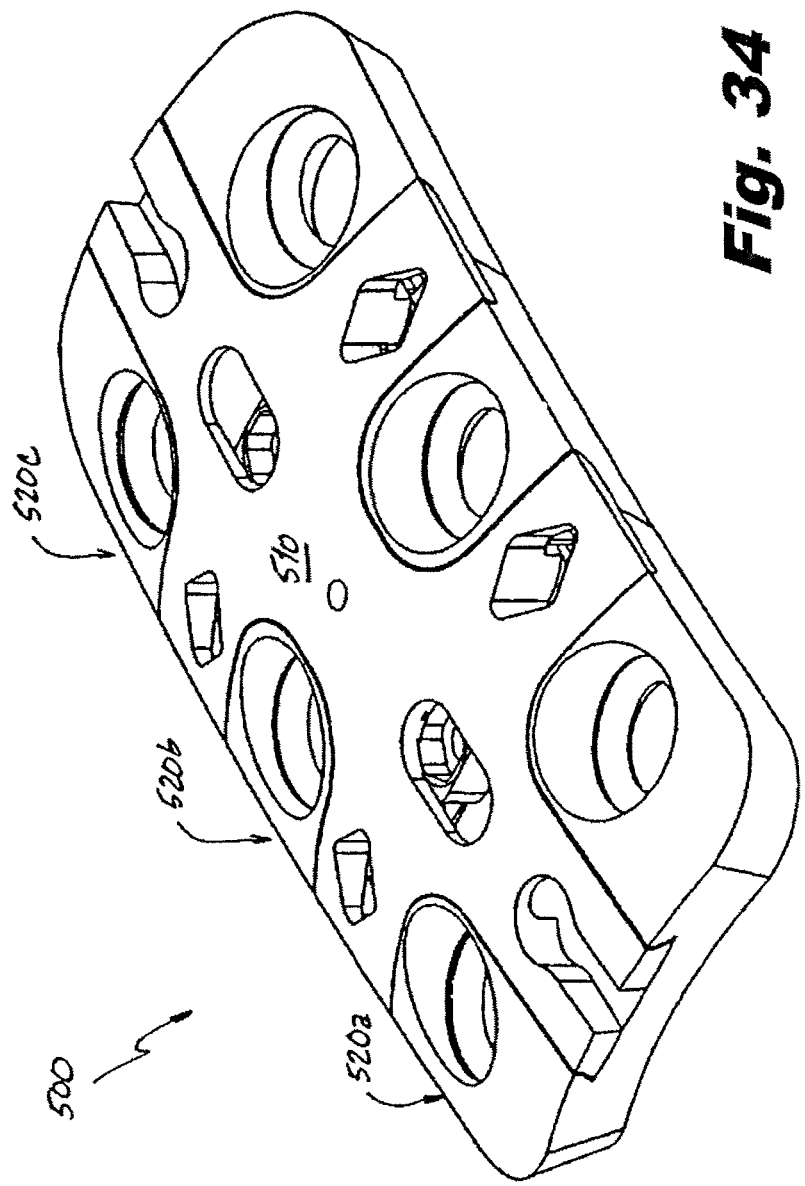
Figure 35:
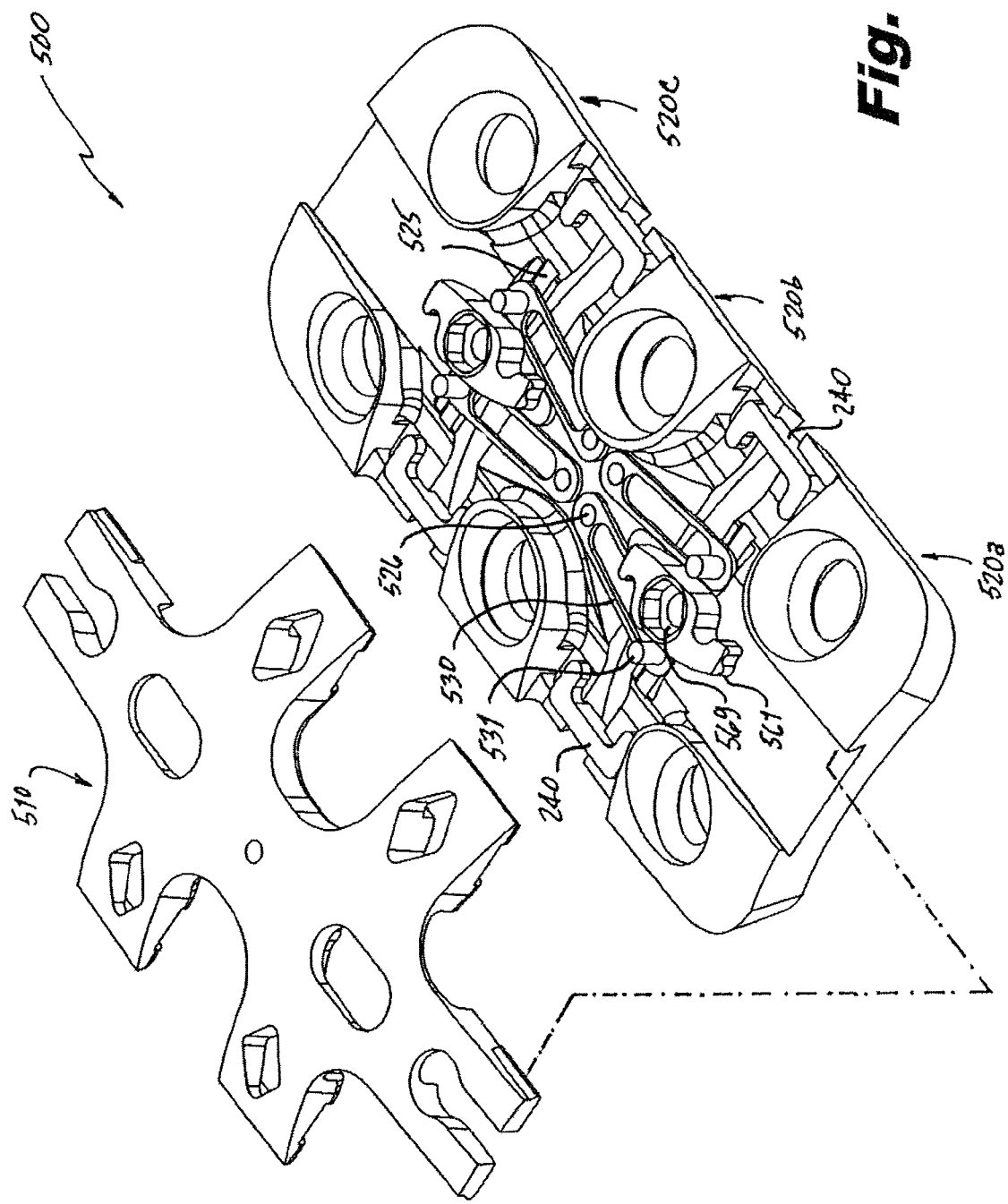
Figure 36:
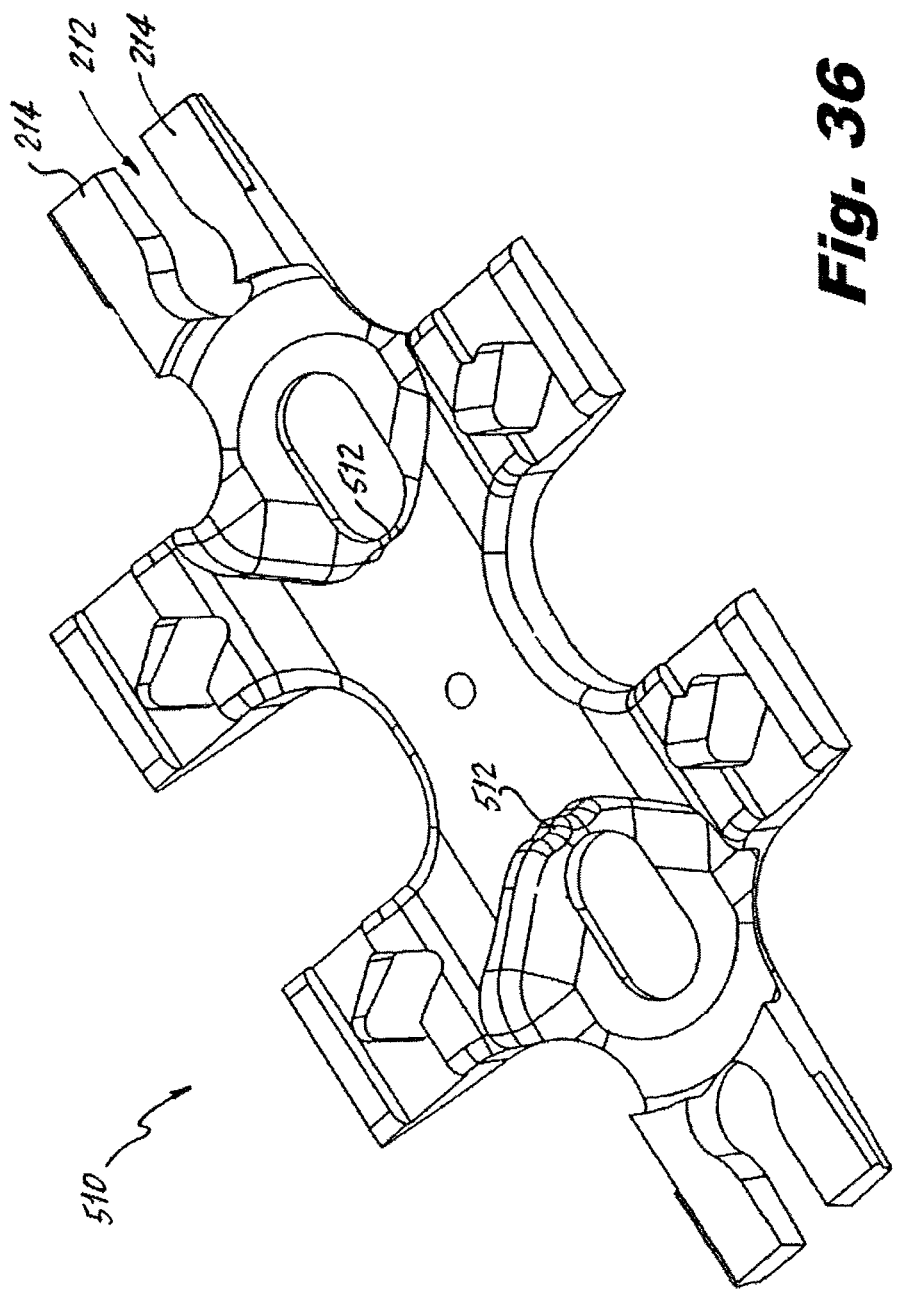
Figure 37:
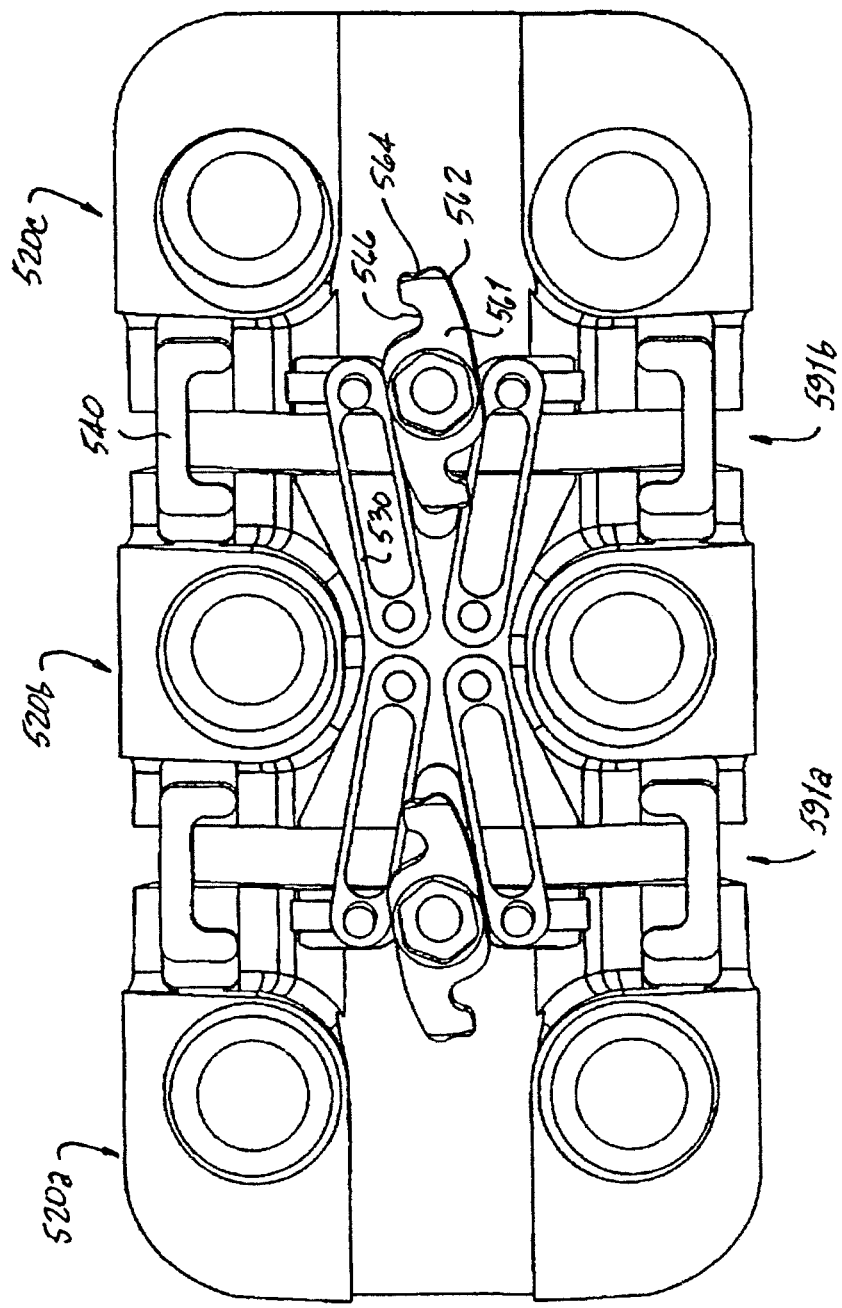

As with the construct 200 illustrated in FIGS. 16-29, a unitary upper plate 510 is provided. Different from that embodiment, however, the upper plate 510 of the construct 500 of FIGS. 33-39 includes a camming surface 512 on the underside thereof, as best seen in FIG. 36. When the cams 561 are rotated in line with the central axis of the construct 500, as illustrated in FIGS. 33, 35 and 37, they engage the camming surface 512, which then serves to push the outer plate segments 520a, 520c outward, away from the intermediate plate 520b, because the cams 561 are rotatably attached to the outer plate segments 520a, 520c, and the upper plate 510 is secured to the intermediate plate 520b. Accordingly, the construct 500 can in implanted with the cams 561 in such an orientation.

Following attachment of the construct 561 to a spinal segment, each of the cams can be rotated either clockwise or counter-clockwise. The shape of the cams 561 is generally oblong, having opposed projections 562 extending therefrom, and a socket 569 to engage with a tool for actuating the cams 561. The projections 562 include on their outer ends, detents 564 for catching slideable pins 531 when the cams 561 are rotated clockwise, and inner hooks 566 for catching the slideable pins 531 when the cams 561 are rotated counter-clockwise. The two positions of each cam 561 permit selectable levels of tension of the springs 530, and thus selectable levels of preload applied to a spinal segment. Such a cam arrangement can be applied to the other embodiments of constructs described herein, including, but not limited to the construct 200 described in connection with FIGS. 16-29.

As with the construct 200 described above, the slideable pins 531 are held in tracks 525, which are, as embodied, substantially parallel to the inner edges of the end plate segments 520a, 520c.

When implanting the construct 500 on a spinal segment, therefore, spacing between adjacent plates is maintained by the cams 561, engaging the camming surface 512 of the upper plate 510. Following attachment to respective vertebrae, one or more cams 561 can be left in the axial position, thus essentially providing a static plate at that level. If dynamic loading is desired at one or more levels, the respective cam 561 is then rotated either clockwise or counter-clockwise, as described above, securing the slideable pins 531 in either an intermediate position or at their most laterally outward extent.

Figure 38:
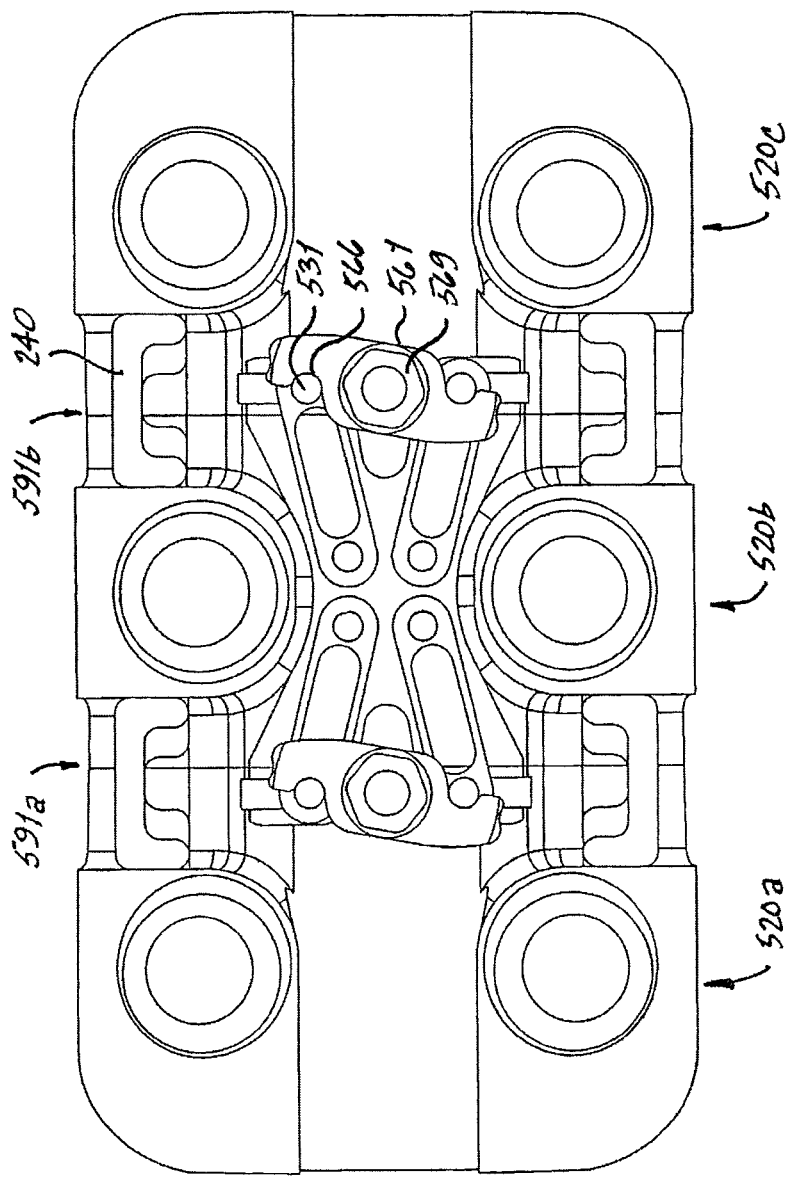

During implantation, a surgeon can apply the smaller of the two selectable preloads by rotating one or both of the cams 561 counter-clockwise, leaving the cam 561 in the position illustrated in FIG. 38. The surgeon can then evaluate whether the preload is sufficient to produce the desired effect, such as in reducing gaps between adjacent vertebrae and fusion materials. If an increased preload is desired, the cam 561 can then be rotated clockwise (by about one-half of a rotation), leaving the cam 561 in the position illustrated in FIG. 39, or vice versa.

Figure 39:
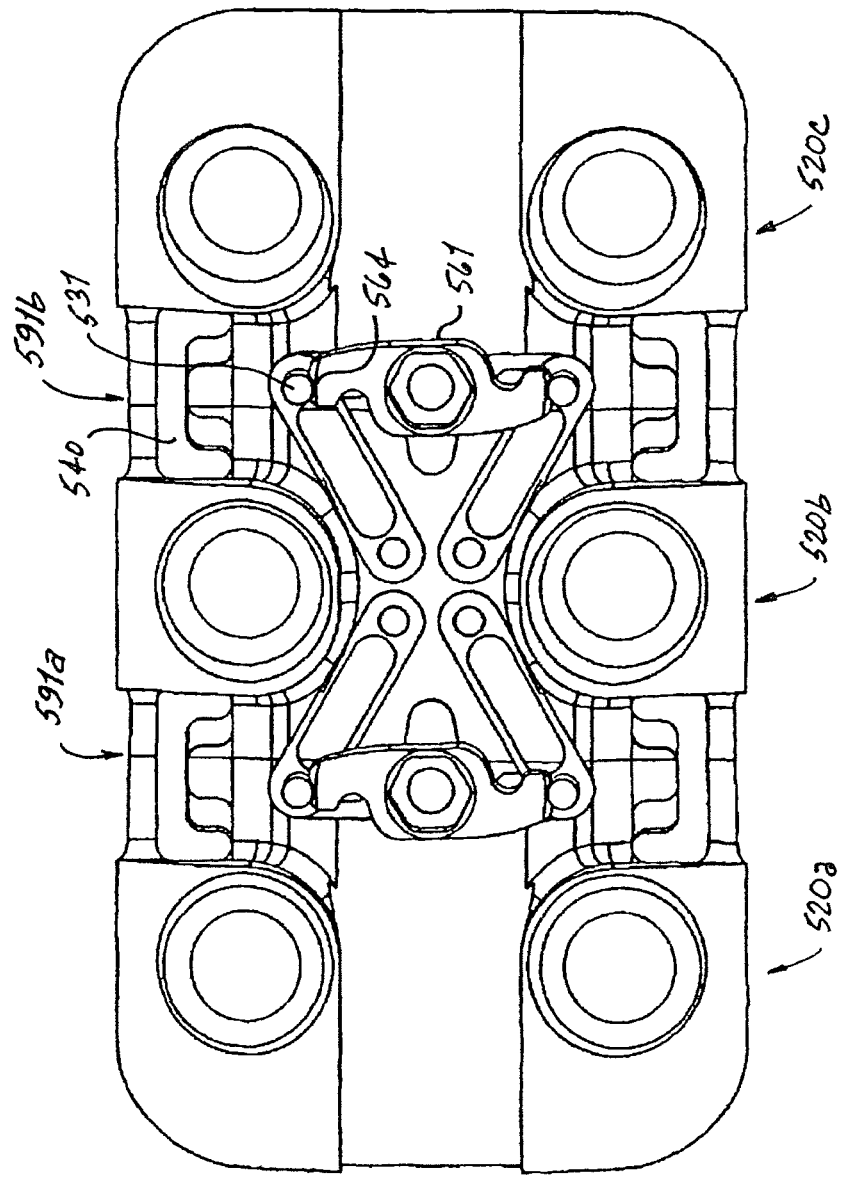

It should be noted that in the closed arrangement of the construct 500 illustrated in FIGS. 38 and 39, the gaps 591a and 591b are fully closed because the construct is not connected to a spinal segment. If the construct were connected to a spinal segment, gaps 591a, 591b would remain open indefinitely if the respective cam(s) 561 were left in the locked position (parallel to the longitudinal axis), and would likely remain open indefinitely to some extent, unless a fusion material settled to such an extent after implantation that the intervertebral space contracted by the entire amount of the respective gap 591a, 591b.

Materials for the components set forth above, including the plate segments 110, 120, can include stainless steels, titanium alloys, memory metals such as Nitinol, polymeric materials, ceramic materials such as silicon nitride or composite materials, for example.

Devices in accordance with the invention are applicable to any region of the vertebral column, such as from the first cervical vertebra (C1) to the first sacral vertebra (S1). When used in different locations along the spinal column, the plate segments 110, 120, engagement members 140, springs 130 and screws 150 are sized according to the size of the vertebral bodies in that region and to the loading conditions that will be experienced.

Kits in accordance with the invention can be provided, and include a range of plate sizes, springs 130 with varying stiffnesses, engagement members with varying stiffnesses and/or shapes, bone screws of varying sizes, and can include fixed and/or variable angle (polyaxial) screws. Kits can include plates having sizes suitable for cervical and/or thoracic and/or lumbar and/or sacral application.

The devices, systems and methods of the present invention, as described above and shown in the appended drawings, provide for vertebral column plate system constructs and related systems, methods and kits with superior properties and versatility, and adaptably enhance fusion of a bone graft.

In short, constructs in accordance with the invention can be selectively dynamic, the dynamism can be passive or active, and if active, a level of preload can be easily selected. That is, constructs in accordance with the invention can be used as completely static (being dynamically active at no levels) constructs, can be used as static at one or more levels and dynamic at the remaining levels, or can be used as dynamic at all levels. Moreover, the selectable dynamism can be active, such as in which a preload is applied by the construct, or alternatively passive, in which forces are managed through load sharing between the attached spinal segment and the construct.

In applications of passive dynamism in accordance with the invention, constructs can be configured to provide a predetermined amount of resistance to compressive forces in translation and/or bending between adjacent plate segments, thereby allowing for a predetermined amount of load sharing between the construct and the vertebral column segment. The active dynamism can include a preload that is selectable, such as by varying tension in one or more members, such as in one or more springs. Moreover, it should be noted that although the term "spring" is used herein, it is to be understood that the appearance of such a spring can vary from and is not limited to conventional notions of springs.

It is to be understood that Applicant conceives that features described herein in connection with one embodiment can advantageously be applied any other embodiment described herein, even if such feature is not explicitly described in connection with such embodiment, except where such features are mutually exclusive. That is, it is specifically conceived that elements of one embodiment are interchangeable with those of another embodiment, without limitation, except if such features would be incompatible with other features or necessarily displace another feature, for example. It will be apparent to those skilled in the art that further modifications and variations can be made in the devices, systems and methods of the present invention without departing from the spirit or scope of the invention.

What is claimed is:

1. A method of implanting an elongated vertebral column construct on a spinal segment, the method comprising, in any order, the steps of:
   a) securing each of a plurality of plates of the construct to respective vertebrae, wherein the plurality of plates includes a first plate and a second plate, the first plate defining a first groove and a second groove set an angles to an axis of the elongated vertebral column construct;
   b) determining whether to apply a preload between first and second levels of vertebrae;
   c) applying a first preload between said first and second levels of vertebrae by providing a spring extending between adjacent plates to exert a net axial compressive force between the adjacent plates, wherein the spring is a U-shaped spring having a first end and a second end with a curved portion extending between the ends, the U-shaped spring exerts the net axial compressive force by having the first end slideably captured in the first groove formed in the first plate and the second end slideably captured in the second groove formed in the first plate; and
   d) applying a second preload, in place of the first preload, between said first and second levels of vertebrae, wherein the step of applying the second preload includes rotating a first cam in a second preload direction to adjust tension in the spring as the first and second ends slide in the respective first and second grooves.

2. The method of claim 1, wherein the step of applying the first preload includes rotating the first cam of the dynamic vertebral column construct in a first preload direction.

3. The method of claim 1, further comprising the step of: evaluating efficacy of the first preload.

4. The method of claim 1, further comprising the steps of:
   a) determining whether to apply a preload between first and second levels of vertebrae; and
   b) applying a third preload between said second and third levels of vertebrae.

5. The method of claim 4, wherein the step of applying the third preload includes rotating a second cam of the dynamic vertebral column construct in a first direction.

6. The method of claim 4, further comprising the steps of:
   a) evaluating efficacy of the third preload; and
   b) applying a fourth preload, in place of the third preload, between said second and third levels of vertebrae, the fourth preload being different from the third preload.

7. The method of claim 1, wherein the second preload is different from the first preload.

8. A method of implanting a vertebral column construct on a spinal segment, the method comprising, in any order, the steps of:
   a) securing each of at least two plates of the vertebral column construct to respective vertebrae, wherein the plurality of plates includes a first plate and a second plate, the first plate defining a first groove and a second groove set an angles to an axis of the elongated vertebral column construct;
   b) applying a first preload between first and second levels of vertebrae by providing a spring extending between the at least two plates to exert a net axial compressive force between the at least two plates, wherein the spring is a U-shaped spring having a first end and a second end with a curved portion extending between the ends, the U-shaped spring exerts the net axial compressive force by having the first end slideably captured in the first groove formed in the first plate and the second end slideably captured in the second groove formed in the first plate; and
   c) applying a second preload, in place of the first preload, between said first and second levels of vertebrae, wherein the step of applying the second preload includes rotating a first cam to a second position to adjust tension in the spring as the first and second ends slide in the respective first and second grooves.

9. The method of claim 8, wherein the step of applying the first preload includes rotating the first cam to a first preload position.

* * * * *